United States Patent
Sabatini et al.

(10) Patent No.: US 11,092,608 B2
(45) Date of Patent: Aug. 17, 2021

(54) METHODS OF IDENTIFYING MODULATORS OF CASTOR1-GATOR2 INTERACTION AND USE OF SAME TO MODULATE MTORC1

(71) Applicants: Whitehead Institute for Biomedical Research, Cambridge, MA (US); President and Fellows of Harvard College, Cambridge, MA (US)

(72) Inventors: David M. Sabatini, Cambridge, MA (US); Lynne Chantranupong, Jamaica Plain, MA (US); Robert A. Saxton, Cambridge, MA (US); Steven P. Gygi, Foxborough, MA (US); Melanie P. Gygi, Foxborough, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 16/067,110

(22) PCT Filed: Dec. 28, 2016

(86) PCT No.: PCT/US2016/068995
§ 371 (c)(1),
(2) Date: Jun. 28, 2018

(87) PCT Pub. No.: WO2017/117281
PCT Pub. Date: Jul. 6, 2017

(65) Prior Publication Data
US 2019/0025321 A1 Jan. 24, 2019

Related U.S. Application Data

(60) Provisional application No. 62/271,997, filed on Dec. 28, 2015, provisional application No. 62/278,415, filed on Jan. 13, 2016.

(51) Int. Cl.
| | | |
|---|---|---|
| *G01N 33/53* | (2006.01) | |
| *G01N 33/68* | (2006.01) | |
| *A61K 31/198* | (2006.01) | |
| *A61K 31/223* | (2006.01) | |
| *G01N 33/50* | (2006.01) | |
| *G01N 33/533* | (2006.01) | |
| *G01N 33/543* | (2006.01) | |
| *A61K 38/00* | (2006.01) | |

(52) U.S. Cl.
CPC ....... *G01N 33/6845* (2013.01); *A61K 31/198* (2013.01); *A61K 31/223* (2013.01); *G01N 33/5041* (2013.01); *G01N 33/533* (2013.01); *G01N 33/54306* (2013.01); *G01N 33/6872* (2013.01); *A61K 38/00* (2013.01); *G01N 2500/02* (2013.01)

(58) Field of Classification Search
None
See application file for complete search history.

(56) References Cited

U.S. PATENT DOCUMENTS

| 10,126,303 B2 | 11/2018 | Sabatini et al. |
| 2014/0249045 A1 | 9/2014 | Kim et al. |
| 2017/0027897 A1 | 2/2017 | Sabatini et al. |
| 2017/0082633 A1 | 3/2017 | Sabatini et al. |
| 2017/0285043 A1 | 10/2017 | Sabatini et al. |

FOREIGN PATENT DOCUMENTS

| WO | WO 2013/043012 A2 | 3/2013 |
| WO | WO 2013/053919 A2 | 4/2013 |
| WO | WO 2014/153118 A1 | 9/2014 |
| WO | WO 2015/168617 A2 | 11/2015 |
| WO | WO2015/173398 | 11/2015 |
| WO | WO 2016/040824 A2 | 3/2016 |

OTHER PUBLICATIONS

Chantranupong, et al, "The CASTOR proteins are arginine sensors for the mTORC1 pathway." Cell 165.1 (2016): 153-164.
Chantranupong, et al. "The Sestrins interact with GATOR2 to negatively regulate the amino-acid-sensing pathway upstream of mTORC1." Cell reports 9.1 (2014): 1-8.
Saxton, et al. "Mechanism of arginine sensing by CASTOR1 upstream of mTORC1." Nature 536.7615 (2016): 229-233.
Hallett, et al., "CASTORing new light on amino acid sensing." Cell 165.1 (2016): 15-17.
Bar-Peled, Liron, and David M. Sabatini. "Regulation of mTORC1 by amino acids." Trends in cell biology 24.7 (2014): 400-406.
Wang, Shuyu, et al. "Lysosomal amino acid transporter SLC38A9 signals arginine sufficiency to mTORC1." Science 347.6218 (2015): 188-194.
Jewell, Jenna L., et al. "Differential regulation of mTORC1 by leucine and glutamine." Science 347.6218 (2015): 194-198.
Rebsamen, Manuele, et al. "SLC38A9 is a component of the lysosomal amino acid sensing machinery that controls mTORC1." Nature 519.7544 (2015): 477-481.
Sabatini, David M., Abstract "Cell Growth Signaling in Cancer Development," National Institutes of Health Grant No. R01 CA129105-01A1, funded on Apr. 8, 2008, through R01 CA129105-09, funded on Jan. 27, 2016.
Sabatini, David M., Abstract "Regulation of the MTOR Growth Pathway by Nutrients," National Institutes of Health Grant No. R01 CA103866-01, funded on Mar. 23, 2004, through R01 CA103866-13, funded on May 20, 2016.
Sabatini, David M., Abstract "Translational Control by Rapamycinsensitive Signaling," National Institutes of Health Grant No. R01 AI047389-01, funded on Apr. 1, 2000, through R37 AI047389-17, funded on Apr. 21, 2016.
Wells, J.A., (1990). Additivity of mutational effects in proteins. Biochemistry. 29(37): 8509-8517.

(Continued)

*Primary Examiner* — Michael D Pak

(74) *Attorney, Agent, or Firm* — Morse, Barnes-Brown & Pendleton, P.C.; Lisa M. Warren, Esq.; Erin E. Bryan, Esq.

(57) ABSTRACT

The invention relates to methods of identifying compounds that modulate mTORC1 activity in a cell by modulating the activity of CASTOR1, as well as to the use of such identified compounds in the modulation of mTORC1 and the treatment of diseases and conditions characterized by aberrant mTORC1 activity.

7 Claims, 35 Drawing Sheets

Specification includes a Sequence Listing.

(56) References Cited

OTHER PUBLICATIONS

Ngo, et al. (1994). Computational complexity, protein structure prediction, and the Levinthal paradox. In Marz and Le Grand (Eds). The protein Folding Problem and Tertiary Structure Prediction. Birkhauser: Boston, pp. 491-495.

Maiese, Kenneth, et al. "rnTOR: on target for novel therapeutic strategies in the nervous system." *Trends in molecular medicine* 19.1 (2013): 51-60.

Lamming, Dudley W., et al. "Rapalogs and mTOR inhibitors as anti-aging therapeutics." *The Journal of clinical investigation* 123.3 (2013): 980-989.

Ben-Sahra, I., et al. "Sestrin2 integrates Akt and mTOR signaling to protect cells against energetic stress-induced death." *Cell Death & Differentiation*, Dec. 14, 2013, vol. 20, pp. 611-619.

Bar-Peled, Liron, et al. "A Tumor suppressor complex with GAP activity for the Rag GTPases that signal amino acid sufficiency to mTORC1." *Science*, May 31, 2013, vol. 340, No. 6136, pp. 1100-1106.

Parkhitko, A. A., et al. "Kinase mTOR: regulation and role in maintenance of cellular homeostasis; tumor development, and aging." *Biochemistry* (Moscow), Feb. 2014, vol. 79, No. 2, pp. 88-101.

Parmigiani, Anita, et al. "Sestrins inhibit mTORC1 kinase activation through the GATOR complex." *Cell Reports*, Oct. 19, 2014, vol. 9, pp. 1281-1291.

Kim, Jeong Sig, et al. "Sestrin2 inhibits mTORC1 through modulation of GATOR complexes." *Scientific Reports*, Mar. 30, 2015, vol. 5, pp. 1-10.

Kitada, Munehiro, et al., "Nutrient Sensing and Regulation of Cellular Functions," Kagaku to seibutsu (*Chemistry and Biology*), 2013, vol. 51, pp. 294-301.

Budanov, Andrei V., and Michael Kann. "p53 target genes sestrin1 and sestrin2 connect genotoxic stress and mTOR signaling." *Cell* 134.3 (2008): 451-460.

Wolfson, RI, et al., "Sestrin2 is a Leucine Sensor for the inTORC1 Pathway," Science, vol. 351, No. 6268, Jan. 1, 2016, pp. 43-48.

International Search Report and Written Opinion for International Application No. PCT/US2016/068995, dated May 16, 2017.

International Search Report and Written Opinion issued in International Application No. PCT/US2015/028885, dated Nov. 2, 2015.

Extended European Search Report in Application No. EP 15 78 6697 dated Aug. 9, 2017.

International Search Report and Written Opinion for International Applicatation No. PCT/US2015/049727, dated Apr. 11, 2016.

Extended European Search Report in Application No. EP 15840018.4, dated Jan. 24, 2018.

8A
HEK-293T cell line stably expressing: shGFP, shCASTOR2_3, shCASTOR2_2
CASTOR2 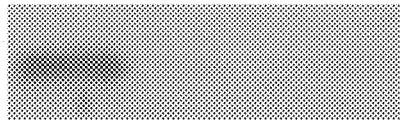
raptor 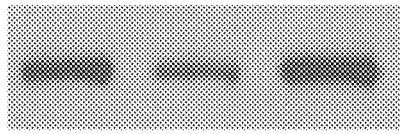
8B
HEK-293T cell line stably expressing: shGFP, shCASTOR1_2
CASTOR1 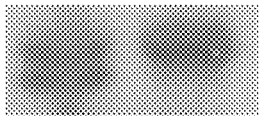 ◄
raptor 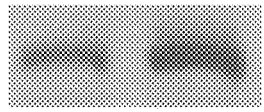
FIGS. 8A-8B

```
                       SEQUENCE LISTING

<160> NUMBER OF SEQ ID NOS: 36

<210> SEQ ID NO 1
<211> LENGTH: 25
<212> TYPE: DNA
<213> ORGANISM: Unknown
<220> FEATURE:
<223> OTHER INFORMATION: guide RNA

<400> SEQUENCE: 1
caccgtgtag agccagagac cggga                                           25

<210> SEQ ID NO 2
<211> LENGTH: 25
<212> TYPE: DNA
<213> ORGANISM: Unknown
<220> FEATURE:
<223> OTHER INFORMATION: guide RNA

<400> SEQUENCE: 2
aaactcccgg tctctggctc tacac                                           25

<210> SEQ ID NO 3
<211> LENGTH: 25
<212> TYPE: DNA
<213> ORGANISM: Unknown
<220> FEATURE:
<223> OTHER INFORMATION: guide RNA

<400> SEQUENCE: 3
caccggagca gcttgatgag cgggt                                           25

<210> SEQ ID NO 4
<211> LENGTH: 25
<212> TYPE: DNA
<213> ORGANISM: Unknown
<220> FEATURE:
<223> OTHER INFORMATION: guide RNA

<400> SEQUENCE: 4
aaacacccgc tcatcaagct gctcc                                           25
```

```
<210> SEQ ID NO 5
<211> LENGTH: 25
<212> TYPE: DNA
<213> ORGANISM: Unknown
<220> FEATURE:
<223> OTHER INFORMATION: guide RNA

<400> SEQUENCE: 5
caccggacac gtggtgctcg gccag                                           25

<210> SEQ ID NO 6
<211> LENGTH: 25
<212> TYPE: DNA
<213> ORGANISM: Unknown
<220> FEATURE:
<223> OTHER INFORMATION: guide RNA

<400> SEQUENCE: 6
aaacctggcc gagcaccacg tgtcc                                           25

<210> SEQ ID NO 7
<211> LENGTH: 67
<212> TYPE: PRT
<213> ORGANISM: Homo sapiens

<400> SEQUENCE: 7

Val Ala Glu Ala Thr Trp Leu Val Leu Asn Val Ser Ser His Ser Gly
 1               5                  10                  15

Ala Ala Val Gln Ala Ala Gly Val Thr Lys Ile Ala Arg Ser Val Ile
            20                  25                  30

Ala Pro Leu Ala Glu His His Val Ser Val Leu Met Leu Ser Thr Tyr
        35                  40                  45

Gln Thr Asp Phe Ile Leu Val Arg Glu Gln Asp Leu Ser Val Val Ile
    50                  55                  60

His Thr Leu
65

<210> SEQ ID NO 8
<211> LENGTH: 67
<212> TYPE: PRT
<213> ORGANISM: Homo sapiens

<400> SEQUENCE: 8

Val Ala Asp Ala Thr Trp Leu Ala Leu Asn Val Val Ser Gly Gly Gly
 1               5                  10                  15

Ser Phe Ser Ser Ser Gln Pro Ile Gly Val Thr Lys Ile Ala Lys Ser
            20                  25                  30

Val Ile Ala Pro Leu Ala Asp Gln Asn Ile Ser Val Phe Met Leu Ser
        35                  40                  45

Thr Tyr Gln Thr Asp Phe Ile Leu Val Arg Glu Arg Asp Leu Pro Phe
    50                  55                  60

Val Thr His
65

<210> SEQ ID NO 9
<211> LENGTH: 62
<212> TYPE: PRT
<213> ORGANISM: S. cerevisiae

<400> SEQUENCE: 9

Lys Lys Leu Ser Ile Val Ser Leu Val Gly Lys His Met Lys Gln Tyr
 1               5                  10                  15
```

Ile Gly Ile Ala Gly Thr Met Phe Thr Thr Leu Ala Glu Glu Gly Ile
            20                  25                  30

Asn Ile Glu Met Ile Ser Gln Gly Ala Asn Glu Ile Asn Ile Ser Cys
        35                  40                  45

Val Ile Asn Glu Ser Asp Ser Ile Lys Ala Leu Gln Cys Ile
    50                  55                  60

<210> SEQ ID NO 10
<211> LENGTH: 60
<212> TYPE: PRT
<213> ORGANISM: Clostridium

<400> SEQUENCE: 10

Glu Asp Gly Trp Arg Ala Phe Arg Ile Glu Gly Val Leu Asp Phe Ser
1               5                   10                  15

Leu Thr Gly Ile Leu Ser Glu Ile Ser Gly Val Leu Ala Gly Glu Lys
            20                  25                  30

Ile Gly Ile Phe Ala Ile Ser Thr Tyr Asn Thr Asp Tyr Ile Leu Val
        35                  40                  45

Lys Glu Glu Asn Phe Glu Lys Ala Leu Asn Ala Leu
    50                  55                  60

<210> SEQ ID NO 11
<211> LENGTH: 60
<212> TYPE: PRT
<213> ORGANISM: L. acidophilus

<400> SEQUENCE: 11

Glu Asp Gly Trp Arg Ala Phe Lys Ile Glu Gly Gln Leu Asp Phe Ser
1               5                   10                  15

Leu Ile Gly Ile Leu Ala Lys Ile Ala Gln Leu Leu Ala Asn Asn Gly
            20                  25                  30

Ile Ser Ile Phe Ala Val Ser Thr Phe Asn Thr Asp Tyr Val Leu Val
        35                  40                  45

Lys Asp Asn Asn Phe Asp Ser Ala Ile Lys Ile Leu
    50                  55                  60

<210> SEQ ID NO 12
<211> LENGTH: 65
<212> TYPE: PRT
<213> ORGANISM: P. pastoris

<400> SEQUENCE: 12

Glu Val Thr His Asp Met Ala Ile Val Ser Leu Val Gly Ile His Met
1               5                   10                  15

Lys Gln Leu Ile Gly Ile Ala Gly Ala Met Phe Lys Thr Leu Ala Asp
            20                  25                  30

Glu Arg Ile Asn Ile Glu Met Ile Ser Gln Gly Ala Asn Glu Ile Asn
        35                  40                  45

Ile Ser Cys Val Ile Asn Lys Asn Asp Thr Val Lys Ala Leu Asn Ala
    50                  55                  60

Ile
65

<210> SEQ ID NO 13
<211> LENGTH: 64
<212> TYPE: PRT
<213> ORGANISM: T. cacao

-continued

<400> SEQUENCE: 13

Glu Val Ile Pro Asn Cys Ser Ile Leu Ala Ala Val Gly Gln Lys Met
1               5                   10                  15

Ala Ser Thr Pro Gly Val Ser Ala Thr Leu Phe Asn Ala Leu Ala Lys
            20                  25                  30

Ala Asn Ile Asn Val Arg Ala Ile Ala Gln Gly Cys Ser Glu Tyr Asn
        35                  40                  45

Ile Thr Val Val Lys Arg Glu Asp Cys Ile Arg Ala Leu Arg Ala
    50                  55                  60

<210> SEQ ID NO 14
<211> LENGTH: 58
<212> TYPE: PRT
<213> ORGANISM: M. roreri

<400> SEQUENCE: 14

Thr Trp Arg Cys Ile Lys Ile Ala Gly Pro Met Ala Phe Ser Val Val
1               5                   10                  15

Gly Val Leu Ala Gln Val Thr Ala Pro Leu Gln Ala Ala Gln Cys Pro
            20                  25                  30

Val Tyr Val Thr Ser Thr Trp Asn Thr Asp Tyr Val Leu Val Pro Lys
        35                  40                  45

Asp Lys Leu Asn Leu Ala Val Asp Ala Leu
    50                  55

<210> SEQ ID NO 15
<211> LENGTH: 63
<212> TYPE: PRT
<213> ORGANISM: Homo sapiens

<400> SEQUENCE: 15

Gly Glu Leu Trp Arg Met Val Arg Ile Gly Gly Gln Pro Leu Gly Phe
1               5                   10                  15

Asp Glu Cys Gly Ile Val Ala Gln Ile Ala Gly Pro Leu Ala Ala Ala
            20                  25                  30

Asp Ile Ser Ala Tyr Tyr Ile Ser Thr Phe Asn Phe Asp His Ala Leu
        35                  40                  45

Val Pro Glu Asp Gly Ile Gly Ser Val Ile Glu Val Leu Gln Arg
    50                  55                  60

<210> SEQ ID NO 16
<211> LENGTH: 63
<212> TYPE: PRT
<213> ORGANISM: Homo sapiens

<400> SEQUENCE: 16

Ser Gly Glu Leu Trp Lys Met Val Arg Ile Gly Gly Gln Pro Leu Gly
1               5                   10                  15

Phe Asp Glu Cys Gly Ile Val Ala Gln Ile Ser Glu Pro Leu Ala Ala
            20                  25                  30

Ala Asp Ile Pro Ala Tyr Tyr Ile Ser Thr Phe Lys Phe Asp His Ala
        35                  40                  45

Leu Val Pro Glu Glu Asn Ile Asn Gly Val Ile Ser Ala Leu Lys
    50                  55                  60

<210> SEQ ID NO 17
<211> LENGTH: 61
<212> TYPE: PRT
<213> ORGANISM: D. indianesis

<400> SEQUENCE: 17

Asp Gly Phe Arg Ala Phe Arg Ile Glu Gly Lys Leu Asp Phe Thr Leu
1               5                   10                  15

Ile Gly Ile Leu Ala Lys Ile Ser Ser Ala Leu Ala Lys Asn Asn Ile
            20                  25                  30

Gly Val Phe Ala Ile Ser Thr Tyr Asn Thr Asp Tyr Ile Leu Val Lys
        35                  40                  45

Asn Ser Asp Phe Asp Lys Ala Leu Glu Val Leu Glu Glu
    50                  55                  60

<210> SEQ ID NO 18
<211> LENGTH: 60
<212> TYPE: PRT
<213> ORGANISM: Clostridium

<400> SEQUENCE: 18

Asp Gly Trp Arg Ala Phe Arg Ile Glu Gly Val Leu Asp Phe Ser Leu
1               5                   10                  15

Thr Gly Ile Leu Ser Glu Ile Ser Gly Val Leu Ala Gly Glu Lys Ile
            20                  25                  30

Gly Ile Phe Ala Ile Ser Thr Tyr Asn Thr Asp Tyr Ile Leu Val Lys
        35                  40                  45

Glu Glu Asn Phe Glu Lys Ala Leu Asn Ala Leu Lys
    50                  55                  60

<210> SEQ ID NO 19
<211> LENGTH: 59
<212> TYPE: PRT
<213> ORGANISM: S. cerevisiae

<400> SEQUENCE: 19

Val Ser Leu Val Gly Lys His Met Lys Gln Tyr Ile Gly Ile Ala Gly
1               5                   10                  15

Thr Met Phe Thr Thr Leu Ala Glu Glu Gly Ile Asn Ile Glu Met Ile
            20                  25                  30

Ser Gln Gly Ala Asn Glu Ile Asn Ile Ser Cys Val Ile Asn Glu Ser
        35                  40                  45

Asp Ser Ile Lys Ala Leu Gln Cys Ile His Ala
    50                  55

<210> SEQ ID NO 20
<211> LENGTH: 60
<212> TYPE: PRT
<213> ORGANISM: P. ciferrii

<400> SEQUENCE: 20

Ala Ile Val Ser Leu Val Gly Lys His Met Lys Gln Phe Ile Gly Val
1               5                   10                  15

Ala Ser Thr Met Phe Ser Thr Leu Ala Glu Gln Asn Ile Asn Ile Glu
            20                  25                  30

Met Ile Ser Gln Gly Ala Asn Glu Ile Asn Ile Ser Ala Val Ile Asp
        35                  40                  45

Glu Lys Asn Ala Ile Lys Ala Leu Gln Ser Ile His
    50                  55                  60

<210> SEQ ID NO 21
<211> LENGTH: 64
<212> TYPE: PRT

<213> ORGANISM: S. lycopersicum

<400> SEQUENCE: 21

Pro Asn Cys Ser Ile Leu Ala Ala Val Gly Gln Arg Met Ala Ser Thr
1               5                   10                  15

Pro Gly Val Ser Ala Thr Leu Phe Thr Ala Leu Ala Lys Ala Asn Ile
            20                  25                  30

Asn Ile Arg Ala Ile Ala Gln Gly Cys Thr Glu Tyr Asn Ile Thr Val
        35                  40                  45

Val Val Lys Arg Glu Asp Cys Val Arg Ala Leu Arg Ala Val His Ser
    50                  55                  60

<210> SEQ ID NO 22
<211> LENGTH: 61
<212> TYPE: PRT
<213> ORGANISM: L. helveticus

<400> SEQUENCE: 22

Asp Gly Trp Arg Ala Phe Lys Ile Glu Gly Gln Leu Asp Phe Ser Leu
1               5                   10                  15

Ile Gly Ile Leu Ala Lys Ile Ala Gln Leu Leu Ala Asn Asn Gly Ile
            20                  25                  30

Ser Ile Phe Ala Val Ser Thr Phe Asn Thr Asp Tyr Ile Leu Val Lys
        35                  40                  45

Asp Asn Asn Phe Asp Ser Ala Ile Lys Ile Leu Ser Glu
    50                  55                  60

<210> SEQ ID NO 23
<211> LENGTH: 329
<212> TYPE: PRT
<213> ORGANISM: Homo sapiens

<400> SEQUENCE: 23

Met Glu Leu His Ile Leu Glu His Arg Val Arg Val Leu Ser Val Ala
1               5                   10                  15

Arg Pro Gly Leu Trp Leu Tyr Thr His Pro Leu Ile Lys Leu Leu Phe
            20                  25                  30

Leu Pro Arg Arg Ser Arg Cys Lys Phe Phe Ser Leu Thr Glu Thr Pro
        35                  40                  45

Glu Asp Tyr Thr Leu Met Val Asp Glu Glu Gly Phe Lys Glu Leu Pro
    50                  55                  60

Pro Ser Glu Phe Leu Gln Val Ala Glu Ala Thr Trp Leu Val Leu Asn
65                  70                  75                  80

Val Ser Ser His Ser Gly Ala Ala Val Gln Ala Ala Gly Val Thr Lys
            85                  90                  95

Ile Ala Arg Ser Val Ile Ala Pro Leu Ala Glu His Val Ser Val
            100                 105                 110

Leu Met Leu Ser Thr Tyr Gln Thr Asp Phe Ile Leu Val Arg Glu Gln
            115                 120                 125

Asp Leu Ser Val Val Ile His Thr Leu Ala Gln Glu Phe Asp Ile Tyr
    130                 135                 140

Arg Glu Val Gly Gly Glu Pro Val Pro Val Thr Arg Asp Asp Ser Ser
145                 150                 155                 160

Asn Gly Phe Pro Arg Thr Gln His Gly Pro Ser Pro Thr Val His Pro
                165                 170                 175

Ile Gln Ser Pro Gln Asn Arg Phe Cys Val Leu Thr Leu Asp Pro Glu
            180                 185                 190

Thr Leu Pro Ala Ile Ala Thr Thr Leu Ile Asp Val Leu Phe Tyr Ser
            195                 200                 205

His Ser Thr Pro Lys Glu Ala Ala Ser Ser Pro Glu Pro Ser Ser
        210                 215                 220

Ile Thr Phe Phe Ala Phe Ser Leu Ile Glu Gly Tyr Ile Ser Ile Val
225                 230                 235                 240

Met Asp Ala Glu Thr Gln Lys Lys Phe Pro Ser Asp Leu Leu Leu Thr
            245                 250                 255

Ser Ser Ser Gly Glu Leu Trp Arg Met Val Arg Ile Gly Gly Gln Pro
            260                 265                 270

Leu Gly Phe Asp Glu Cys Gly Ile Val Ala Gln Ile Ala Gly Pro Leu
            275                 280                 285

Ala Ala Ala Asp Ile Ser Ala Tyr Tyr Ile Ser Thr Phe Asn Phe Asp
            290                 295                 300

His Ala Leu Val Pro Glu Asp Gly Ile Gly Ser Val Ile Glu Val Leu
305                 310                 315                 320

Gln Arg Arg Gln Glu Gly Leu Ala Ser
            325

<210> SEQ ID NO 24
<211> LENGTH: 329
<212> TYPE: PRT
<213> ORGANISM: Pan troglodytes

<400> SEQUENCE: 24

Met Glu Leu His Ile Leu Glu His Arg Val Arg Val Leu Ser Val Ala
1               5                   10                  15

Arg Pro Gly Leu Trp Leu Tyr Thr His Pro Leu Ile Lys Leu Leu Phe
            20                  25                  30

Leu Pro Arg Arg Ser Arg Cys Lys Phe Phe Ser Leu Thr Glu Thr Pro
        35                  40                  45

Glu Asp Tyr Thr Leu Met Val Asp Glu Glu Gly Phe Lys Glu Leu Pro
    50                  55                  60

Pro Ser Glu Phe Leu Gln Val Ala Glu Ala Thr Trp Leu Val Leu Asn
65                  70                  75                  80

Val Ser Ser His Ser Gly Ala Ala Val Gln Ala Ala Gly Val Thr Lys
                85                  90                  95

Ile Ala Arg Ser Val Ile Ala Pro Leu Ala Glu His Val Ser Val
            100                 105                 110

Leu Met Leu Ser Thr Tyr Gln Thr Asp Phe Ile Leu Val Arg Glu Gln
            115                 120                 125

Asp Leu Ser Val Val Ile His Thr Leu Ala Gln Glu Phe Asp Ile Tyr
        130                 135                 140

Arg Glu Val Gly Gly Glu Pro Val Pro Val Thr Arg Asp Asp Ser Ser
145                 150                 155                 160

Asn Gly Phe Pro Arg Thr Gln His Gly Pro Ser Pro Thr Val His Pro
                165                 170                 175

Ile Gln Ser Pro Gln Asn Arg Phe Cys Val Leu Thr Leu Asp Pro Glu
            180                 185                 190

Thr Leu Pro Ala Ile Ala Thr Thr Leu Ile Asp Val Leu Phe Tyr Ser
            195                 200                 205

His Ser Thr Pro Lys Glu Ala Ala Ser Ser Pro Glu Pro Ser Ser
        210                 215                 220

Ile Thr Phe Phe Ala Phe Ser Leu Ile Glu Gly Tyr Ile Ser Ile Val

```
            225                 230                 235                 240

Met Asp Ala Glu Thr Gln Lys Lys Phe Pro Ser Asp Leu Leu Leu Thr
                    245                 250                 255

Ser Ser Ser Gly Glu Leu Trp Arg Met Val Arg Ile Gly Gly Gln Pro
            260                 265                 270

Leu Gly Phe Asp Glu Cys Gly Ile Val Ala Gln Ile Ala Gly Pro Leu
                275                 280                 285

Ala Ala Ala Asp Ile Ser Ala Tyr Tyr Ile Ser Thr Phe Asn Phe Asp
            290                 295                 300

His Ala Leu Val Pro Glu Asp Gly Ile Gly Ser Val Ile Glu Val Leu
305                 310                 315                 320

Gln Arg Arg Gln Glu Gly Leu Ala Ser
                    325

<210> SEQ ID NO 25
<211> LENGTH: 329
<212> TYPE: PRT
<213> ORGANISM: Canis lupus familiaris

<400> SEQUENCE: 25

Met Glu Leu His Ile Leu Glu His Arg Val Arg Val Leu Ser Leu Ala
1               5                   10                  15

Arg Pro Gly Leu Trp Leu Tyr Thr His Pro Leu Ile Lys Leu Leu Phe
            20                  25                  30

Leu Pro Arg Arg Ser Arg Cys Lys Phe Phe Ser Leu Thr Glu Thr Pro
        35                  40                  45

Glu Asp Tyr Thr Leu Met Val Asp Glu Glu Gly Phe Lys Glu Leu Pro
    50                  55                  60

Pro Ser Glu Phe Leu Gln Val Ala Glu Ala Thr Trp Leu Val Leu Asn
65                  70                  75                  80

Val Ser Ser His Ser Gly Ala Thr Val Gln Ala Ala Gly Val Thr Lys
                85                  90                  95

Ile Ala Arg Ser Val Ile Ala Pro Leu Ala Glu His His Val Ser Val
            100                 105                 110

Leu Met Leu Ser Thr Tyr Gln Thr Asp Phe Ile Leu Val Arg Glu Gln
        115                 120                 125

Asp Leu Ser Val Val Ile His Thr Leu Ser Gln Glu Phe Asp Ile Tyr
    130                 135                 140

Arg Glu Val Gly Gly Glu Pro Val Pro Val Ala Arg Asp Asp Ser Ser
145                 150                 155                 160

Asn Gly Phe Pro Arg Ser Gln His Gly Pro Ser Pro Thr Val His Pro
                165                 170                 175

Ile Gln Ser Pro Gln Asn Arg Phe Cys Val Leu Thr Leu Asp Pro Glu
            180                 185                 190

Thr Leu Pro Ala Ile Ala Thr Thr Leu Ile Asp Val Leu Phe Tyr Ser
        195                 200                 205

Tyr Ser Ala Pro Lys Glu Ala Ala Ser Gly Gly Thr Gly Pro Ser Ser
    210                 215                 220

Ile Thr Phe Phe Ala Phe Ser Leu Ile Glu Gly Tyr Ile Ser Ile Val
225                 230                 235                 240

Met Asp Ala Glu Thr Gln Lys Lys Phe Pro Ser Asp Leu Leu Leu Thr
                245                 250                 255

Ser Ser Ser Gly Glu Leu Trp Arg Met Val Arg Ile Gly Gly Gln Pro
            260                 265                 270
```

```
Leu Gly Phe Asp Glu Cys Gly Ile Val Ala Gln Ile Ala Gly Pro Leu
            275                 280                 285

Ala Ala Ala Asp Ile Ser Ala Tyr Tyr Ile Ser Thr Phe Asn Phe Asp
290                 295                 300

His Ala Leu Val Pro Glu Asp Gly Ile Asn Ser Val Ile Glu Val Leu
305                 310                 315                 320

Gln Arg Arg Gln Asp Gly Gln Ser Ser
                325

<210> SEQ ID NO 26
<211> LENGTH: 329
<212> TYPE: PRT
<213> ORGANISM: Bos taurus

<400> SEQUENCE: 26

Met Glu Leu His Ile Leu Glu His Arg Val Arg Val Leu Ser Leu Ala
1               5                   10                  15

Arg Pro Gly Leu Trp Leu Tyr Thr His Pro Leu Ile Lys Leu Leu Phe
            20                  25                  30

Leu Pro Arg Arg Ser Arg Cys Lys Phe Phe Ser Leu Thr Glu Thr Pro
        35                  40                  45

Glu Asp Tyr Thr Leu Met Val Asp Glu Glu Gly Phe Lys Glu Leu Pro
    50                  55                  60

Pro Ser Glu Phe Leu Gln Val Ala Glu Ala Thr Trp Leu Val Leu Asn
65                  70                  75                  80

Val Ser Ser Pro Ser Gly Ala Ala Val Gln Ala Ala Gly Val Thr Lys
                85                  90                  95

Ile Ala Arg Ser Val Ile Ala Pro Leu Ala Glu His His Val Ser Val
            100                 105                 110

Leu Met Leu Ser Thr Tyr Gln Thr Asp Phe Ile Leu Val Arg Glu Gln
        115                 120                 125

Asp Leu Ser Val Val Ile His Thr Leu Ala Arg Glu Phe Asp Ile Tyr
    130                 135                 140

Arg Glu Val Gly Gly Glu Pro Val Pro Val Ala Arg Asp Asp Ser Ser
145                 150                 155                 160

Asn Gly Phe Pro Arg Ala Gln His Gly Pro Ser Pro Thr Val His Pro
                165                 170                 175

Ile Gln Ser Pro Gln Asn Arg Phe Cys Val Leu Thr Leu Asp Pro Glu
            180                 185                 190

Thr Leu Pro Ala Ile Ala Thr Thr Leu Ile Asp Val Leu Phe Tyr Ser
        195                 200                 205

His Ser Pro Pro Arg Glu Ala Ala Ser Gly Gly Pro Gly Ser Ser Ser
    210                 215                 220

Ile Ala Phe Phe Ala Phe Ser Leu Ile Glu Gly Tyr Ile Ser Ile Val
225                 230                 235                 240

Met Asp Ala Glu Thr Gln Lys Lys Phe Pro Ser Asp Leu Leu Leu Thr
                245                 250                 255

Ser Ser Ser Gly Glu Leu Trp Arg Met Val Arg Ile Gly Gly Gln Pro
            260                 265                 270

Leu Gly Phe Asp Glu Cys Gly Ile Val Ala Gln Ile Ala Gly Pro Leu
        275                 280                 285

Ala Ala Ala Asp Ile Ser Ala Tyr Tyr Ile Ser Thr Phe Asn Phe Asp
    290                 295                 300

His Ala Leu Val Pro Glu Asp Gly Ile Gly Ser Val Ile Glu Val Leu
305                 310                 315                 320
```

Gln Arg Arg Gln Asp Gly Leu Gly Ser
            325

<210> SEQ ID NO 27
<211> LENGTH: 331
<212> TYPE: PRT
<213> ORGANISM: Mus musculus

<400> SEQUENCE: 27

Met Glu Leu His Ile Leu Glu His Arg Val Arg Val Leu Ser Ile Ala
1               5                   10                  15

Arg Pro Gly Leu Trp Leu Tyr Thr His Pro Leu Ile Lys Leu Leu Phe
            20                  25                  30

Leu Pro Cys Arg Ser Arg Cys Lys Phe Phe Ser Leu Thr Glu Thr Pro
        35                  40                  45

Glu Asp Tyr Thr Leu Met Val Asp Glu Glu Gly Phe Lys Glu Leu Pro
    50                  55                  60

Pro Ser Glu Phe Leu Gln Val Ala Glu Ala Thr Trp Leu Val Met Asn
65                  70                  75                  80

Val Ser His Ser Gly Ser Val Val Gln Ala Ala Gly Val Thr Lys Ile
                85                  90                  95

Ala Arg Ser Val Ile Ala Pro Leu Ala Glu His His Val Ser Val Leu
            100                 105                 110

Met Leu Ser Thr Tyr Gln Thr Asp Phe Ile Leu Val Arg Glu Gln Asp
        115                 120                 125

Leu Ser Val Val Ile His Thr Leu Ala Gln Glu Phe Gln Ile Tyr Arg
    130                 135                 140

Glu Val Gly Gly Glu Pro Val Pro Val Thr Gly Asp Asp Ser Ser Asn
145                 150                 155                 160

Gly Phe Pro Gln Ile Gln His Gly Pro Ser Pro Thr Val His Pro Ile
                165                 170                 175

Gln Ser Pro Gln Asn Arg Phe Cys Val Leu Thr Leu Asp Pro Glu Thr
            180                 185                 190

Leu Pro Ala Val Ala Thr Thr Leu Ile Asp Val Leu Phe Tyr Ser His
        195                 200                 205

Ser Val Pro Lys Glu Ala Ala Ser Gly Gly Pro Glu Ser Thr Ser Ile
    210                 215                 220

Pro Phe Phe Ala Phe Ser Leu Ile Glu Gly Tyr Ile Ser Ile Val Met
225                 230                 235                 240

Asp Ala Glu Ile Gln Arg Lys Phe Pro Ser Asp Leu Leu Leu Thr Ser
                245                 250                 255

Ser Ser Gly Glu Leu Trp Arg Met Val Arg Ile Gly Gly Gln Pro Leu
            260                 265                 270

Gly Phe Asp Glu Cys Gly Ile Val Ala Gln Ile Ala Gly Pro Leu Ala
        275                 280                 285

Ala Val Asp Ile Ser Ala Tyr Tyr Ile Ser Thr Phe Asn Phe Asp His
    290                 295                 300

Ala Leu Val Pro Glu Asp Glu Ile Gly Cys Val Ile Asp Ile Leu Gln
305                 310                 315                 320

Arg Arg Gln Glu Ser Gln Ala Ser Lys Asp Pro
                325                 330

<210> SEQ ID NO 28
<211> LENGTH: 329
<212> TYPE: PRT

<213> ORGANISM: Xenopus tropicalis

<400> SEQUENCE: 28

Met Asp Leu Gln Leu Leu Glu His Arg Val Arg Val Thr Ser Ile Glu
1               5                   10                  15

Lys Cys Gly Leu Trp Phe Tyr Thr His Pro Leu Val Lys Leu Leu Phe
            20                  25                  30

Leu Arg Gln Arg Thr Arg Cys Lys Phe Phe Ser Leu Thr Glu Thr Pro
        35                  40                  45

Glu Asp Tyr Thr Leu Met Leu Asp Glu Glu Gly Phe Glu Glu Leu Pro
    50                  55                  60

Pro Ser Glu Phe Leu His Val Ala Glu Asn Thr Trp Arg Val Leu Asn
65                  70                  75                  80

Val Leu Ser Ser Gly Cys Ser Ser Asn Gly Ile Gln Thr Val Gly Val
                85                  90                  95

Thr Lys Ile Ala Lys Ser Val Ile Ala Pro Leu Ala Glu His Asn Val
            100                 105                 110

Ser Val Leu Met Leu Ser Thr Tyr Gln Thr Asp Tyr Ile Leu Val Arg
        115                 120                 125

Glu Asp Asp Leu Pro Val Val Phe His Thr Leu Asp Asp Leu Ser
    130                 135                 140

Ile Tyr Lys Glu Glu Asn Gly Ile Leu Val Pro Val Lys Pro Thr Glu
145                 150                 155                 160

Ala Arg Asn Thr Leu Lys Pro Arg Thr Leu Phe Asn Leu Thr Val His
                165                 170                 175

Pro Val Gln Ser Pro Gln Asn Gln Phe Cys Ile Leu Thr Met Asp Pro
            180                 185                 190

Asp Thr Leu Pro Ser Val Ser Thr Ile Leu Leu Asp Val Leu Phe Tyr
        195                 200                 205

Ser His Pro Phe Gln Lys Asp Thr Ala Ala Gly Ser Gln Asp Leu Gly
    210                 215                 220

Phe Phe His Phe Phe Ala Phe Ser Leu Ile Asp Gly Tyr Ile Ser Ile
225                 230                 235                 240

Val Met Asp Thr Lys Thr Gln Glu Lys Phe Pro Thr Asp Leu Leu Leu
                245                 250                 255

Thr Ser Ser Ser Gly Glu Leu Trp Arg Met Val Arg Ile Gly Gly Gln
            260                 265                 270

Pro Leu Gly Phe Asp Glu Cys Gly Ile Val Ala Gln Ile Ala Gly Pro
        275                 280                 285

Leu Ala Ala Ala Asp Ile Ser Ala Tyr Tyr Ile Ser Ser Tyr Asn Phe
    290                 295                 300

Asp His Ala Leu Val Pro Glu Glu Asp Ile Glu Asn Val Ile Ser Leu
305                 310                 315                 320

Leu His Gln Arg Gln Glu Ser Lys Thr
                325

<210> SEQ ID NO 29
<211> LENGTH: 331
<212> TYPE: PRT
<213> ORGANISM: Danio rerio

<400> SEQUENCE: 29

Met Asp Leu His Ile Leu Asp His Arg Leu Arg Val Thr Cys Ile Ser
1               5                   10                  15

Lys Ser Gly Leu Gln His Tyr Thr His Pro Leu Ile Lys Leu Ile Phe 20                  25                  30
Leu Arg Asn Arg Thr Arg Cys Lys Phe Phe Ser Leu Thr Glu Thr Pro
             35                  40                  45

Glu Asn Tyr Thr Val Val Leu Asp Glu Glu Gly Phe Lys Glu Leu His
     50                  55                  60

Pro Ser Glu His Val Gln Val Glu Gly Ser Thr Trp Leu Pro Leu Asn
 65                  70                  75                  80

Val Val Ser Asn Gly Asn Ala Ser Ser Ser Gln Ala Val Gly Val
                 85                  90                  95

Thr Lys Ile Ala Lys Ser Val Ile Ala Pro Leu Ala Glu Gln His Val
             100                 105                 110

Ser Val Phe Met Leu Ser Thr Tyr Gln Thr Asp Phe Ile Leu Val Arg
         115                 120                 125

Glu Lys Asp Leu Ser Val Val Glu Thr Leu Val Glu Glu Phe Asn
     130                 135                 140

Ile Phe Arg Glu Glu Gly Gly Glu Ser Val Pro Val His Ser Gln Asp
145                 150                 155                 160

Ser Cys Asn Gly Leu Gln Arg Asn Gly Arg Glu Val Pro His Ala Thr
                 165                 170                 175

Val His Pro Val Leu Ile Pro Glu Asn His Phe Cys Val Met Ser Leu
             180                 185                 190

Asp Pro Asp Thr Leu Pro Ala Ile Ala Thr Thr Leu Ile Asp Val Leu
         195                 200                 205

Phe Tyr Ser Asn Ser Pro Lys Glu Gly Ala Ser Val Asp Gln Asp Met
     210                 215                 220

Glu Cys Ile Lys Phe Phe Ser Phe Ser Leu Ile Asp Gly Tyr Val Ser
225                 230                 235                 240

Leu Val Met Asp Thr Asp Ala Gln Arg Gln Phe Pro Ala Asp Leu Leu
                 245                 250                 255

Phe Thr Ser Ser Ser Gly Glu Leu Trp Arg Met Val Arg Ile Gly Gly
             260                 265                 270

Gln Pro Leu Gly Phe Asp Glu Cys Gly Ile Val Ala Gln Ile Ser Gln
         275                 280                 285

Pro Leu Ala Asp Ser Asp Ile Ser Ala Tyr Tyr Ile Ser Thr Phe Ser
     290                 295                 300

Phe Asp His Ala Leu Val Pro Glu Glu Asp Ile Thr Ser Val Met Glu
305                 310                 315                 320

Met Leu Gln Thr Gln Arg Lys Glu Met Ser Ser
                 325                 330

<210> SEQ ID NO 30
<211> LENGTH: 329
<212> TYPE: PRT
<213> ORGANISM: Homo sapiens

<400> SEQUENCE: 30

Met Glu Leu His Ile Leu Glu His Arg Leu Gln Val Ala Ser Val Ala
1               5                   10                  15

Lys Glu Ser Ile Pro Leu Phe Thr Tyr Gly Leu Ile Lys Leu Ala Phe
             20                  25                  30

Leu Ser Ser Lys Thr Arg Cys Lys Phe Phe Ser Leu Thr Glu Thr Pro
         35                  40                  45

Glu Asp Tyr Thr Ile Ile Val Asp Glu Glu Gly Phe Leu Glu Leu Pro
     50                  55                  60

```
Ser Ser Glu His Leu Ser Val Ala Asp Ala Thr Trp Leu Ala Leu Asn
 65                  70                  75                  80

Val Val Ser Gly Gly Gly Ser Phe Ser Ser Gln Pro Ile Gly Val
                 85                  90                  95

Thr Lys Ile Ala Lys Ser Val Ile Ala Pro Leu Ala Asp Gln Asn Ile
            100                 105                 110

Ser Val Phe Met Leu Ser Thr Tyr Gln Thr Asp Phe Ile Leu Val Arg
        115                 120                 125

Glu Arg Asp Leu Pro Phe Val Thr His Thr Leu Ser Ser Glu Phe Thr
130                 135                 140

Ile Leu Arg Val Val Asn Gly Glu Thr Val Ala Ala Glu Asn Leu Gly
145                 150                 155                 160

Ile Thr Asn Gly Phe Val Lys Pro Lys Leu Val Gln Arg Pro Val Ile
                165                 170                 175

His Pro Leu Ser Ser Pro Ser Asn Arg Phe Cys Val Thr Ser Leu Asp
            180                 185                 190

Pro Asp Thr Leu Pro Ala Val Ala Thr Leu Leu Met Asp Val Met Phe
        195                 200                 205

Tyr Ser Asn Gly Val Lys Asp Pro Met Ala Thr Gly Asp Asp Cys Gly
210                 215                 220

His Ile Arg Phe Phe Ser Phe Ser Leu Ile Glu Gly Tyr Ile Ser Leu
225                 230                 235                 240

Val Met Asp Val Gln Thr Gln Arg Phe Pro Ser Asn Leu Leu Phe
                245                 250                 255

Thr Ser Ala Ser Gly Glu Leu Trp Lys Met Val Arg Ile Gly Gly Gln
            260                 265                 270

Pro Leu Gly Phe Asp Glu Cys Gly Ile Val Ala Gln Ile Ser Glu Pro
        275                 280                 285

Leu Ala Ala Ala Asp Ile Pro Ala Tyr Tyr Ile Ser Thr Phe Lys Phe
        290                 295                 300

Asp His Ala Leu Val Pro Glu Glu Asn Ile Asn Gly Val Ile Ser Ala
305                 310                 315                 320

Leu Lys Val Ser Gln Ala Glu Lys His
                325

<210> SEQ ID NO 31
<211> LENGTH: 329
<212> TYPE: PRT
<213> ORGANISM: Pan troglodytes

<400> SEQUENCE: 31

Met Glu Leu His Ile Leu Glu His Arg Leu Gln Val Ala Ser Val Ala
1               5                   10                  15

Lys Glu Ser Ile Pro Leu Phe Thr Tyr Gly Leu Ile Lys Leu Ala Phe
            20                  25                  30

Leu Ser Ser Lys Thr Arg Cys Lys Phe Phe Ser Leu Thr Glu Thr Pro
        35                  40                  45

Glu Asp Tyr Thr Ile Ile Val Asp Glu Glu Gly Phe Leu Glu Leu Pro
    50                  55                  60

Ser Ser Glu His Leu Ser Val Ala Asp Ala Thr Trp Leu Ala Leu Asn
65                  70                  75                  80

Val Val Ser Gly Gly Gly Ser Phe Ser Ser Gln Pro Ile Gly Val
                85                  90                  95

Thr Lys Ile Ala Lys Ser Val Ile Ala Pro Leu Ala Asp Gln Asn Ile
            100                 105                 110
```

-continued

```
Ser Val Phe Met Leu Ser Thr Tyr Gln Thr Asp Phe Ile Leu Val Arg
            115                 120                 125

Glu Arg Asp Leu Pro Phe Val Thr His Thr Leu Ser Ser Glu Phe Thr
130                 135                 140

Ile Leu Arg Val Val Asn Gly Glu Thr Val Ala Ala Glu Asn Leu Gly
145                 150                 155                 160

Ile Thr Asn Gly Phe Val Lys Pro Lys Leu Val Gln Arg Pro Val Ile
                165                 170                 175

His Pro Leu Ser Ser Pro Ser Asn Arg Phe Cys Val Thr Ser Leu Asp
                180                 185                 190

Pro Asp Thr Leu Pro Ala Val Ala Thr Leu Leu Met Asp Val Met Phe
                195                 200                 205

Tyr Ser Asn Gly Val Lys Asp Pro Met Ala Thr Gly Asp Asp Cys Gly
            210                 215                 220

His Ile Arg Phe Phe Ser Phe Ser Leu Ile Glu Gly Tyr Ile Ser Leu
225                 230                 235                 240

Val Met Asp Val Gln Thr Gln Gln Arg Phe Pro Ser Asn Leu Leu Phe
                245                 250                 255

Thr Ser Ala Ser Gly Glu Leu Trp Lys Met Val Arg Ile Gly Gly Gln
                260                 265                 270

Pro Leu Gly Phe Asp Glu Cys Gly Ile Val Ala Gln Ile Ser Glu Pro
            275                 280                 285

Leu Ala Ala Ala Asp Ile Pro Ala Tyr Tyr Ile Ser Thr Phe Lys Phe
290                 295                 300

Asp His Ala Leu Val Pro Glu Glu Asn Ile Asn Gly Val Ile Ser Ala
305                 310                 315                 320

Leu Lys Val Ser Gln Ala Glu Lys His
                325

<210> SEQ ID NO 32
<211> LENGTH: 332
<212> TYPE: PRT
<213> ORGANISM: Canis lupus familiaris

<400> SEQUENCE: 32

Met Pro Met Gly Cys Val Trp Arg Gly Lys Glu Gly Ala His Gly Gly
1               5                   10                  15

Pro Arg Gln Thr Arg Arg Ser His Leu Ser Arg Asn Pro Ala Gly Thr
                20                  25                  30

Ser Ile Cys Leu Gln Asn Tyr Glu Arg Cys Lys Phe Phe Ser Leu Thr
            35                  40                  45

Glu Thr Pro Glu Asp Tyr Thr Ile Ile Val Asp Glu Glu Gly Phe Leu
50                  55                  60

Glu Leu Pro Ser Ser Glu His Leu Ser Val Ala Asp Ala Thr Trp Leu
65                  70                  75                  80

Ala Leu Asn Val Val Ser Gly Gly Gly Ser Phe Ser Ser Ser Gln Pro
                85                  90                  95

Ile Gly Val Thr Lys Ile Ala Lys Ser Val Ile Ala Pro Leu Ala Asp
                100                 105                 110

Gln Asn Ile Ser Val Phe Met Leu Ser Thr Tyr Gln Thr Asp Phe Ile
            115                 120                 125

Leu Val Arg Glu Arg Asp Leu Pro Phe Val Thr His Thr Leu Ser Ser
130                 135                 140

Glu Phe Thr Ile Leu Arg Val Val Asn Gly Glu Thr Val Ala Ala Glu
```

```
145                 150                 155                 160
    Asn Leu Gly Ile Thr Asn Gly Phe Val Lys Pro Lys Met Val Gln Arg
                    165                 170                 175

Pro Val Ile His Pro Leu Ser Ser Pro Ser Asn Arg Phe Cys Val Thr
                180                 185                 190

Ser Leu Asp Pro Asp Thr Leu Pro Ala Val Ala Thr Leu Leu Met Asp
                195                 200                 205

Val Met Phe Tyr Ser Asn Gly Val Lys Asp Pro Met Ala Ala Gly Glu
            210                 215                 220

Asp Cys Gly His Ile Arg Phe Phe Ser Phe Ser Leu Ile Glu Gly Tyr
    225                 230                 235                 240

Ile Ser Leu Val Met Asp Val Gln Thr Gln Gln Arg Phe Pro Ser Asn
                    245                 250                 255

Leu Leu Phe Thr Ser Ala Ser Gly Glu Leu Trp Lys Met Val Arg Ile
                260                 265                 270

Gly Gly Gln Pro Leu Gly Phe Asp Glu Cys Gly Ile Val Ala Gln Ile
                275                 280                 285

Ser Glu Pro Leu Ala Ala Ala Asp Ile Pro Ala Tyr Tyr Ile Ser Thr
            290                 295                 300

Phe Lys Phe Asp His Ala Leu Val Pro Glu Glu Asn Ile Ser Ala Val
    305                 310                 315                 320

Ile Ser Ala Leu Lys Val Ser Gln Ala Glu Lys His
                    325                 330

<210> SEQ ID NO 33
<211> LENGTH: 329
<212> TYPE: PRT
<213> ORGANISM: Bos taurus

<400> SEQUENCE: 33

Met Glu Leu His Ile Leu Glu His Arg Leu Gln Val Ala Ser Val Ala
    1               5                   10                  15

Lys Glu Ser Ile Pro Leu Phe Thr Tyr Gly Leu Ile Lys Leu Ala Phe
                    20                  25                  30

Leu Ser Ser Lys Thr Arg Cys Lys Phe Phe Ser Leu Thr Glu Thr Pro
                35                  40                  45

Glu Asp Tyr Thr Ile Ile Val Asp Glu Glu Gly Phe Leu Glu Leu Pro
        50                  55                  60

Ser Ser Glu His Leu Ser Val Ala Asp Ala Thr Trp Leu Ala Leu Asn
    65                  70                  75                  80

Val Val Ser Gly Gly Ser Phe Ser Ser Ser Gln Pro Ile Gly Val
                    85                  90                  95

Thr Lys Ile Ala Lys Ser Val Ile Ala Pro Leu Ala Asp Gln Asn Ile
                100                 105                 110

Ser Val Phe Met Leu Ser Thr Tyr Gln Thr Asp Phe Ile Leu Val Arg
                115                 120                 125

Glu Arg Asp Leu Pro Phe Val Thr His Thr Leu Ser Ser Glu Phe Thr
        130                 135                 140

Ile Leu Arg Val Val Asn Gly Glu Thr Val Ala Ala Glu Asn Leu Gly
    145                 150                 155                 160

Ile Thr Asn Gly Phe Val Lys Pro Lys Met Val Gln Arg Pro Val Ile
                    165                 170                 175

His Pro Leu Ser Ser Pro Ser Asn Arg Phe Cys Val Thr Ser Leu Asp
                180                 185                 190
```

```
Pro Asp Thr Leu Pro Thr Val Ala Thr Leu Met Asp Val Met Phe
        195                 200                 205

Tyr Ser Asn Gly Val Lys Asp Pro Leu Ala Ser Gly Asp Asp Cys Asp
210                 215                 220

His Ile Arg Phe Phe Ser Phe Ser Leu Ile Glu Gly Tyr Ile Ser Leu
225                 230                 235                 240

Val Met Asp Val Gln Thr Gln Gln Arg Phe Pro Ser Asn Leu Leu Phe
                245                 250                 255

Thr Ser Ala Ser Gly Glu Leu Trp Lys Met Val Arg Ile Gly Gly Gln
                260                 265                 270

Pro Leu Gly Phe Asp Glu Cys Gly Ile Val Ala Gln Ile Ser Glu Pro
                275                 280                 285

Leu Ala Ala Ala Asp Ile Pro Ala Tyr Tyr Ile Ser Thr Phe Lys Phe
                290                 295                 300

Asp His Ala Leu Val Pro Glu Glu Asn Ile Asn Gly Val Ile Ser Ala
305                 310                 315                 320

Leu Lys Val Ser Gln Ala Glu Lys His
                325

<210> SEQ ID NO 34
<211> LENGTH: 329
<212> TYPE: PRT
<213> ORGANISM: Mus musculus

<400> SEQUENCE: 34

Met Glu Leu His Ile Leu Glu His Arg Leu Gln Val Ala Ser Val Ala
1               5                   10                  15

Lys Glu Ser Ile Pro Leu Phe Thr Tyr Gly Leu Ile Lys Leu Ala Phe
                20                  25                  30

Leu Ser Ser Lys Thr Arg Cys Lys Phe Phe Ser Leu Thr Glu Thr Pro
                35                  40                  45

Glu Asp Tyr Thr Ile Ile Val Asp Glu Glu Gly Phe Leu Glu Leu Pro
50                  55                  60

Ser Ser Glu His Leu Ser Val Ala Asp Ala Thr Trp Leu Ala Leu Asn
65                  70                  75                  80

Val Val Ser Gly Gly Gly Ser Phe Ser Ser Gln Pro Ile Gly Val
                85                  90                  95

Thr Lys Ile Ala Lys Ser Val Ile Ala Pro Leu Ala Asp Gln Asn Ile
                100                 105                 110

Ser Val Phe Met Leu Ser Thr Tyr Gln Thr Asp Phe Ile Leu Val Arg
                115                 120                 125

Glu Arg Asp Leu Pro Phe Val Thr His Thr Leu Ser Ser Glu Phe Thr
130                 135                 140

Ile Leu Arg Val Val Asn Gly Glu Thr Val Ala Ala Glu Asn Leu Ser
145                 150                 155                 160

Phe Thr Asn Gly Phe Val Lys Pro Lys Met Val Gln Arg Pro Val Ile
                165                 170                 175

His Pro Leu Ser Ser Pro Ser Asn Arg Phe Cys Val Thr Ser Leu Asp
                180                 185                 190

Pro Asp Thr Leu Pro Ala Val Ala Thr Leu Leu Met Asp Val Met Phe
                195                 200                 205

Tyr Ser Asn Gly Val Lys Asp Pro Met Ala Ala Ser Asp Asp Cys Gly
210                 215                 220

His Ile Arg Phe Phe Ser Phe Ser Leu Ile Glu Gly Tyr Ile Ser Leu
225                 230                 235                 240
```

```
Val Met Asp Val Gln Thr Gln Gln Arg Phe Pro Ser His Leu Leu Phe
                245                 250                 255

Thr Ser Ala Ser Gly Glu Leu Trp Lys Met Val Arg Ile Gly Gly Gln
            260                 265                 270

Pro Leu Gly Phe Asp Glu Cys Gly Ile Val Ala Gln Ile Ser Glu Pro
        275                 280                 285

Leu Ala Ala Asp Ile Pro Ala Tyr Tyr Ile Ser Thr Phe Lys Phe
    290                 295                 300

Asp His Ala Leu Val Pro Glu Glu Asn Ile Ser Gly Val Ile His Ala
305                 310                 315                 320

Leu Lys Val Ser Gln Ala Gly Lys His
                325

<210> SEQ ID NO 35
<211> LENGTH: 329
<212> TYPE: PRT
<213> ORGANISM: Xenopus tropicalis

<400> SEQUENCE: 35

Met Glu Leu His Ile Leu Glu His Arg Leu Lys Val Ala Ser Ile Ala
1               5                   10                  15

Lys Glu Asn Ile Gln Leu Phe Thr Tyr Gly Leu Ile Lys Leu Ala Phe
                20                  25                  30

Leu Ser Ser Lys Thr Arg Cys Lys Phe Phe Ser Leu Thr Glu Thr Pro
            35                  40                  45

Glu Asp Tyr Thr Ile Ile Val Asp Glu Glu Gly Phe Leu Glu Leu Pro
    50                  55                  60

Ser Ser Glu His Leu Ser Val Ala Asp Ala Thr Trp Leu Ala Leu Asn
65                  70                  75                  80

Val Val Ser Gly Gly Ser Ser Ser Ser Gln Pro Ile Gly Val
                85                  90                  95

Thr Lys Ile Ala Lys Ser Val Ile Ala Pro Leu Ala Asp Gln Asn Ile
                100                 105                 110

Ser Val Phe Met Leu Ser Thr Tyr Gln Thr Asp Phe Ile Leu Val Arg
            115                 120                 125

Glu Arg Asp Leu Pro Phe Val Met His Thr Leu Ala Ala Glu Phe Thr
    130                 135                 140

Ile Leu Gln Val Val Asn Gly Glu Thr Val Ala Ala Asp Asn Leu Gly
145                 150                 155                 160

Val Thr Asn Gly Phe Val Lys Pro Lys Leu Val Gln Arg Pro Val Ile
                165                 170                 175

His Pro Leu Ser Ser Pro Ser Asn Met Phe Cys Val Thr Ser Leu Asp
            180                 185                 190

Pro Tyr Thr Leu Pro Thr Val Thr Thr Leu Leu Met Asp Val Met Phe
    195                 200                 205

Tyr Ser Asn Gly Val Lys Asp Ser Val Val Gly Ser Glu Glu Pro Gly
    210                 215                 220

His Ile Arg Phe Phe Ser Phe Ser Leu Ile Glu Gly Tyr Ile Ser Leu
225                 230                 235                 240

Val Met Asp Val Gln Thr Gln Gln Arg Phe Pro Ser Asn Leu Leu Phe
                245                 250                 255

Thr Ser Ala Ser Gly Glu Leu Trp Lys Met Val Arg Ile Gly Gly Gln
            260                 265                 270

Pro Leu Gly Phe Asp Glu Cys Gly Ile Val Ala Gln Ile Ser Glu Pro
```

```
            275                 280                 285
Leu Ala Ala Asp Ile Pro Ala Tyr Tyr Ile Ser Thr Phe Lys Phe
    290                 295                 300
Asp His Ala Leu Val Pro Glu Glu Asn Ile Asn Gly Val Ile Asn Ala
305                 310                 315                 320
Leu Gln Val Ser Gln Ala Glu Lys His
                325

<210> SEQ ID NO 36
<211> LENGTH: 329
<212> TYPE: PRT
<213> ORGANISM: Danio rerio

<400> SEQUENCE: 36

Met Glu Leu His Ile Leu Glu His Ser Leu Lys Val Ala Ser Ile Ala
1               5                   10                  15
Lys Glu Gly Ile Gln Ile Cys Thr His Gly Leu Ile Lys Leu Ala Phe
                20                  25                  30
Leu Pro Ser Lys Thr Arg Cys Lys Phe Phe Ser Leu Thr Glu Thr Pro
            35                  40                  45
Glu Asp Tyr Thr Ile Ile Val Asp Glu Asp Gly Phe Lys Glu Leu Pro
    50                  55                  60
Glu Ser Glu Tyr Leu Ser Val Ala Asp Ala Thr Trp Leu Ala Leu Asn
65                  70                  75                  80
Val Val Ser Gly Gly Ser Ala Thr Ser Ser Gln Pro Ile Gly Val
                85                  90                  95
Thr Lys Ile Ala Lys Ser Val Ile Ala Pro Leu Ala Asp His Asn Ile
                100                 105                 110
Ser Val Phe Met Leu Ser Thr Tyr Gln Thr Asp Phe Ile Leu Val Arg
            115                 120                 125
Glu Arg Asp Leu Pro Met Val Met His Thr Leu Ser Ser Glu Phe Thr
    130                 135                 140
Leu Leu Arg Val Val Asn Gly Glu Ala Val Ala Ala Asn Ser Thr Gly
145                 150                 155                 160
Val Thr Asn Gly Phe Val Lys Pro Lys Leu Val Pro Arg Pro Ile Ile
                165                 170                 175
His Pro Leu Ser Ser Pro Ser Asn Met Phe Cys Val Thr Ser Leu Asp
            180                 185                 190
Pro Asp Thr Leu Pro Ser Val Ala Thr Leu Leu Met Asp Val Met Phe
    195                 200                 205
Tyr Ser Gly Gly Ala Lys Glu Ala Ala Gly Gln Ser Glu Asp Ser Cys
    210                 215                 220
His Ile Arg Phe Phe Ser Phe Ser Leu Ile Glu Gly Tyr Ile Ser Leu
225                 230                 235                 240
Val Met Asp Glu Gln Thr Thr Arg Arg Phe Pro Asn Asn Val Leu Phe
                245                 250                 255
Thr Ser Ala Ser Gly Glu Leu Trp Lys Met Val Arg Ile Gly Gly Gln
            260                 265                 270
Pro Leu Gly Phe Asp Glu Cys Gly Ile Val Ala Gln Ile Ser Glu Pro
    275                 280                 285
```

-continued

```
Leu Ala Thr Ala Asp Ile Pro Ala Tyr Tyr Ile Ser Thr Phe Lys Phe
    290             295             300

Asp His Ala Leu Val Pro Glu Glu Asn Ile Gln Ser Val Ile Gly Ala
305             310             315             320

Leu Arg Thr Asn Glu Ser Thr Gly Gln
                325
```

METHODS OF IDENTIFYING MODULATORS OF CASTOR1-GATOR2 INTERACTION AND USE OF SAME TO MODULATE MTORC1

RELATED APPLICATIONS

This application is a national stage filing under 35 U.S.C. 371 of International Application No. PCT/US2016/068995, filed Dec. 28, 2016, which claims the benefit of U.S. Provisional Application Ser. No. 62/271,997, filed Dec. 28, 2015, and U.S. Provisional Application Ser. No. 62/278,415, filed Jan. 13, 2016, the contents of which are hereby incorporated by reference in its entirety. International Application No. PCT/US2016/068995 was published under PCT Article 21(2) in English.

GOVERNMENT SUPPORT

This invention was made with government support under Grant Nos. R01CA103866, AI47389 and HG006673 awarded by the National Institutes of Health and Grant No. W81XWH-07-0448 awarded by the Department of Defense. The government has certain rights in the invention.

BACKGROUND OF THE INVENTION

Arginine is a conditionally essential amino acid with many metabolic and regulatory roles, serving as a proteogenic amino acid, as well as a precursor for critical molecules such as nitric oxide, creatine, and glutamate (Wu and Morris, 1998). Arginine regulates key aspects of mammalian physiology, including insulin release, intestinal stem cell migration, and neonatal growth (Ban et al., 2004; Floyd et al., 1966; Rhoads et al., 2006; Yao et al., 2008). These effects stem at least in part from the ability of arginine to activate mTORC1, a master growth controller that integrates diverse environmental inputs to coordinate many anabolic and catabolic processes in cells (Ban et al., 2004; Dibble and Manning, 2013; Efeyan et al., 2012; Hara, 1998).

The lysosome is a critical organelle for mTORC1 activation, and amino acids promote the translocation of mTORC1 to its surface where its kinase activator Rheb, a small GTPase, resides (Buerger et al., 2006; Dibble et al., 2012; Menon et al., 2014; Saito et al., 2005; Sancak et al., 2008). Necessary for this recruitment are the Rag GTPases, which form heterodimeric complexes comprised of RagA or RagB bound to RagC or RagD (Hirose et al., 1998; Sancak et al., 2008; Schurmann et al., 1995; Sekiguchi et al., 2001). Amino acid availability controls the nucleotide state of the Rags, and this regulation depends on a complex interplay between multiple distinct factors, including Ragulator, which serves as a lysosomal scaffold for RagA/B (Bar-Peled et al., 2012; Sancak et al., 2010); FLCN/FNIP2, a GAP for RagC/D (Petit et al., 2013; Tsun et al., 2013); and GATOR1, a GAP for RagA/B and a critical negative regulator of the mTORC1 pathway (Bar-Peled et al., 2013). The GATOR2 complex, which has five subunits (mios, WDR24, WDR59, sec13, seh1L), acts upstream or parallel to GATOR1 and is a key positive regulator of the mTORC1 pathway, although its molecular function is currently unknown (Bar Peled et al., 2013).

The proteins that sense amino acids and signal to the Rag GTPases were elusive until recently. We identified Sestrin2 as a cytosolic leucine sensor and SLC38A9 as a putative lysosomal arginine sensor for the mTORC1 pathway (Rebsamen et al., 2015; Saxton et al., 2015; Wang et al, 2015; Wolfson et al., 2015). While Sestrin2 interacts with GATOR2 to inhibit mTORC1 signaling in the absence of leucine, SLC38A9 forms a supercomplex with Ragulator and is necessary for transmitting arginine, but not leucine, sufficiency to mTORC1 (Chantranupong et al, 2014; Jung et al., 2015; Lynch et al., 2000; Rebsamen et al., 2015; Saxton et al., 2015; Wang et al., 2015; Wolfson et al., 2015; Zoncu et al., 2011). Despite these advances, in human cells lacking SLC38A9, arginine starvation still inhibits mTORC1 (Wang et al., 2015), suggesting that our understanding of how arginine is sensed is incomplete and how arginine deprivation represses mTORC1 is unknown.

SUMMARY OF THE INVENTION

The present invention demonstrates that CASTOR1, a previously uncharacterized protein, functions in parallel with SLC38A9 to regulate mTORC1 in response to arginine. CASTOR1 forms a homodimer and heterodimerizes with CASTOR2, also a previously unstudied protein, and both complexes interact with GATOR2 to negatively regulate mTORC1 activity. Arginine disrupts this interaction by binding directly to CASTOR1. Activation of the mTORC1 pathway by arginine requires the arginine-binding capacity of CASTOR1. Thus, CASTOR1 is an arginine sensor for the mTORC1 pathway.

In some aspects, the disclosure provides a method of identifying a test compound as an activator of mTORC1 activity. In one aspect of these embodiments, the method comprises the steps of:
 a) providing a mixture comprising:
  (i) a first polypeptide comprising a GATOR2-binding fragment of CASTOR1, or a polypeptide having at least 80% homology to CASTOR1 that retains the ability to bind GATOR2; and
  (ii) a second polypeptide or protein complex comprising a CASTOR1-binding fragment of a GATOR2 complex, or a polypeptide or protein complex having at least 80% homology to a GATOR2 complex that retains the ability to bind to CASTOR1,
 under conditions that allow the first polypeptide to associate with the second polypeptide or protein complex;
 b) incubating the mixture of a) with the test compound;
 c) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

In some aspects, the disclosure provides a method of identifying a test compound as an inhibitor of mTORC1 activity. In one aspect of these embodiments, the method comprises the steps of:
 a) providing a mixture comprising:
  (i) a first polypeptide comprising a GATOR2-binding fragment of CASTOR1, or a polypeptide having at least 80% homology to CASTOR1 that retains the ability to bind GATOR2; and
  (ii) a second polypeptide or protein complex comprising a CASTOR1-binding fragment of a GATOR2 complex, or a polypeptide or protein complex having at least 80% homology to a GATOR2 complex that retains the ability to bind to CASTOR1,
 under conditions that prevent the first polypeptide from associating with the second polypeptide or protein complex;

b) incubating the mixture of a) with the test compound;
c) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

In other embodiments, the invention provides a method of agonizing mTORC1 activity in a cell by contacting the cell with an agent that reduces or antagonizes the interaction of CASTOR1 with a GATOR2 complex.

In other embodiments, the invention provides a method of agonizing (e.g., maintaining or increasing) mTORC1 activity in a cell by contacting the cell with an agent that reduces or antagonizes the interaction of CASTOR1 with a GATOR2 complex.

In still other embodiments, the invention provides method of treating a disease, condition or disorder in a subject who would benefit from increased mTORC1 activity comprising the step of administering to the subject an agent that reduces or antagonizes the interaction of CASTOR1 with a GATOR2 complex.

In other embodiments, the invention provides a method of decreasing mTORC1 activity in a cell by contacting the cell with an agent that induces or increases the interaction of CASTOR1 with a GATOR2 complex.

In still other embodiments, the invention provides a method of treating a disease, condition or disorder in a subject who would benefit from decreasing mTORC1 activity comprising the step of administering to the subject an agent that induces or increases the interaction of CASTOR1 with a GATOR2 complex.

In other embodiments, the invention provides a method of identifying a test compound as a modulator of mTORC1 by determining if the test compound can induce or increase the affinity of CASTOR1 for arginine. In one aspect of these embodiments, the method comprises the steps of:
a. providing a mixture comprising:
   i. a CASTOR1 polypeptide, or a polypeptide having at least 80% homology to CASTOR1 that retains the ability to bind arginine; and
   ii. arginine, under conditions that allow arginine to bind to the polypeptide;
b. incubating the mixture of a) with the test compound; and
c. determining whether the amount of arginine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In still other embodiments, the invention provides a method of identifying a test compound as a modulator of mTORC1 by determining if the test compound can induce or increase the affinity of CASTOR1 for arginine comprising the steps of:
a. providing a mixture comprising:
   i. a polypeptide comprising an arginine binding fragment of CASTOR1, or a polypeptide having at least 80% homology to CASTOR1 that retains the ability to bind arginine; and
   ii. the test compound;
b. incubating the mixture of a) with arginine under conditions that allow arginine to bind to the polypeptide; and
c. determining whether the amount of arginine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In other embodiments, the invention provides method of agonizing (e.g., maintaining or increasing) mTORC1 activity in a cell comprising the step of contacting the cell with an agent that increases the binding of arginine to CASTOR1.

In other embodiments, the invention provides a method of treating a disease, condition, or disorder in a subject who would benefit from increased mTORC1 activity comprising the step of administering to the subject an agent that increases the binding of arginine to CASTOR1.

In still other embodiments, the invention provides a method of decreasing mTORC1 activity in a cell comprising the step of contacting the cell with an agent that decreases the binding of arginine to CASTOR1.

In other embodiments, the invention provides a method of treating a disease, condition or disorder in a subject who would benefit from decreased mTORC1 activity comprising the step of administering to the subject an agent that decreases the binding of arginine to CASTOR1.

The above discussed, and many other features and attendant advantages of the present inventions will become better understood by reference to the following detailed description of the invention.

BRIEF DESCRIPTION OF THE DRAWINGS

FIG. 1A, FIG. 1B, FIG. 1C and FIG. 1D depict CASTOR1 and CATOR2 are ACT domain-containing proteins that interact with GATOR2. FIG. 1A is a schematic showing endogenous GATOR2, FAM164A, and CASTOR2 co-immunoprecipitate with stably expressed CASTOR1. The schematic is adapted from the BioPlex database (Huttlin et al., 2015). Solid blue lines denote proteins that were detected by mass spectrometric analysis of CASTOR1 immunoprecipitates, and dashed purple lines indicate interactions between GATOR2 subunits that were present in Bioplex. FIG. 1B is a schematic showing alignment of human CASTOR1 and CASTOR2 proteins with annotated ACT domains. FIG. 1C shows ACT domains of CASTOR1 and CASTOR2 display sequence similarity with the ACT domains of fungal aspartate kinases and putative amino acid binding proteins in bacteria. Amino acid positions are colored from white to blue in order of increasing sequence identity. The red star denotes the positions of the 1280 residue in CASTOR1. FIG. 1D shows recombinant CASTOR1 and CASTOR2 co-immunoprecipitate endogenous GATOR2, as detected by the presence of mios. Anti-HA immunoprecipitates and lysates were prepared from HEK-293T cells cotransfected with the indicated cDNAs in expression vectors. Cell lysates and immunoprecipitates were analyzed by immunoblotting for levels of indicated proteins. HA-metap2 served as a negative control.

FIG. 2A shows recombinant CASTOR1 and CAS- TOR2 coimmunoprecipitate both themselves and each other. HEK-293T cells were cotransfected with the indicated cDNAs in expression vectors and cell lysates and anti-HA immunoprecipitates were analyzed by immunoblotting for the indicated proteins as in FIG. 1D. FIG. 2B shows recombinant CASTOR2 coimmunoprecipitates endogenous CASTOR1. HEK-293T cells were cotransfected with the indicated cDNAs in expression vectors and anti-HA immunoprecipitates were collected and analyzed as in FIG. 1D. The arrow denotes the band corresponding to CASTOR1. FIG. 2C shows recombinant CASTOR1 coimmunoprecipitates endogenous CASTOR2. HEK-293T cells were cotransfected with the indicated cDNAs in expression vectors and anti-HA immunoprecipitates were collected and analyzed as in (2A). FIG. 2D shows CASTOR1 and CASTOR2 are present in approximately equal ratios within the heterodimeric complex. SDS-polyacrylamide gel electrophoresis (PAGE), followed by Coomassie blue staining, was used to analyze the indicated protein preparations from HEK-293T cells. The asterisk denotes a common protein contaminant present in these purifications.

FIG. 3A shows amino acids differentially regulate the interaction of GATOR2 with the three CASTOR complexes. HEK-293T cells cotransfected with the indicated cDNAs were deprived of amino acids for 50 min or starved and restimulated with amino acids for 10 min. Anti-HA immunoprecipitates and cell lysates were analyzed by immunoblotting for levels of the indicated proteins. FIG. 3B shows endogenous CASTOR1, but not CASTOR2, associates with GATOR2 in an amino acid-sensitive manner. A HEK-293T cell line expressing endogenously FLAG-tagged WDR59 was treated as in (3A) and anti-FLAG immunoprecipitates were analyzed by immunoblotting for the indicated proteins. FIG. 3C shows deprivation of arginine, but not leucine, promotes the interaction between the CASTOR1 homodimer and the endogenous GATOR2. Cells were deprived of leucine, arginine, or all amino acids for 50 min, and restimulated for 10 min with the respective amino acids where indicated. Anti-HA immunoprecipitates were prepared and analyzed as in (3A). FIG. 3D shows arginine disrupts the interaction between GATOR2 and CASTOR1-containing dimers in vitro. Anti-HA immunoprecipitates were prepared from HEK-293T cells expressing the indicated cDNAs and deprived of amino acids for 50 min. Indicated amino acids were added directly to the immunoprecipitates, which after re-washing, were analyzed as in (3A). FIG. 3E shows arginine dose-dependently disrupts the interaction between GATOR2 and CASTOR1-containing dimers in vitro. The experiment was performed and analyzed as in (3D), except using the indicated concentrations of arginine. FIG. 3F shows arginine regulates the interaction between the ACT domains of CASTOR1 but not CASTOR2 in cells. HEK-293T cells cotransfected with the indicated cDNAs in expression vectors were either deprived of arginine in the cell media for 50 min or starved and restimulated with arginine for 10 min. Anti-HA immunoprecipitates were prepared and analyzed as in (3A).

FIG. 4A shows radiolabeled arginine, but not radiolabeled leucine or lysine, binds to CASTOR1 homodimers. FLAG-immunoprecipitates were prepared from HEK-293T cells cotransfected with the indicated cDNAs, and binding assays were performed with these immunoprecipitates as described in the methods. Unlabelled amino acids were added where indicated. Values are mean±SD of three technical replicates from one representative experiments (n.s., not significant). FIG. 4B shows arginine binds to CASTOR1-containing homo- and heterodimers, but not the CASTOR2 homodimer. FLAG immunoprecipitates of the indicated complexes were prepared from HEK-293T cells and analyzed as in (4A). Equal volumes of eluants from immunoprecipitates of the denoted complexes were loaded and analyzed in SDS-Page, followed by Coomassie blue staining. FIG. 4C shows arginine hinds to bacterially produced CASTOR1-containing complexes, but not the CASTOR2 homodimer or the control protein Sestrin2. Proteins purified from bacteria were analyzed as in (4A) and (4B). FIG. 4D shows arginine binds to the CASTOR1 homodimer with a dissociation constant of 34.8 µM. Binding assays were performed as in (4A) with the indicated concentrations of unlabeled arginine. A representative experiment is shown, and each point represents the mean±SD for three experiments. The $K_d$ was calculated from four experiments. FIG. 4E shows arginine binds to the CASTOR1-CASTOR2 heterodimer with a dissociation constant of 24.2 µM. FLAG-immunoprecipitates were prepared from HEK-293T cells and analyzed as in (4). FIG. 4F shows the concentration of arginine that half-maximally activates the mTORC1 pathway correlates with the concentration of arginine that disrupts half of the complexes of GATOR2 and CASTOR1 homodimers. HEK-293T cells were transfected with the indicated cDNAs and immunoprecipitates and lysates analyzed as in FIG. 3C.

FIG. 5A shows transient overexpression of recombinant CASTOR2 and CASTOR1 inhibits mTORC1 activation in response to amino acids. HEK-293T cells were cotransfected with the indicated cDNAs. Cells were treated as in FIG. 3A and anti-FLAG immunoprecipitates analyzed by immunoblotting for the indicated proteins. FIG. 5B shows RNAi-mediated depletion of CASTOR1 in HEK-293T cells renders the mTORC1 pathway partially insensitive to arginine deprivation. HEK-293T cells stably expressing the indicated shRNAs were starved of arginine in the cell media for 50 min or starved and restimulated with arginine for 10 min. Lysates were analyzed via immunoblotting for the indicated proteins and phosphorylation states. FIG. 5C shows CRISPR/Cas9 mediated depletion of CASTOR1 in HEK-293T cells confers resistance of the mTORC1 pathway to arginine deprivation. HEK-293T cells stably coexpressing Cas9 with the indicated guide RNAs were treated as in (5B) and lysates were analyzed by immunoblotting for indicated proteins. FIG. 5D depicts loss of CASTOR2 slightly increases mTORC1 activity in response to arginine. HEK-293T cells stably expressing the indicated shRNAs were treated as in (5B) and lysates were analyzed by immunoblotting for indicated proteins. The normalized phosphorylated S6K1 signal under arginine stimulation for shCASTOR2_1 and shCASTOR2_2 expressing cells is 1.4 fold and 1.1 fold of shGFP expressing cells, respectively, as quantified with ImageJ. FIG. 5E shows CASTOR1 and SLC38A9 likely function in parallel to signal arginine availability to the mTORC1 pathway. Wild type of SLC38A9 knockout HEK-293T cells expressing the indicated shRNAs were treated as in (5B) and lysates were analyzed by immunoblotting for indicated proteins.

FIG. 6A shows CASTOR1 1280A mutant does not bind arginine. Binding assays were performed with FLAG immunoprecipitates of the indicated complexes as in FIG. 4A. FIG. 6B shows arginine does not regulate the interaction of CASTOR1 1280A with GATOR2. HEK-293T cells cotransfected with the indicated cDNAs in expression vectors were treated as in FIG. 5B and anti-HA immunoprecipitates were analyzed by immunoblotting for levels of the indicated proteins. FIG. 6C depicts reintroduction of the CASTOR1 1280A mutant into CASTOR1 knockdown cells renders the mTORC1 pathway unable to sense the presence of arginine. HEK-293T cells stably expressing the indicated shRNAs and cDNA constructs were treated as in FIG. 5B and lysates analyzed by immunoblotting for indicated proteins. FIG. 6D is a model depicting how the cytosolic and lysosomal amino acid inputs impinge on CASTORs, Sestrins, and SLC38A9 to regulate mTORC1 activity.

FIG. 7A, FIG. 7B, FIG. 7C, FIG. 7D, FIG. 7E and FIG. 7F depicts CASTOR1 and CASTOR2 homologs are present in vertebrates and invertebrates, and the CASTORs and Sestrins bind to distinct sites on GATOR2. FIG. 7A shows CASTOR1 and CASTOR2 are lowly expressed in most human tissues. mRNA expression data was obtained from GTex. FIG. 7B and FIG. 7C shows the CASTOR1 (FIG. 7B) and CASTOR2 (FIG. 7C) proteins are highly conserved in vertebrates. Sequence alignments are colored with respect to sequence identity as in FIG. 1C. The first and second ACT domains are annotated above the alignment with blue and orange bars, respectively. The red star denotes the position of the 1280 residue in CASTOR1. FIG. 7D shows CASTOR1 and CASTOR2 homologs are present in invertebrates and fungi, but not in S. cerevisiae and S. pombe. The sequence alignment is annotated as in (7B). FIG. 7E depicts the GATOR2 components WDR24, mios, and seh1L form a minimal complex that is sufficient to co-immunoprecipitate CASTOR1. HEK-293T cells were cotransfected with the indicated cDNAs, and anti-FLAG immunoprecipitates were analyzed as in FIG. 1D. FIG. 7F shows expression of CASTOR2, but not of Sestrin2, displaces CASTOR1 from GATOR2, HEK-293T cells were cotransfected with the indicated cDNAs, and anti-FLAG immunoprecipitates were analyzed as in FIG. 1D.

FIG. 8A, FIG. 8B, FIG. 8C and FIG. 8D depicts FAM164A does not interact with CASTOR1, CASTOR2, or GATOR2. FIG. 8A depicts validation of the anti-serum used to detect endogenous CASTOR2. Lysates were prepared from HEK-293T lines stably expressing the indicated shRNAs and analyzed by immunoblotting for levels of indicated proteins. FIG. 8B depicts validation of the anti-serum used to detect endogenous CASTOR1. Lysates were prepared from HEK-293T stably lines expressing the indicated shRNAs and analyzed as in (8C). The arrow denotes the band corresponding to endogenous CASTOR1. FIG. 8C shows recombinant FAM164A does not coimmunoprecipitate CASTOR2 or CASTOR1. HEK-293T cells were cotransfected with the indicated cDNAs in expression vectors, starved of all amino acids for 50 minutes, and anti-HA immunoprecipitates were analyzed as in FIG. 1D. FIG. 8D shows FAM164A does not copurify endogenous GATOR2. HEK-293T cells were cotransfected with the indicated cDNAs in expression vectors, starved of all amino acids for 50 minutes, and anti-HA immunoprecipitates were analyzed as in FIG. 1D.

FIG. 9A depicts RNAi-mediated depletion of CASTOR2 does not alter the level of endogenous GATOR2 that co-immunoprecipitates with recombinant CASTOR1. HEK-293T cells cotransfected with the indicated cDNAs and stably expressing the indicated shRNAs were deprived of amino acids in the cell media for 50 min. Anti-HA immunoprecipitates were analyzed by immunoblotting for the indicated proteins. FIG. 9B shows amino acids disrupt the interaction of GATOR2 with endogenous CASTOR1, but not CASTOR2. HEK-293T cells were starved or restimulated with amino acids, and immunoprecipitates were prepared from these cells using an antibody directed against GSK3β or WDR24. Immunoprecipitates were analyzed by immunoblotting for the indicated proteins. FIG. 9C shows loss of CASTOR1 abrogates the slight amino acid regulation of the interaction of CASTOR2 homodimers with GATOR2. Stable expression lines of HEK-293T cells stably expressing the denoted proteins were cotransfected with the indicated cDNAs and treated as in FIG. 3A. Anti-HA immunoprecipitates were analyzed by immunoblotting for the levels of indicated proteins. FIG. 9D depicts deprivation of arginine, but not leucine, is sufficient to promote the association of endogenous GATOR2 with recombinant CASTOR1-CASTOR2 heterodimers. HEK-293T cells cotransfected with the indicated cDNAs were treated and analyzed as in FIG. 3C. FIG. 9E shows arginine disrupts the interaction between GATOR2 and the CASTOR1-CASTOR2 heterodimer in ice-cold detergent lysates of amino acid-starved cells. Anti-HA immunoprecipitates were prepared and analyzed as in FIG. 3E.

FIG. 11A depicts reintroduction of CASTOR1 into CASTOR1 knockdown cells rescues the ability of the mTORC1 pathway to respond to arginine deprivation. HEK-293T cells stably expressing the indicated shRNAs and cDNA constructs were treated as in FIG. 3B and lysates were analyzed by immunoblotting for indicated proteins. FIG. 11B shows CRISPR/Cas9 mediated depletion of CASTOR1 in HEC59 cells confers resistance of the mTORC1 pathway to arginine deprivation. HEC59 cells stably expressing Cas9 with the indicated guide RNAs were treated as in FIG. 3B and lysates were analyzed by immunoblotting for indicated proteins. FIG. 11C shows RNAi-mediated depletion of CASTOR2 increases mTORC1 activity in response to arginine in cells depleted of CASTOR1. HEK-293T cells stably expressing the indicated shRNAs were treated as in FIG. 3B and lysates were analyzed by immunoblotting for indicated proteins.

DETAILED DESCRIPTION OF THE INVENTION

Figure 1A:
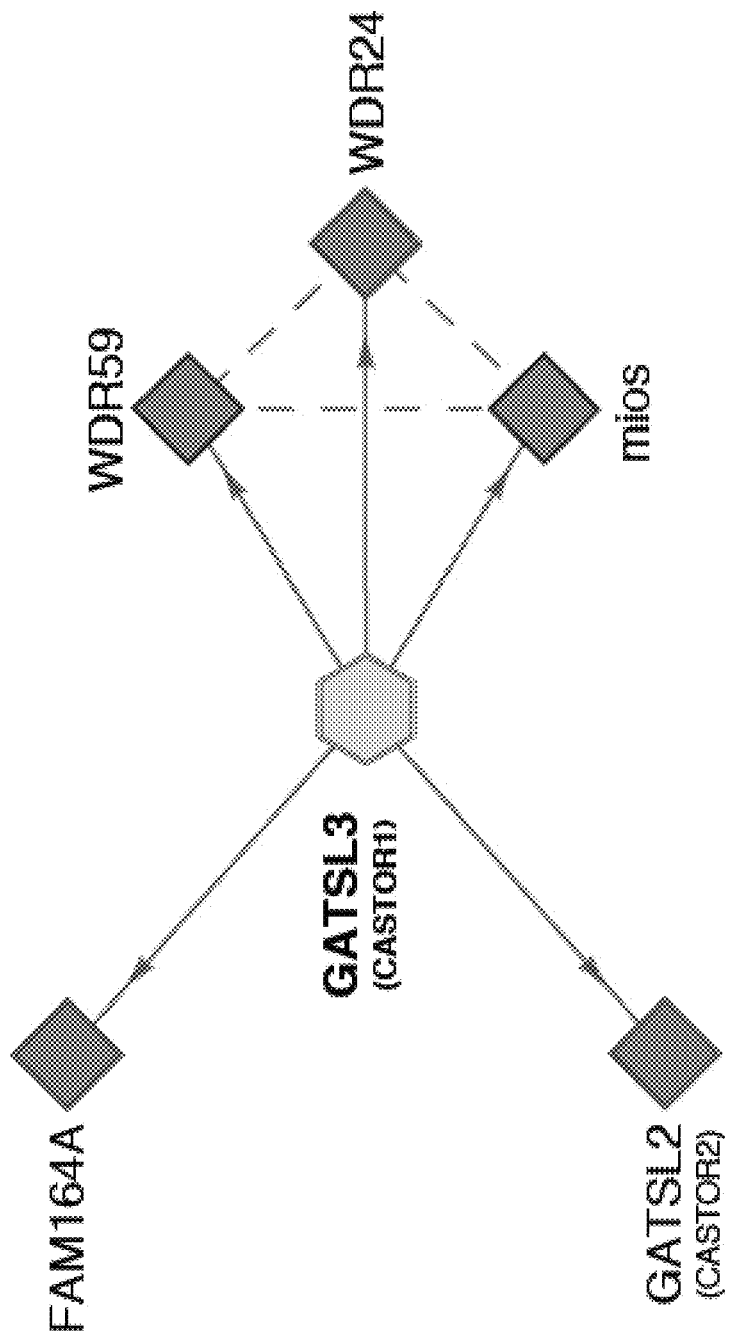

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology. Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

As used herein "modulating" (and verb forms thereof, such as "modulates") means causing or facilitating a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon.

The term "inhibitor" (and verb forms thereof, such as "inhibits"), as used herein means an agent that (a) reduces one or more activities normally associated with the protein being inhibited; (b) reduces or otherwise interferes with the ability of the protein being inhibited to associate with, e.g., bind to, another protein or ligand or nucleic acid; and/or (c) reduces the transcription or expression from a gene that encodes the protein being inhibited.

The terms "activator" and "agonist" (and verb forms thereof, such as "activates" and "agonizes"), as used herein means an agent that (a) increases one or more activities normally associated with the protein being activated; (b) increases or otherwise enhances the ability of the protein being activated to associate with, e.g., bind to, another protein or ligand or nucleic acid; and/or (c) increases the transcription or expression from a gene that encodes the protein being activated. In certain embodiments, modulating, inhibiting, activating and/or agonizing utilizing any of the activating, agonistic, or inhibitory systems, methods or agents described herein can be performed in vitro or ex vivo, for example, by contacting or exposing cells to the activating, agonistic, or inhibitory systems, methods or agents. In certain embodiments, modulating, inhibiting, activating and/or agonizing utilizing any of the activating, agonistic, or inhibitory systems, methods or agents described herein can be performed in vivo.

The term "GATOR2" refers to a protein complex of five different polypeptides: Seh1L, WDR59, WDR24, Sec13 and Mios.

Figure 1B:
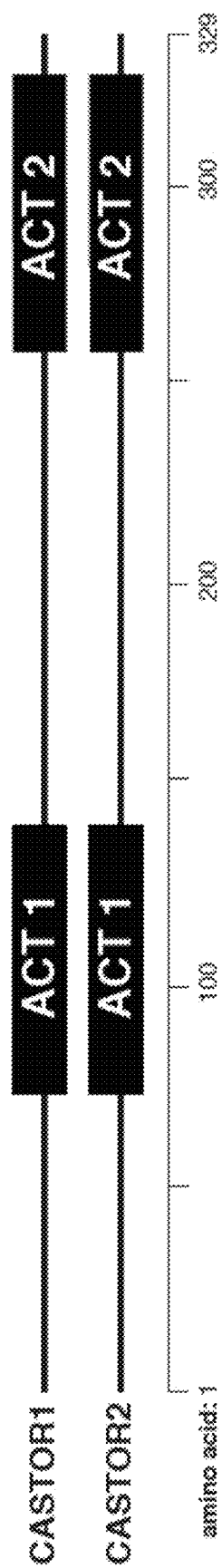

The terms "CASTOR1" and "GATSL3" are used interchangeably herein. CASTOR1 refers to a Cellular Arginine Sensor for mTORC1. As used herein, CASTOR1 refers to a CASTOR1 polypeptide, as well as other isoforms of CASTOR1. In some aspects, protein encoded by the GATS protein-like 3 (GATSL3) gene interacts with three core components of GATOR2 (e.g., WDR24, WDR59 and mios). CASTOR1 resides on chromosome 22 and is lowly expressed across most tissues, with higher expression in various tissues, such as muscle. The terms "CASTOR2" and "GATSL2" are used interchangeably herein. As used herein, CASTOR2 refers to a CASTOR2 polypeptide, as well as other isoforms of CASTOR2. In some aspects, proteins encoded by the GATSL2 gene are present in GATSL3 immunoprecipitates. CASTOR2 resides on chromosome 7, and shares 63% protein sequence identity with CASTOR1. CASTOR2 is lowly expressed across most tissues, with higher expression in select tissues. CASTOR2 and CASTOR1 lack transmembrane domains and obvious localization signals, suggesting they are likely cytosolic proteins. Both proteins contain two tandem ACT domains of 70-80 residues each (FIG. 1B).

The term "GATOR2-binding fragment" refers to the minimal portion of CASTOR1 or a polypeptide that is at least 80% homologous to CASTOR1 that specifically associates with one or more polypeptides of GATOR2. In some embodiments, a GATOR2-binding fragment is the minimal portion of CASTOR1 or a polypeptide that is at least 80% homologous to CASTOR1 that primarily associates with WDR24. In some embodiments, a GATOR2-binding fragment is the minimal portion of CASTOR1 or a polypeptide that is at least 80% homologous to CASTOR1 that primarily associates with WDR59. In some embodiments, a GATOR2-binding fragment is the minimal portion of CASTOR1 or a polypeptide that is at least 80% homologous to CASTOR1 that primarily associates with mios.

The term "CASTOR1 binding fragment" refers to the minimal portion of GATOR2 or a polypeptide or protein complex that is at least 80% homologous to GATOR2 that specifically associates with CASTOR1. In some embodiments, a GATOR2-binding fragment is the minimal portion of WDR24 that specifically associates with CASTOR1. In some embodiments, a GATOR2-binding fragment is the minimal portion of WDR59 that specifically associates with CASTOR1. In some embodiments, a GATOR2-binding fragment is the minimal portion of mios that specifically associates with CASTOR1.

The term "CASTOR2 binding fragment" refers to the minimal portion of GATOR2 or a polypeptide or protein complex that is at least 80% homologous to GATOR2 that specifically associates with CASTOR2. In some embodiments, a GATOR2-binding fragment is the minimal portion of WDR24 that specifically associates with CASTOR2. In some embodiments, a GATOR2-binding fragment is the minimal portion of WDR59 that specifically associates with CASTOR2. In some embodiments, a GATOR2-binding fragment is the minimal portion of mios that specifically associates with CASTOR2.

The term "at least 80% homologous" as used herein with respect to two polypeptide or proteins (the "query" sequence as compared to the "reference" sequence), means at least 80%, 85%, 86%, 87%, 88%, 89%, 90%, 91%, 92%, 93%, 94%, 95%, 96%, 97%, 98%, or 99% identity at an amino acid level as determined conventionally using known sequence alignment computer programs, such as the Bestfit program. When using Bestfit or other sequence alignment programs to determine whether a particular sequence is at least 80% identical to a reference sequence according to the present invention, the parameters are set such that the percentage of identity is calculated over the full length of the portion of the reference amino acid sequence that is homologous to the query sequence. For example, a query polypeptide sequence is at least 80%, 85%, 86%, 87%, 88%, 89%, 90%, 91%, 92%, 93%, 94%, 95%, 96%, 97%, 98%, or 99% identical at the amino acid level to a reference polypeptide sequence over at least 20%, 30%, 40%, 50%, 60%, 70%, 80%, 90%, 95%, 96%, 97%, 98%, 99%, or 100% of the reference polypeptide sequence.

"Conditions that allow the first polypeptide to associate with the second polypeptide or protein complex" generally include a buffered solution at physiological pH and salt concentrations characterized by the absence of compounds known to inhibit the CASTOR1-GATOR2 interaction. Exemplary conditions are those that are substantially free of arginine and/or analogs of arginine. In certain embodiments, such conditions are less than 1 nM of arginine and/or analogs of arginine. In certain embodiments, such conditions are 100% free of arginine and/or analogs of arginine. "Analogs" include modified versions of arginine, as well as compounds identified by the assays of the invention as inhibitors of CASTOR1-GATOR2 interaction. The term "substantially free" as used herein with respect to arginine and/or analogs of arginine means a concentration of less than 100 nM.

The term "test compound" refers to any of a small molecule, nucleic acid, amino acid, polypeptide, antibody and antibody-like molecules, aptamers, macrocycles, or other molecules. In certain embodiments, a test compound is a small organic molecule. In one aspect of these embodiments, the small organic molecule has a molecular weight of less than about 5,000 daltons. In certain embodiments, the test compound is other than an amino acid. In other embodiments, the small molecule is other than arginine or analogs of the foregoing.

In certain embodiments, CASTOR1 and CASTOR2 are ACT domain-containing proteins that interact with GATOR2. In certain aspects, ACT domains of proteins oligomerize to form multi-protein complexes. CASTOR proteins form multiple complexes. In certain embodiments, CASTOR proteins form three different complexes: CASTOR1 homodimer, CASTOR2 homodimer and CASTOR1-CASTOR2 heterodimer. In certain embodiments, the three different CASTOR complexes bind differentially to GATOR2. In some embodiments, the CASTOR2 homodimer interacts with GATOR2, and in certain embodiments, the CASTOR2 homodimer interacts more strongly with endogenous GATOR2 than the CASTOR1 homodimer. In some embodiments, the CASTOR1-CASTOR2 heterodimer binds to GATOR2 at an intermediate level. In some aspects, the invention provides agents that modulate CASTOR1 homo- and/or heterodimerization. In certain aspects, the CASTOR2-GATOR2 complexes are amino acid insensitive. In certain aspects, the CASTOR1-GATOR2 complexes are amino acid sensitive.

In certain embodiments, amino acids (e.g., arginine) modulate the interaction of CASTOR1 with GATOR2. In certain embodiments, arginine is a regulator of the CASTOR1-GATOR2 interaction. In some embodiments, arginine disrupts the interaction between CASTOR1 and GATOR2. In some embodiments, the addition of arginine to a CASTOR1-GATOR2 complex is sufficient to dissociate GATOR2 from both a CASTOR1 homodimer and a CASTOR1-CASTOR2 heterodimer. In certain aspects, the amount of arginine added to the complex to disrupt the interaction is at least 10 µM, 25 µM, 50 µM, 75 µM, 100 µM, 150 µM, 200 µM, 250 µM, 300 µM, 350 µM, or 400 µM. In some aspects, the amount of arginine added to the complex to disrupt the interaction is between 1 µM to 400 µM, 5 µM to 250 µM, 10 µM to 100 µM, 15 µM to 75 µM, or 10 µM to 40 µM. In certain embodiments, half-maximal disruption occurs at an arginine concentration of 20 µM to 40 µM. In some aspects, the invention provides agents that compete with arginine for binding to CASTOR1.

In some embodiments, arginine disrupts the CASTOR1-GATOR2 interaction by binding to CASTOR1. In some aspects, arginine binds to CASTOR1 with a dissociation constant of around 30 µM. In some aspects, the CASTOR1 homodimer and CASTOR1-CASTOR2 heterodimer bind arginine with a dissociation constant of around 30 µM. In some embodiments, the CASTOR1 homodimer and CASTOR1-CASTOR2 heterodimer bind arginine with a dissociation constant of 5 µM to 50 µM, 10 µM to 40 µM, or 20 µM to 35 µM. In some aspects, the $K_d$ of arginine for CASTOR1 in the homodimer is 34.8±5.9 µM. In some aspects, the $K_d$ of arginine for CASTOR1 in the heterodimer is 24.2±4.1 µM.

In certain embodiments, CASTOR1 is a negative regulator of the mTORC1 pathway. In some aspects, CASTOR1 affects the capacity of the mTORC1 pathway to respond to arginine. In some embodiments, CASTOR1 and CASTOR2 are negative regulators of arginine signaling to mTORC1. In some embodiments, CASTOR1 and SLC38A9 function in parallel to enable arginine to regulate mTORC1. In certain aspects, arginine signaling is almost fully defective in the absence of CASTOR1 and SLC38A9.

In some aspects, the disclosure provides a method of identifying a modulator of mTORC1 activity comprising the steps of contacting a test compound with CASTOR1 and/or CASTOR2 or a fragment or mutant thereof that possesses an activity or characteristic of CASTOR1 and/or CASTOR2, measuring an activity or characteristic of CASTOR1 and/or CASTOR2 in the presence of the test compound, and comparing the measured activity or characteristic with the same activity or characteristic in the absence of the test compound, thereby determining whether the test compound is a modulator of CASTOR1 and/or CASTOR2.

In certain embodiments, the invention provides a method of identifying a modulator of mTORC1 activity. The method may comprise containing a test compound with CASTOR1 and/or CASTOR2 or a fragment or mutant thereof that possesses an activity or characteristic of CASTOR1 and/or CASTOR2, measuring an activity or characteristic of CASTOR1 and/or CASTOR2 in the presence of the test compound, and comparing the measured activity or characteristic with the same activity or characteristic in the absence of the test compound, thereby determining whether the test compound is a modulator of CASTOR1 and/or CASTOR2. These methods may employ cellular systems where the CASTOR1 and/or CASTOR2 or a fragment or mutant thereof is engineered to reside at the plasma membrane (e.g., by fusion of the N-terminus to a plasma membrane signal sequence; non-mammalian cellular systems that are engineered to express the CASTOR1 and/or CASTOR2 or a fragment or mutant thereof at the plasma membrane; in vitro systems where the CASTOR1 and/or CASTOR2 or a fragment or mutant thereof is attached to a solid support; and in vitro systems where the CASTOR1 and/or CASTOR2 or a fragment or mutant thereof is free in solution.

Activities or characteristics to be measured in these methods include uptake of labelled (e.g., radiolabelled, fluorescently labelled) amino acids (e.g., arginine, histidine or lysine) in cellular systems, uptake of sodium in cellular systems, changes in membrane potential across a membrane in cellular systems, binding of amino acids to CASTOR1 and/or CASTOR2 or a fragment or mutant thereof in in vitro systems; binding of test compound to CASTOR1 and/or CASTOR2 or a fragment or mutant thereof in in vitro systems; changes in the ability of CASTOR1 and/or CASTOR2 or a fragment or mutant thereof to bind to GATOR2 in both in vivo and in vitro systems; and changes in one or more activities of mTORC1 (e.g., change in phosphorylation state of S6K1).

The measurement of these activities may be achieved by scintillation counting for radiolabelled amino acids; flow cytometry, fluorescence microplate or with a spectrofluorophotometer for fluorescent amino acids and to measure changes in membrane potential (e.g., dyes that change fluorescence in response to changes in membrane potential, e.g., FLIPR dyes (Molecular Devices); patch clamping for measuring electrical currents across a membrane; solid phase surface plasmon resonance to measure changes in amino acid binding or direct binding of test compound; and mass spectrometry to measure changes in amino acid binding or direct binding of test compound.

In some aspects, the disclosure provides a method for modulating the level or activity of mTORC1 in a cell comprising contacting a cell with an agent or composition that modulates (e.g., decreases or increases) the level or activity of CASTOR1 and/or CASTOR2.

In certain embodiments, peptides, polypeptides, fusion proteins and homologs thereof of the invention are useful as competitive inhibitors for the binding of CASTOR1 to GATOR2. In other embodiments, the peptides, polypeptides, fusion proteins and homologs thereof of the invention are useful in assays to identify modulators of CASTOR1. Such modulators may alter the affinity of CASTOR1 for one or more amino acids, e.g., arginine, leucine or lysine, or alter the interaction between CASTOR1 and GATOR2.

In still another embodiment, the invention provides one or more oligonucleotides, e.g., a siRNA, shRNA or antisense oligonucleotide that is complementary to and specifically hybridizes to DNA or mRNA encoding one or more of CASTOR1 or CASTOR2. The oligonucleotides of this invention must be capable of decreasing the transcription and/or translation of the corresponding protein.

In some embodiments, the invention provides a method of identifying a test compound as an activator of mTORC1 activity comprising the steps of:
 a) providing a mixture comprising:
  (i) a first polypeptide comprising a GATOR2-binding fragment of a CASTOR, or a polypeptide having at least 80% homology to a CASTOR that retains the ability to bind GATOR2; and
  (ii) a second polypeptide or protein complex comprising a CASTOR-binding fragment of a GATOR2 complex, or a polypeptide or protein complex having at least 80% homology to a GATOR2 complex that retains the ability to bind to a CASTOR,
under conditions that allow the first polypeptide to associate with the second polypeptide or protein complex;
 b) incubating the mixture of a) with the test compound;
 c) determining whether the amount of the first polypeptide associated with the second polypeptide or protein complex is altered in the presence of the test compound as compared to either the absence of the test compound or the presence of a negative control, wherein if the amount of association is decreased the test compound is identified as an activator of mTORC1 activity.

In some embodiments, the identification of a test compound is performed utilizing isolated proteins (e.g., outside a cell). In alternative embodiments, the identification of a test compound is performed using cell-based assays. In some aspects, the test compound is incubated with cells expressing the first polypeptide and the second polypeptide or protein complex.

In some embodiments, the first polypeptide comprises a GATOR2-binding fragment of CASTOR1, or a polypeptide having at least 80% homology to CASTOR1 that retains the ability to bind GATOR2. In some embodiments, the first polypeptide used in the method comprises a GATOR2-binding fragment of CASTOR1, or an isoform thereof. In some embodiments, the first polypeptide comprises a GATOR2-binding fragment of CASTOR2, or a polypeptide having at least 80% homology to CASTOR2 that retains the ability to bind GATOR2. In some embodiments, the first polypeptide used in the method comprises a GATOR2-binding fragment of CASTOR2, or an isoform thereof. In some aspects, a polypeptide includes protein complexes, such as homodimers and heterodimers. In a more specific aspect of these embodiments, the first polypeptide comprises a CASTOR1 homodimer. In another more specific aspect of these embodiments, the first polypeptide comprises a CASTOR1-CASTOR2 heterodimer. In another specific aspect of these embodiments, the first polypeptide comprises a CASTOR1 homodimer.

In certain embodiments, the first polypeptide comprises an amino acid sequence that is at least 80%, 85%, 86%, 87%, 88%, 89%, 90%, 91%, 92%, 93%, 94%, 95%, 96%, 97%, 98%, or 99% identical to a GATOR2-binding fragment of CASTOR1 over at least 20%, 30%, 40%, 50%, 60%, 70%, 80%, 90%, 95%, 96%, 97%, 98%, 99%, or 100% of the GATOR2-binding fragment of CASTOR1 and retains the ability to bind GATOR2.

In certain embodiments, the second polypeptide or protein complex comprises an amino acid sequence that is at least 80%, 85%, 86%, 87%, 88%, 89%, 90%, 91%, 92%, 93%, 94%, 95%, 96%, 97%, 98%, or 99% to a CASTOR1-binding fragment of a GATOR2 complex over at least 20%, 30%, 40%, 50%, 60%, 70%, 80%, 90%, 95%, 96%, 97%, 98%, 99%, or 100% of the CASTOR1-binding fragment of the GATOR2 complex and retains the ability to bind to CASTOR1.

In other embodiments, the second polypeptide or protein complex comprising a CASTOR1-binding fragment of a GATOR2 complex, or a polypeptide or protein complex having at least 80% homology to a GATOR2 complex that retains the ability to bind to CASTOR1. In other embodiments, the second polypeptide or protein complex comprising a CASTOR2-binding fragment of a GATOR2 complex, or a polypeptide or protein complex having at least 80% homology to a GATOR2 complex that retains the ability to bind to CASTOR2. In some embodiments, the second polypeptide or protein complex comprises a CASTOR1-binding fragment of a GATOR2 complex. In a more specific aspect of these embodiments, the second polypeptide or protein complex comprises a CASTOR1-binding fragment of WDR24. In a more specific aspect of these embodiments, the second polypeptide or protein complex comprises a CASTOR1-binding fragment of WDR59. In a more specific aspect of these embodiments, the second polypeptide or protein complex comprises a CASTOR1-binding fragment of mios.

The determination of whether the amount of the first polypeptide associated with the second polypeptide or protein complex is altered in the presence of the test compound is typically achieved by distinguishing between the first polypeptides associated with the second polypeptides or protein complexes and the first polypeptides that are not associated with the second polypeptides or protein complexes. One way of achieving such differentiation is by binding a tag to at least one of the first or second polypeptide or protein complex and then detecting at least one of the bound tags or a product of the first and second tags. Other ways of achieving such differentiation includes, but is not limited to, separation techniques, such as gel filtration (size exclusion chromatography; non-denaturing gel electrophoresis) and differential centrifugation; and size determination, such as mass spectrometry.

The term "tag" as used herein includes, but is not limited to, detectable labels, such as fluorophores, radioisotopes, colorimetric substrates, or enzymes; heterologous epitopes for which specific antibodies are commercially available, e.g., FLAG-tag; heterologous amino acid sequences that are ligands for commercially available binding proteins, e.g., Strep-tag, biotin; fluorescence quenchers typically used in conjunction with a fluorescent tag on the other polypeptide; and complementary bioluminescent or fluorescent polypeptide fragments. A tag that is a detectable label or a complementary bioluminescent or fluorescent polypeptide fragment may be measured directly (e.g., by measuring fluorescence or radioactivity of, or incubating with an appropriate substrate or enzyme to produce a spectrophotometrically detectable color change for the associated polypeptides as compared to the unassociated polypeptides). A tag that is a heterologous epitope or ligand is typically detected with a second component that binds thereto, e.g., an antibody or binding protein, wherein the second component is associated with a detectable label. A tag, e.g., a heterologous epitope, may also be used to affix or immobilize the polypeptide to which it is bound to a solid support.

As used herein, the term "immobilize" in the context of an immobilized polypeptide or protein complex, refers to a substance that is affixed (e.g., tethered) to a substrate or support (e.g., a solid support), and not free in solution.

The term "solid support" is defined as a solid material of any size, shape, composition or construction that is suitable as an attachment material for any polypeptide or protein complex utilized in the present invention.

Thus, in certain embodiments of the methods described above: the first polypeptide is optionally bound to a first tag; the second polypeptide or protein complex is optionally bound to a second tag; at least one of the first polypeptide or the second polypeptide or protein complex is bound to its corresponding tag; and determining the amount of the first polypeptide associated with the second polypeptide or protein complex: (a) comprises detecting at least one of the first or second tag or a product of the first and second tag; and (b) distinguishes between the first polypeptide associated with the second polypeptide or protein complex and the first polypeptide not associated with the second polypeptide or protein complex.

In certain aspects of the embodiment in which at least one of the first polypeptide or the second polypeptide or protein complex is bound to its corresponding tag: the first tag is present and comprises a first epitope not naturally present in CASTOR1; the second tag is present and comprises a second epitope not naturally present in any GATOR2 complex; detecting the first tag comprises binding a first antibody specific for the first epitope; and detecting the second tag comprises binding a second antibody specific for the second epitope. For the sake of clarity in these aspects, although both the first and the second tags are present, it is not required that both tags be detected, nor that both the first and second antibody be used for detection. Some of the assays that fall under these aspects use only one antibody and detect only one tag. The other tag may be used to affix or immobilize the polypeptide to which it is bound to a solid support.

In other aspects of the embodiment in which at least one of the first polypeptide or the second polypeptide or protein complex is bound to its corresponding tag one of the first polypeptide or second polypeptide or protein complex is immobilized on a solid support. In a more specific aspect, the immobilization on the solid support is mediated through the corresponding tag. In one example, the solid support is a bead or plate coated with an antibody that recognizes the tag, resulting in the tethering of the tagged polypeptide or protein complex to the bead or plate.

In still another aspect of the embodiment in which at least one of the first polypeptide or the second polypeptide or protein complex is bound to its corresponding tag, only one of the first antibody or the second antibody is used for detection of the first or second tag, and the antibody used for detection is conjugated to a detectable label.

In yet another aspect, both the first and second tags are present and are each members of a proximity fluorescence reagent pair. The term "proximity fluorescence reagent pair" refers to two reagents that react with one another to produce detectable fluorescence or phosphorescence when they are in close proximity, e.g., when the two polypeptides to which they are attached are associated with one another. Examples of proximity fluorescence reagent pair that may be utilized in this aspect are donor-acceptor FRET pairs that are well-known in the art and commercially available (e.g., cyan fluorescent protein/yellow fluorescent protein; luciferase/yellow fluorescent protein; blue fluorescent protein/green fluorescent protein 2; dansyl/FITC; Cy3/Cy5; and carboxyfluorescein succinimidyl ester/Texas Red); and bimolecular fluorescence complementation (BiFC) pairs.

In a related aspect, both the first and the second tags are present; the first and second antibodies are both utilized to detect the association of the first polypeptide and the second polypeptide or protein complex; and the first and second antibodies are each conjugated to a different member of a proximity fluorescence reagent pair.

In still another aspect, only one of the first tag or second tag is present; the tag present is a fluorescent moiety bound to the N- or C-terminus of the first polypeptide or the second polypeptide; and detecting the association of the first polypeptide with the second polypeptide or protein complex comprises solution phase fluorescence polarization. In a more specific aspect the tag is 5-carboxyfluorescein attached to the N- or C-terminus of the first or second polypeptide.

In yet another aspect, one of the first polypeptide or second polypeptide or protein complex is immobilized on a solid support; and detecting the association of the first polypeptide with the second polypeptide or protein complex comprises surface plasmon resonance (SPR). The immobilization can occur through direct amine coupling of the protein or through the addition of an avidity-tag such as biotin and tethering the tagged protein to a streptavidin coated matrix.

In other embodiments, the invention provides a method of identifying a test compound as an inhibitor of mTORC1 activity comprising the steps of:
 a) providing a mixture comprising:
  (i) a first polypeptide comprising a GATOR2-binding fragment of a CASTOR, or a polypeptide having at least 80% homology to a CASTOR that retains the ability to bind GATOR2; and
  (ii) a second polypeptide or protein complex comprising a CASTOR-binding fragment of a GATOR2 complex, or a polypeptide or protein complex having at least 80% homology to a GATOR2 complex that retains the ability to bind to a CASTOR,
 b) incubating the mixture of a) with the test compound;
 c) determining whether the amount of the first polypeptide associated with the second polypeptide or protein complex is altered in the presence of the test compound as compared to either the absence of the test compound or the presence of a negative control, wherein if the amount of association is increased the test compound is identified as an inhibitor of mTORC1 activity.

In certain aspects, steps (b) and (c) occur under conditions that prevent the first polypeptide from associating with the second polypeptide or protein complex. "Conditions that prevent the first polypeptide from associating with the second polypeptide or protein complex" typically mean the presence of arginine, but also include the presence of other agents known to prevent such association. These other agents may be identified in the assays described above. In one aspect, the assays for identifying inhibitors of association are done in the presence of arginine.

In certain embodiments, the first polypeptide comprises a GATOR2-binding fragment of CASTOR1, or a polypeptide having at least 80% homology to CASTOR1 that retains the ability to bind GATOR2. In other embodiments, the first polypeptide comprises a GATOR2-binding fragment of CASTOR2, or a polypeptide having at least 80% homology to CASTOR2 that retains the ability to bind GATOR2. In some embodiments, a second polypeptide or protein complex comprising a CASTOR1-binding fragment of a GATOR2 complex, or a polypeptide or protein complex having at least 80% homology to a GATOR2 complex that retains the ability to bind to CASTOR1. In other embodiments, a second polypeptide or protein complex comprising a CASTOR2-binding fragment of a GATOR2 complex, or a polypeptide or protein complex having at least 80% homology to a GATOR2 complex that retains the ability to bind to a CASTOR2.

Each of the specific embodiments and aspects set forth above for the method of identifying a test compound as an activator of mTORC1 are also applicable to the method of identifying a test compound as an inhibitor of mTORC1.

In other embodiments, the invention provides a method of identifying a test compound as a modulator of mTORC1 by determining if the test compound can induce or increase the affinity of CASTOR1 for arginine. In one aspect of these embodiments, the method comprises the steps of:
 a. providing a mixture comprising:
  i. a CASTOR1 polypeptide, or a polypeptide having at least 80% homology to CASTOR1 that retains the ability to bind arginine; and
  ii. arginine, under conditions that allow arginine to bind to the polypeptide;
 b. incubating the mixture of a) with the test compound; and
 c. determining whether the amount of arginine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In another related aspect of these embodiments, the method comprises the steps of:
 a. providing a mixture comprising:
  i. a polypeptide comprising an arginine binding fragment of CASTOR1, or a polypeptide having at least 80% homology to CASTOR1 that retains the ability to bind arginine; and
  ii. the test compound;
 b. incubating the mixture of a) with arginine under conditions that allow arginine to bind to the polypeptide; and
 c. determining whether the amount of arginine bound to the polypeptide is altered in the presence of the test compound as compared to either the absence of the test compound or the presence of a negative control, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In another related aspect of these embodiments, the method comprises the steps of:
 a. providing a mixture comprising:
  i. a polypeptide comprising an arginine binding fragment of CASTOR1, or a polypeptide having at least 80% homology to CASTOR1 that retains the ability to bind arginine; and
  ii. the test compound;
 b. incubating the mixture of a) with arginine under conditions that allow arginine to bind to the polypeptide; and
 c. determining whether the amount of arginine bound to the polypeptide is altered in the presence of the test compound as compared to either the absence of the test compound or the presence of a negative control, and determining that the test compound is not competing with arginine for binding to CASTOR1 and acting as an arginine mimetic, wherein if the amount of binding is decreased in the presence of test compound, the test compound is identified as an inhibitor of mTORC1 activity; and if the amount of binding is increased in the presence of the test compound, the test compound is identified as an activator of mTORC1 activity.

In another related aspect of these embodiments, the method comprises the steps of:
 a. providing a mixture comprising:
  i. a CASTOR1 polypeptide, or a polypeptide having at least 80% homology to CASTOR1 that retains the ability to bind arginine; and
  ii. arginine, under conditions that allow arginine to bind to the polypeptide;
 b. incubating the mixture of a) with the test compound; and c. determining whether the amount of arginine bound to the polypeptide is altered in the presence of the test compound as compared to either the absence of the test compound or the presence of a negative control, and determining that the test compound is not competing with arginine for binding to CASTOR1 and acting as an arginine mimetic, wherein if the amount of binding is decreased in the presence of test compound, wherein if the amount of binding is decreased in the presence of test compound, the test compound is identified as an inhibitor of mTORC1 activity; and if the amount of binding is increased in the presence of the test compound, the test compound is identified as an activator of mTORC1 activity In some aspects, the term "mimetic" as used herein refers to an agent that either emulates the biological effects of arginine on mTORC1 activation in a cell, as measured by mTORC1 phosphorylation of an mTORC1 substrate (e.g., S6K) in response to the agent, or that increases, directly or indirectly, the level of arginine in a cell. In certain aspects of these embodiments, the modulator is not a peptide or peptide analog having at least 10% arginine content (e.g. at least 10% of the amino acids in the peptide are arginine). Modulators of CASTOR1, may be identified by screening commercially available small molecule and natural product libraries and may be further optimized for CASTOR1 modulating activity by well-known medicinal chemistry manipulations and modifications.

In certain aspects of the above embodiments, the arginine utilized for determining if the test compound can modulate the affinity of CASTOR1 for arginine is tagged with a detectable label. In one aspect of these embodiments, the arginine is tagged with a radiolabel, such as $^3$H. In another aspect of these embodiments, the method additionally comprises the step of separating polypeptide-bound tagged arginine from free tagged arginine prior to determining the amount of arginine bound to the polypeptide. This may be achieved by method well known in the art, including the immobilization of any polypeptide-arginine complexes to a solid support via an immobilized antibody specific to the polypeptide. Once the separation of bound and free arginine has been achieved, radioactivity of the bound portion can be measured and compared to polypeptide-bound arginine in the absence of test compound or the presence of a negative control compound.

In still other embodiments, the invention provides a method of agonizing mTORC1 activity in a cell by contacting the cell with an agent that inhibits or reduces the interaction of CASTOR1 with a GATOR2 complex. The method of agonizing mTORC1 activity may include maintaining or continuing mTORC1 activity levels or increasing mTORC1 activity levels as compared to a control state (e.g., measured mTORC1 activity levels when CASTOR1 interacts with the GATOR2 complex).

In still other embodiments, the invention provides a method of agonizing mTORC1 activity in a cell by contacting the cell with an agent that increases the binding of arginine by CASTOR1.

In other embodiments, the invention provides a method of treating a disease, condition or disorder in a subject which would benefit by activating mTORC1 activity in a subject comprising the step of administering to the subject an agent that reduces or antagonizes the interaction of a CASTOR1 with the GATOR2 complex. In related embodiments, the invention provides a method of treating a disease, condition or disorder in a subject which would benefit by activating mTORC1 activity in a subject comprising the step of administering to the subject an agent that increases the binding of arginine by CASTOR1. In one aspect of either of these embodiments, the disease, condition or disorder is selected from those resulting in skeletal muscle atrophy (such as sarcopenia, muscle denervation, prolonged immobilization and muscular dystrophy), decreased satiety (e.g., cachexia and anorexia), ribosomopathies (e.g. Diamond-Blackfan anemia, 5q-syndrome, Shwachman-Diamond syndrome, X-linked dyskeratosis, cartilage hair hypoplasia, and Treacher Collins syndrome) and cohesinopathies (e.g. Roberts syndrome and Cornelia de Lange syndrome).

Agents that are useful in the above-described methods of increasing mTORC1 activation include test compounds identified by the mTORC1 activator identification assays set forth herein. In some embodiments, the agent is other than arginine. In some embodiments, the agent is other than a naturally occurring amino acid. In some embodiments, the agent is other than an amino acid.

In still other embodiments, the invention provides a method of inhibiting or decreasing mTORC1 activity in a cell by contacting the cell with an agent that induces or increases the interaction of CASTOR1 with a GATOR2 complex, or that prevents the dissociation of CASTOR1 with GATOR2 in the presence of arginine.

In still other embodiments, the invention provides a method of inhibiting or decreasing mTORC1 activity in a cell by contacting the cell with an agent that decreases the binding of arginine by CASTOR1.

In other embodiments, the invention provides a method of treating a disease, condition or disorder in a subject which would benefit by inhibiting or decreasing mTORC1 activity in a subject comprising the step of administering to the subject an agent that induces or increases the interaction of CASTOR1 with the GATOR2 complex, or that prevents the dissociation of CASTOR1 with GATOR2 in the presence of arginine. In other related embodiments, the invention provides a method of treating a disease, condition or disorder in a subject which would benefit by inhibiting or decreasing mTORC1 activity in a subject comprising the step of administering to the subject an agent that decreases the binding of arginine by CASTOR1. In one aspect of either of these embodiments, the disease, condition or disorder is selected from a metabolic disease (e.g., type 2 diabetes, obesity, non-alcoholic steatohepatitis (NASH), and hyperlipidemia), a neurodegenerative disease (e.g., Alzheimer's disease, Parkinson's Disease, Huntington's Disease, and amyotrophic lateral sclerosis), an autoimmune disease (e.g., psoriasis, rheumatoid arthritis, multiple sclerosis, systemic lupus erythematosus, gout, allergic rhinitis, Crohn's Disease, and ulcerative colitis), rare and mitochondrial disease (e.g., Leigh's Syndrome, Friedreich's Ataxia Cardiomyopathy, Leber's Hereditary Optic Neuropathy, lymphangioleiomyomatosis, tuberous sclerosis, Pompe Disease (Glycogen storage disease II), and lysosomal storage diseases), cardiovascular disease (e.g., cardiomyopathy, heart failure, ischemic heart disease (atherosclerotic disease), ischemic stroke, and pulmonary arterial hypertension), renal disease (e.g., diabetic nephropathy, polycystic kidney disease, and acute kidney injury), neuropsychiatric disease (e.g., epilepsy, autism spectrum disorder, and depressive disorder), oncological disease (e.g., renal cell carcinoma, solid tumors, hematological cancers), and improving immune response to vaccines and other medically important uses in cases of a suppressed immune system such as age-related immunosenescence and cancer immunotherapy.

Agents that are useful in the above-described methods of decreasing or inhibiting mTORC1 activity include test compounds identified by the mTORC1 inhibitor identification assays set forth herein. Other agents that are useful in the above-described methods of decreasing mTORC1 activation include agents that mimic amino acid starvation and/or glucose starvation. Such agents may be confirmed as increasing CASTOR1-GATOR2 interaction through testing in the mTORC1 inhibitor identification assays of the invention.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

EXAMPLES

CASTOR1 and CASTOR2 are ACT Domain-Containing Proteins that Interact with GATOR2

Given its central role as a positive regulator of the mTORC1 pathway, GATOR2 is likely to integrate multiple amino acid inputs to mTORC1, and therefore other sensors in addition to Sestrin2 may interact with it. To identify potential GATOR2-binding partners, we interrogated BioPlex, a database of human protein-protein interactions generated from immunoprecipitation followed by mass spectrometry of 2,594 proteins stably expressed in HEK-293T cells (Huttlin et al., 2015). In this dataset, three core components of GATOR2-WDR24, WDR59 and mios— were found to interact with the protein encoded by the GATS protein-like 3 (GATSL3) gene (FIG. 1A). In addition, proteins encoded by the GATSL2 and FAM164A genes were also present in GATSL3 immunoprecipitates. No prior work exists for GATSL3, GATSL2, or FAM164A. For reasons that are described later, we have renamed GATSL3 as CASTOR1 (Cellular Arginine Sensor for mTORC1) and GATSL2 as CASTOR2.

Figure 7A:
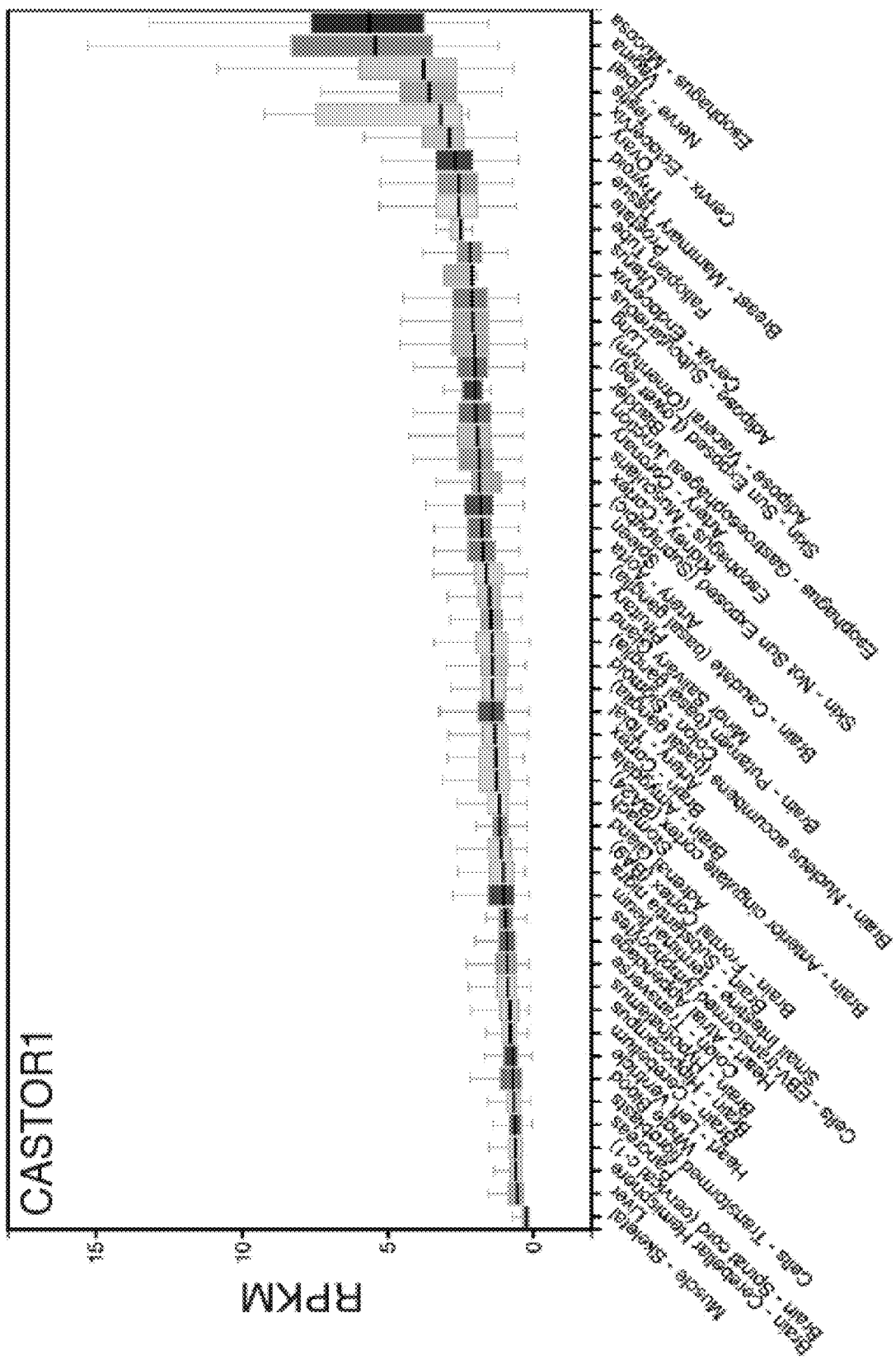
Figure 7A:
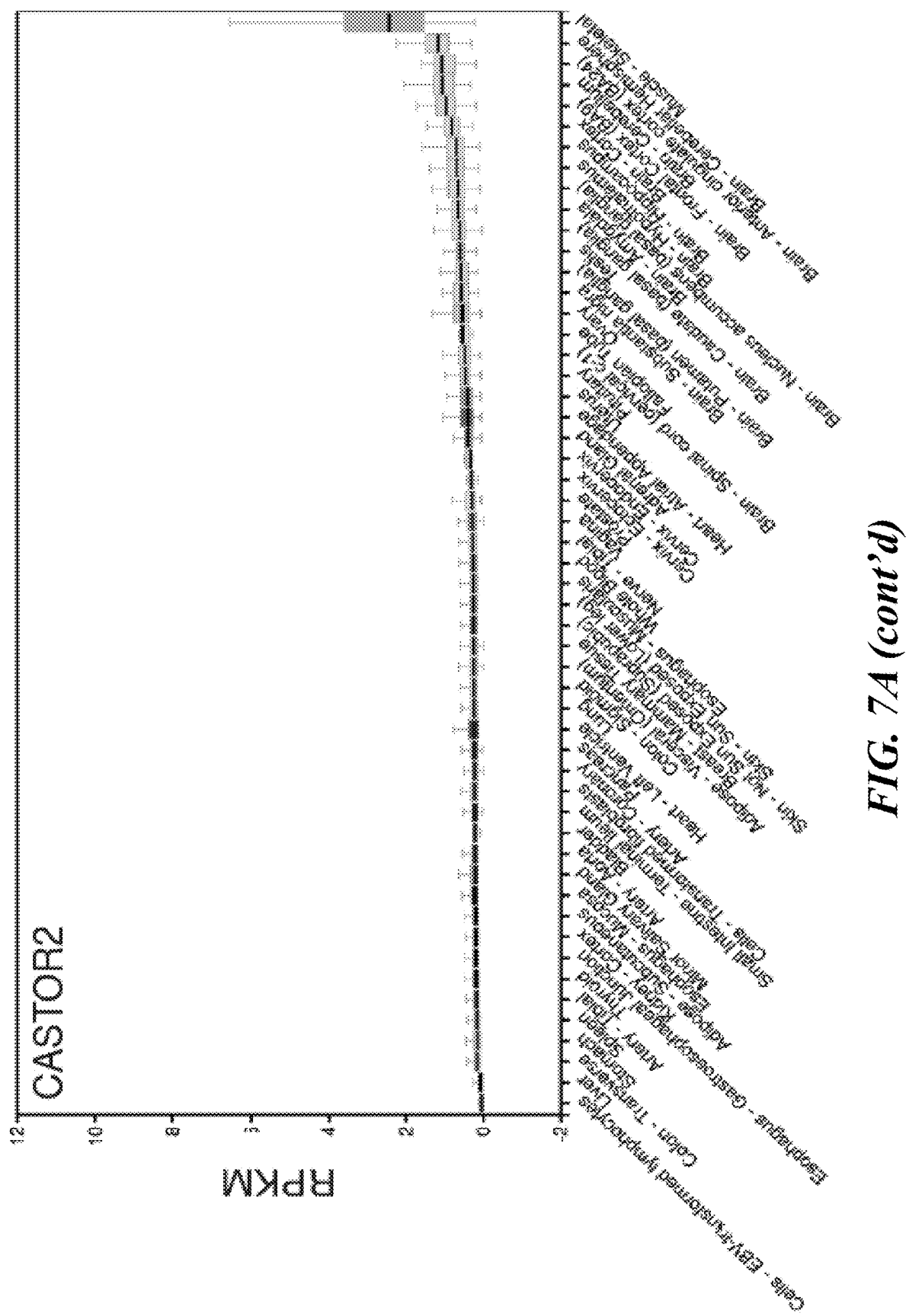

In humans, CASTOR1 and CASTOR2 reside on chromosome 22 and 7, respectively, and are very similar, sharing 63% protein sequence identity. Both genes are lowly expressed across most tissues, with higher expression in some, such as the muscle for CASTOR2 (FIG. 7A). All human genome assemblies except the most recent (hg38) annotate on chromosome 7 an adjacent duplication of CASTOR2 termed GATSL1. GATSL1 encodes a protein that is nearly identical to CASTOR2, having only an N17K change; however, this change is not conserved across species nor does it lead to functional differences between GATSL1 and CASTOR2 (data not shown). Whether or not GATSL1 exists in the human genome is unclear, but if it does, GATSL1 is unlikely to encode for a protein that is functionally distinct from CASTOR2. Therefore, we do not consider GATSL1 further.

Figure 7B:
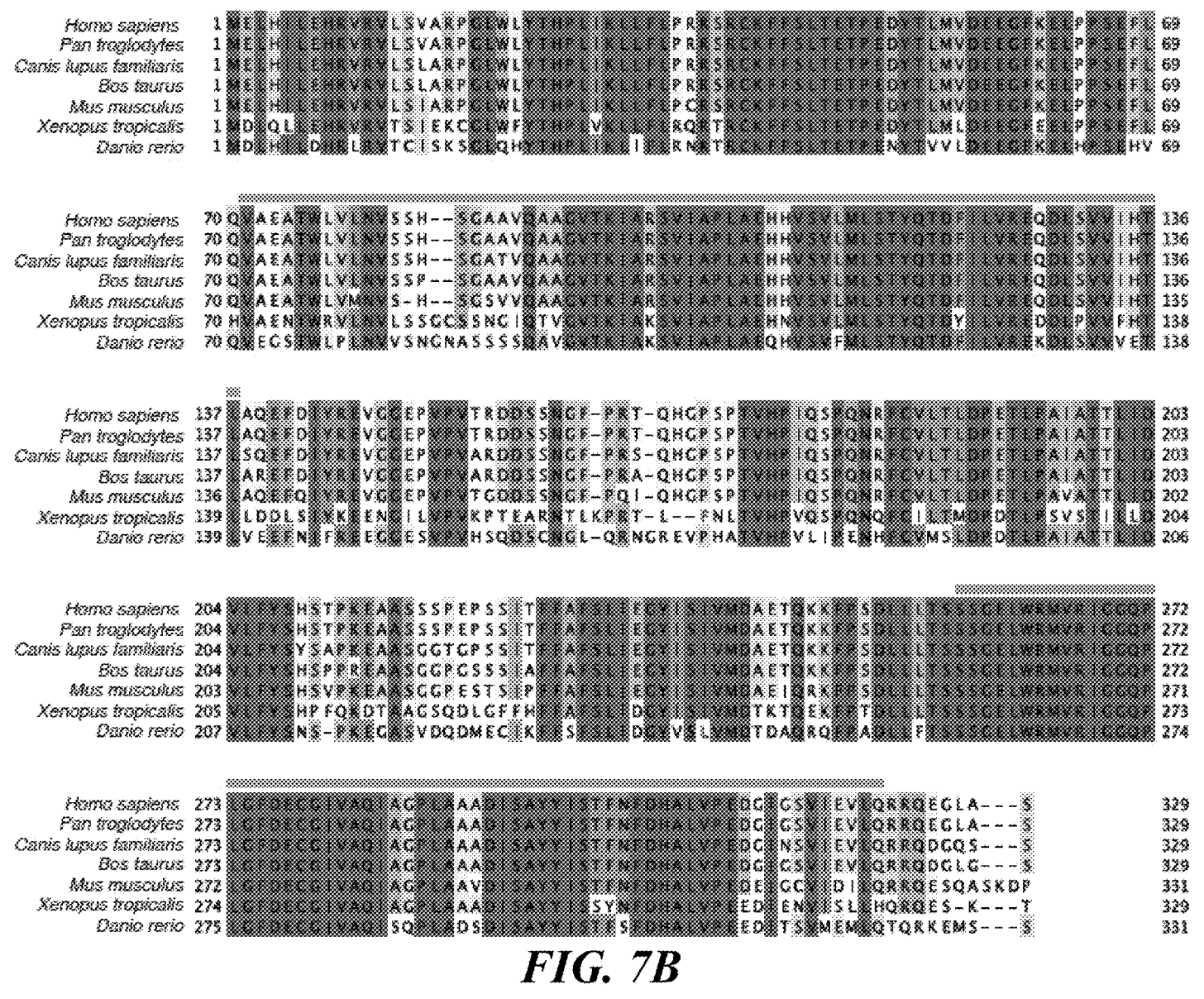
Figure 7C:
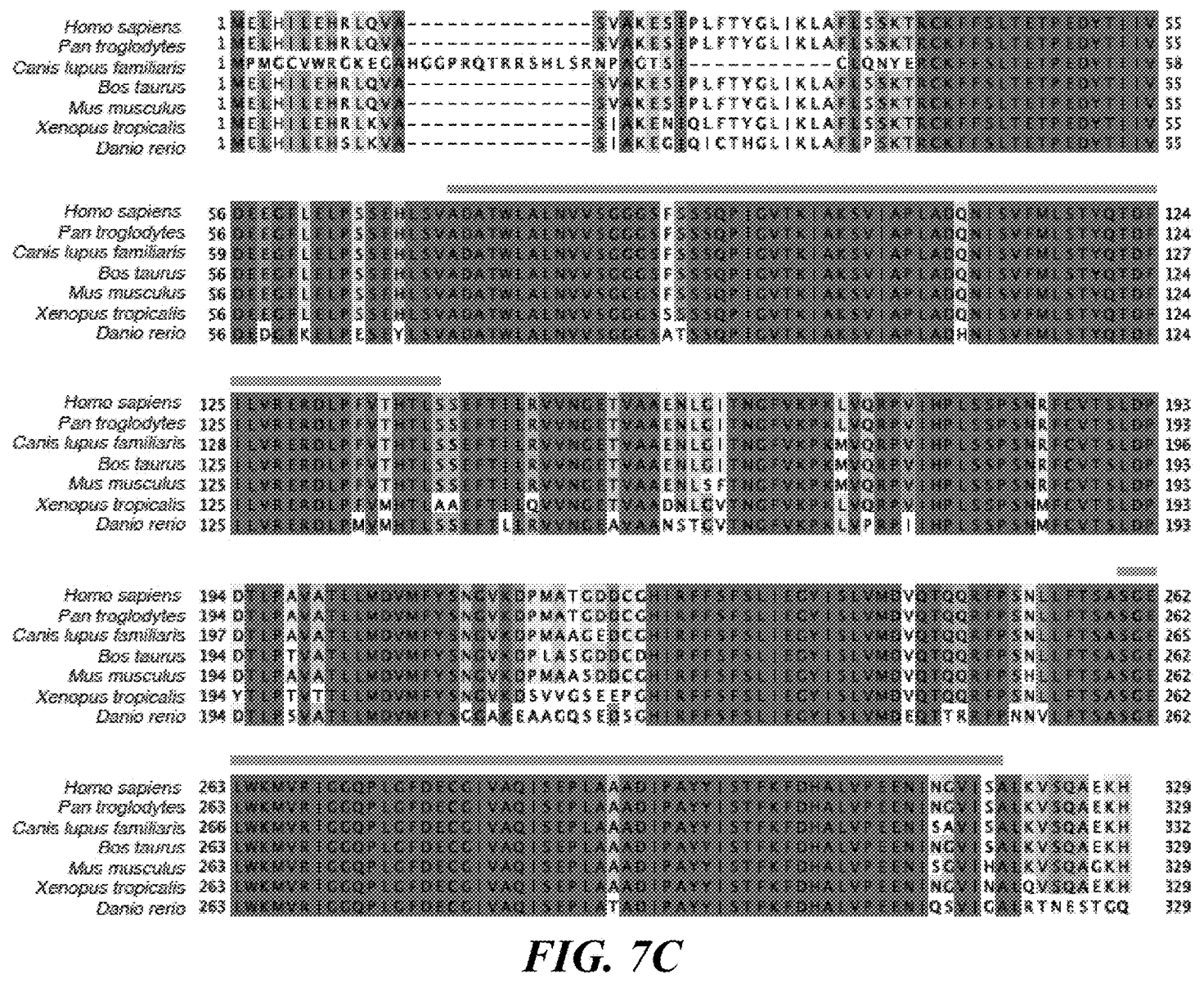
Figure 7D:
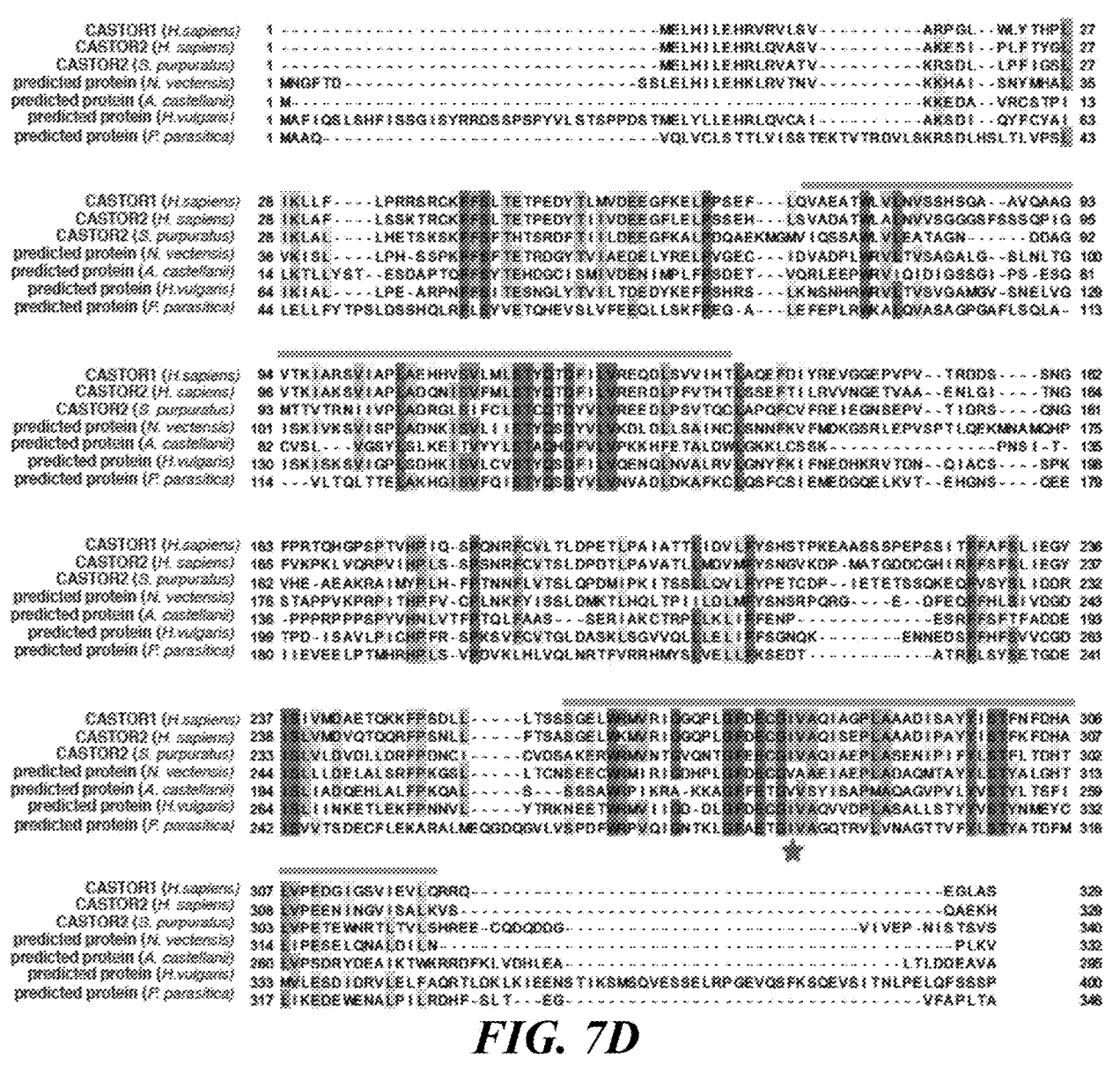

Orthologs of both CASTOR proteins are readily detectable in vertebrates, including zebrafish (FIGS. 7A and 7B) but are absent in other established model organisms such as S. cerevisiae, S. pombe, C. elegans, and D. melanogaster. Database searches also revealed the presence of potential CASTOR homologs in some invertebrates like hydra and sea urchins as well as in a variety of fungi such as P. parasitica and C. albicans (FIG. 7D). In contrast to vertebrates that encode two CASTOR proteins, these organisms encode only one CASTOR-like protein, suggesting that the duplication of an ancestral CASTOR gene yielded CASTOR1 and CASTOR2 in vertebrates.

Figure 1C:
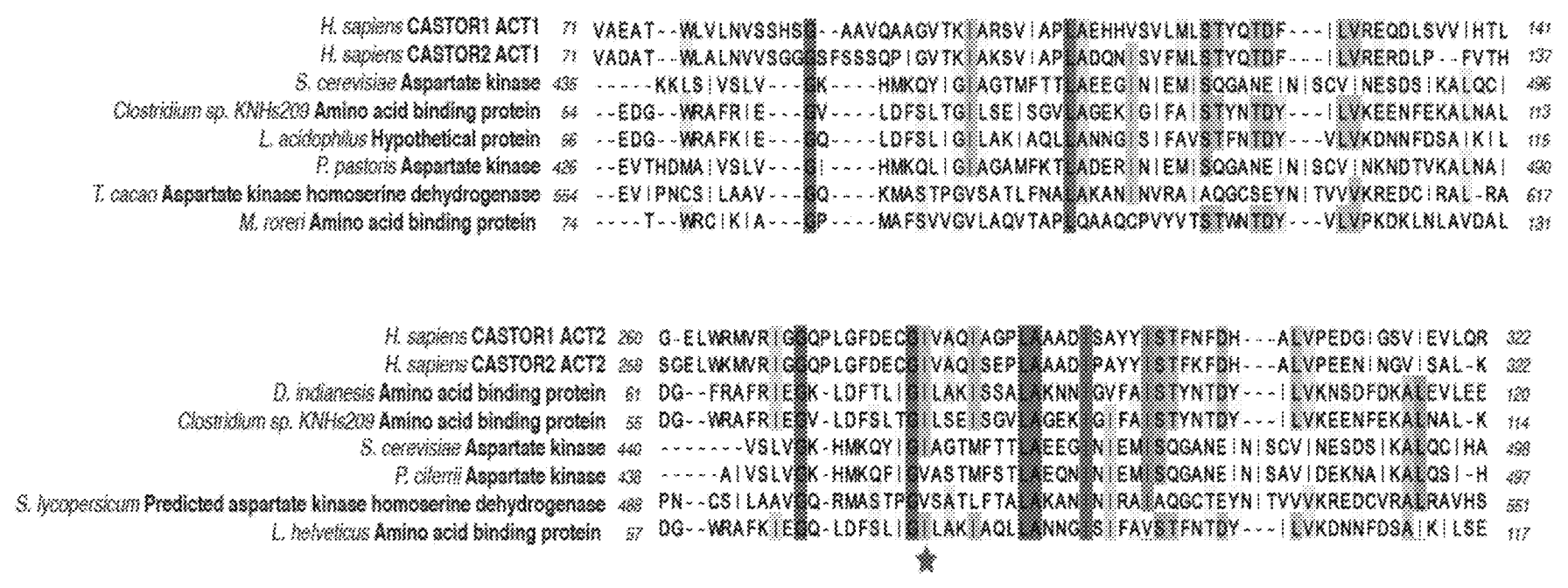

Both CASTOR1 and CASTOR2 lack transmembrane domains and obvious localization signals, suggesting they are likely cytosolic proteins. Intriguingly, both proteins contain two tandem ACT domains of 70-80 residues each (FIG. 1B). ACTs are evolutionarily ancient domains that function as small molecule binding modules for diverse ligands, including amino acids and nucleotides (Aravind and Koonin, 1999; Chipman, 2001; Grant, 2006; Lang et al., 2014). These domains confer complex allosteric regulation to varied proteins, predominantly bacterial enzymes involved in purine and amino acid metabolism. To date, the aromatic amino acid hydroxylases are the only ACT-containing proteins identified and characterized in mammals (Aravind and Koonin, 1999; Carluccio et al., 2013; Grant, 2006; Kobe et al., 1999; Lang et al., 2014; Siltberg-Liberles and Martinez, 2009). A BLAST search of the NCBI protein database with each individual CASTOR ACT domain revealed that they are most similar to the ACT domains of budding yeast aspartate kinase, which binds lysine (Dumas et al, 2012), as well as several putative amino acid binding proteins in bacteria (FIG. 1C).

Figure 1D:
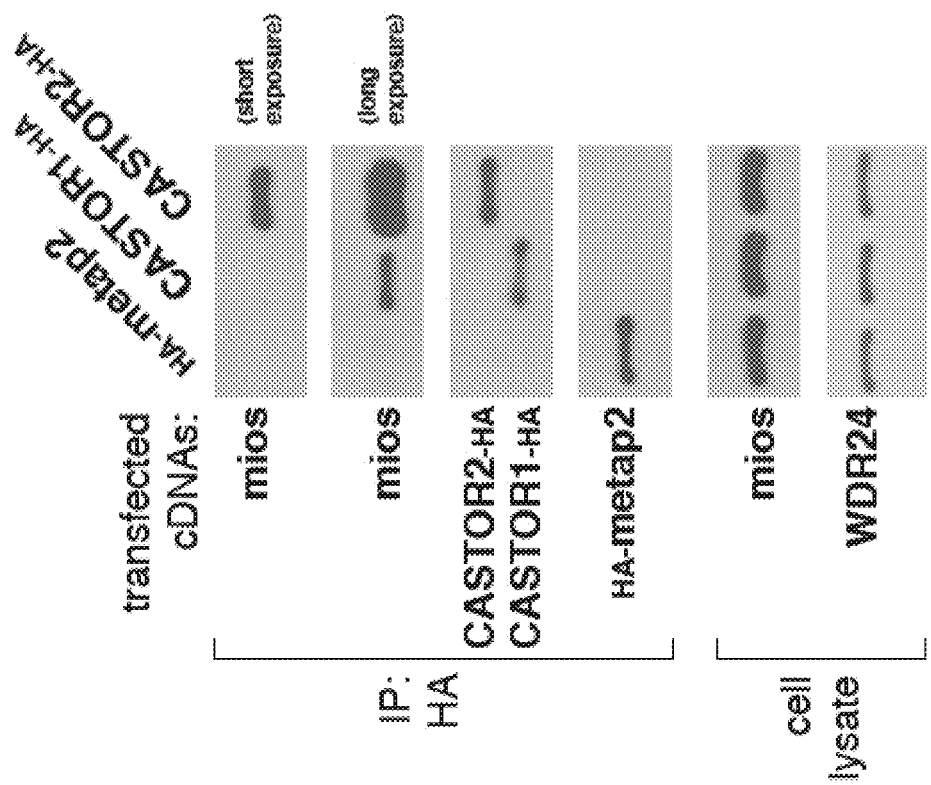

Work described herein first sought to validate the identification of CASTOR1 as a GATOR2-interacting protein. When expressed as an HA-tagged protein in HEK-293T cells, CASTOR1, but not the metap2 control protein, co-immunoprecipitated endogenous mios, an established GATOR2 component (FIG. 1D). Given the sequence similarity of CASTOR1 and CASTOR2, we asked whether recombinant CASTOR2 could also interact with GATOR2. Indeed, CASTOR2 co-immunoprecipitated an even greater amount of mios than CASTOR1 (FIG. 1D).

Figure 7E:
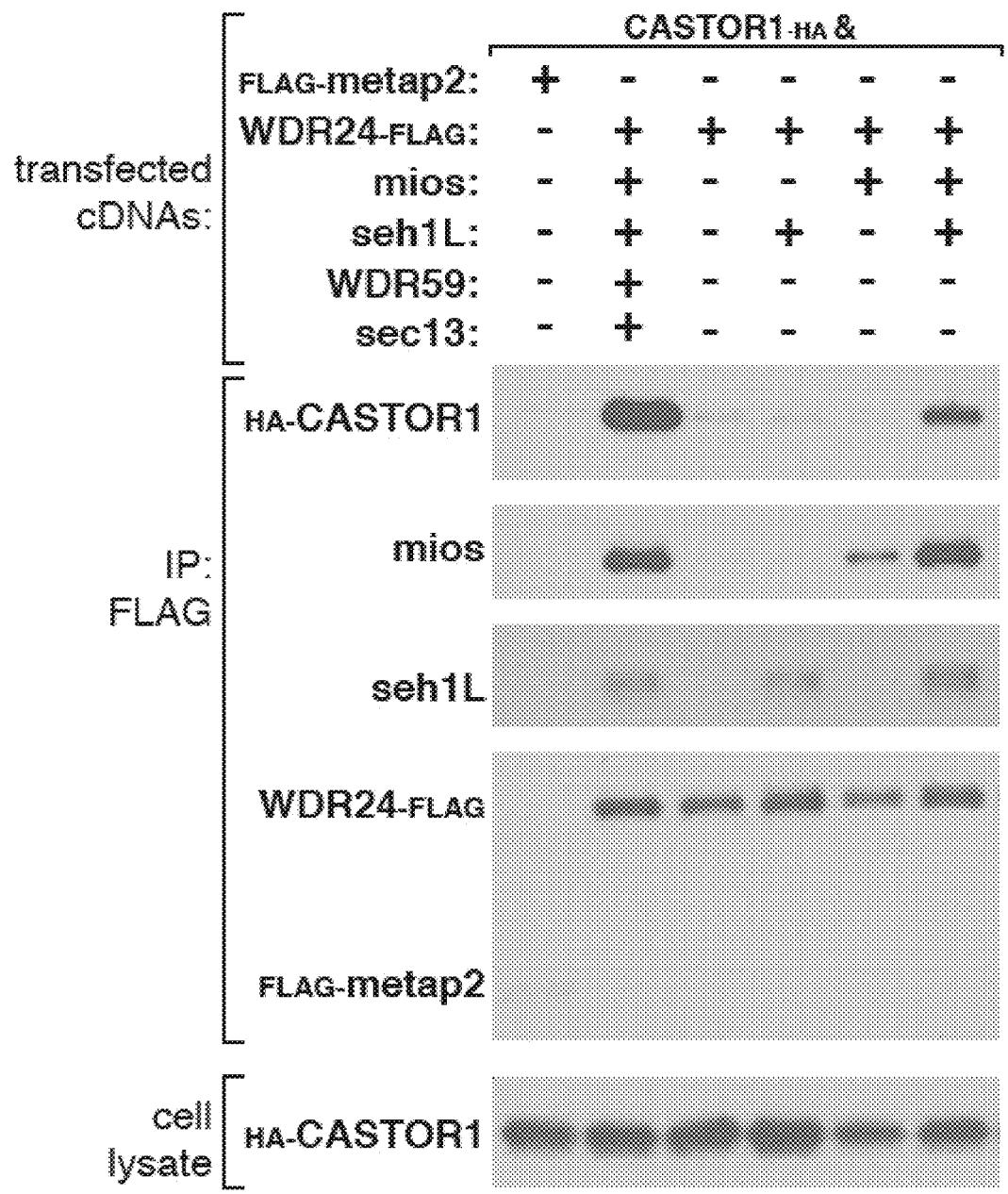
Figure 7F:
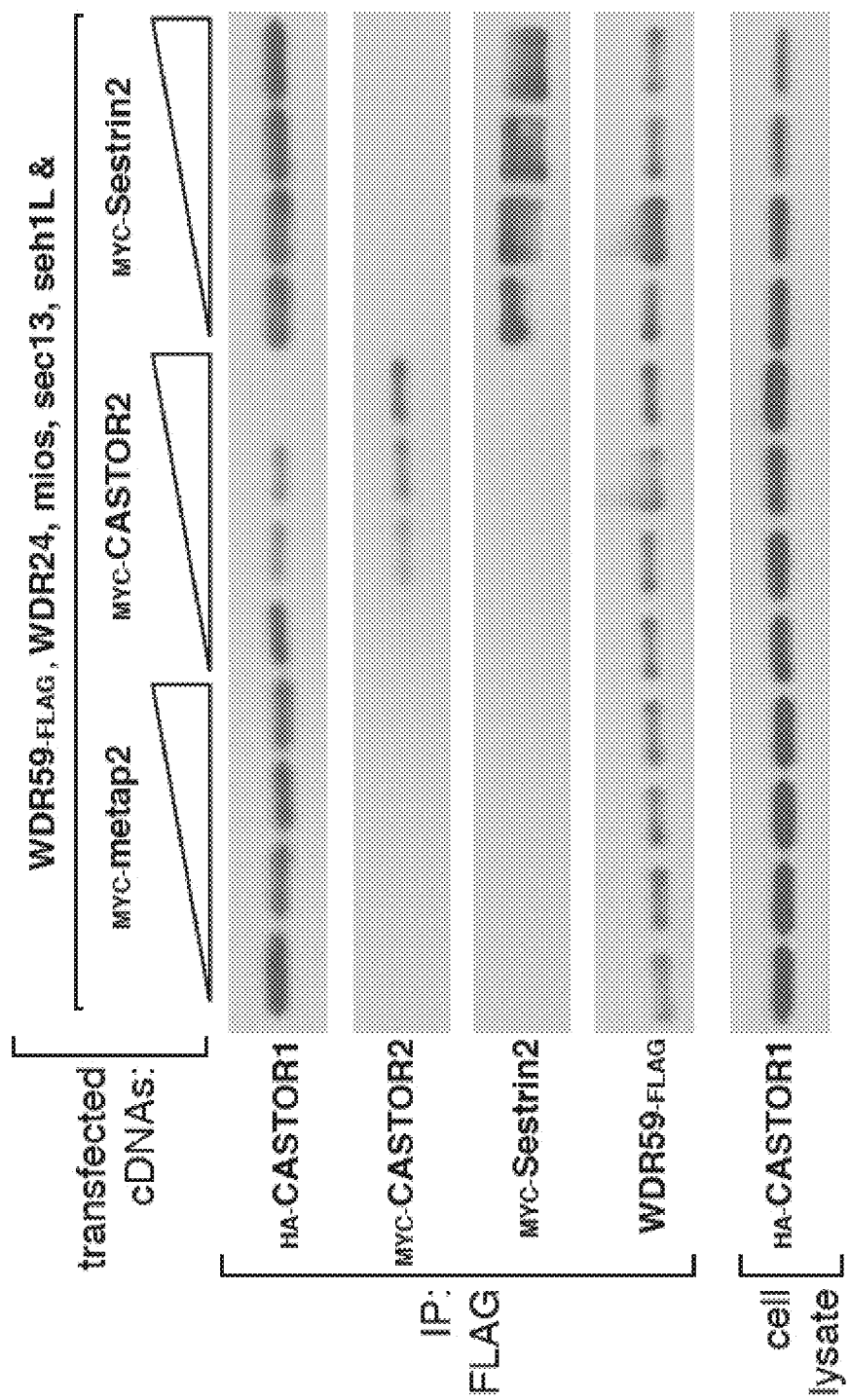

To define which GATOR2 components bind the CASTOR proteins, we compared the ability of different GATOR2 subunits to co-immunoprecipitate CASTOR1. Together, WDR24 mios, and seh1L form a minimal unit that was sufficient to interact with CASTOR1, although it did not recapitulate the degree of binding observed with the complete GATOR2 complex (FIG. 7E). Given that GATOR2 binds not only to the CASTORs but also to Sestrin1, Sestrin2, and Sestrin3 (Chantranupong et al., 2014; Kim et al., 2015; Parmigiani et al., 2014), we asked whether these proteins occupy unique sites on GATOR2. CASTOR2, but not Sestrin2, effectively displaced CASTOR1 from GATOR2, indicating that the CASTORs bind to the same site on the GATOR2 complex, and that it is distinct from that for the Sestrins (FIG. 7F). Collectively, these findings establish CASTOR1 and CASTOR2 as ACT domain-containing proteins that interact with GATOR2.

CASTOR1 and CASTOR2 Form Homo- and Heterodimeric Complexes

Figures 2A, 2B:
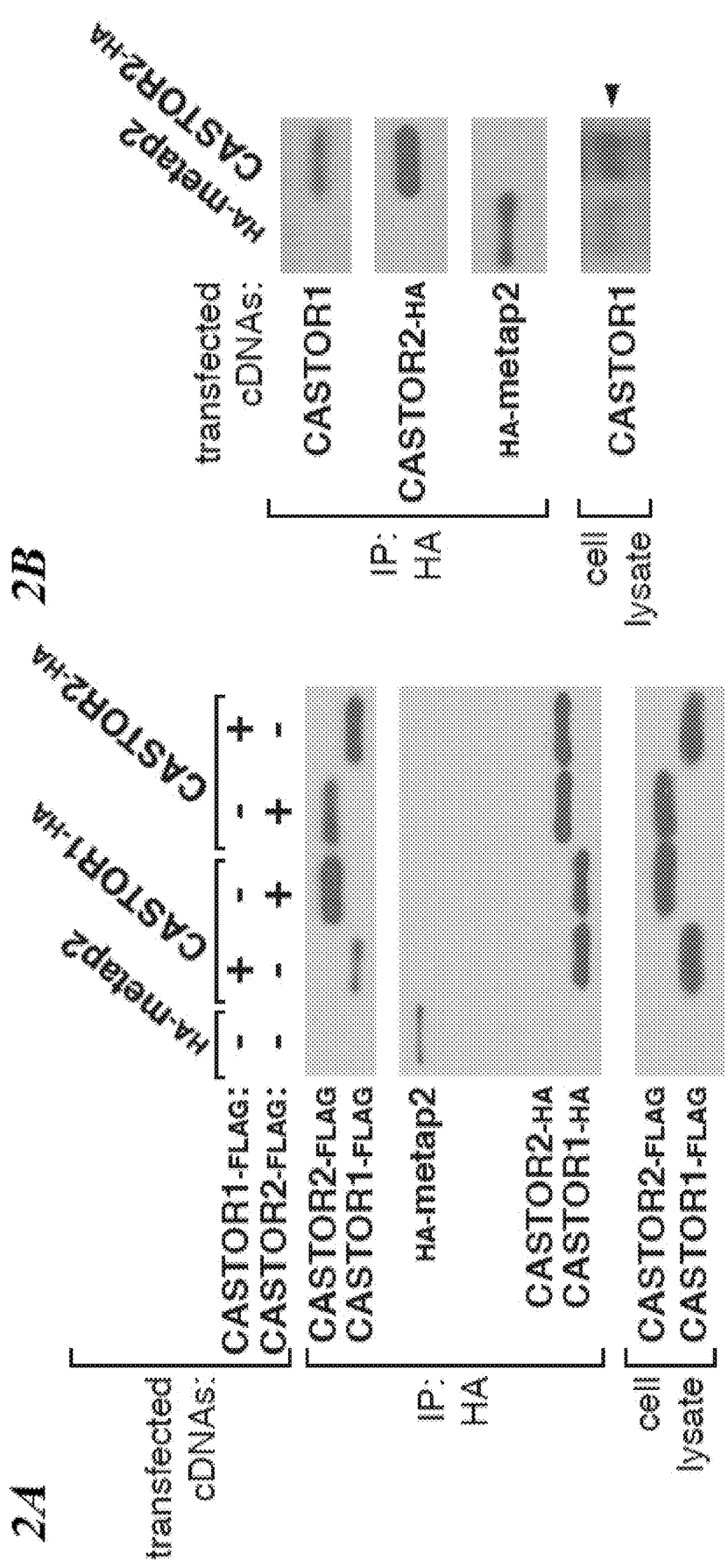
FIG. 2A, FIG. 2B, FIG. 2C and FIG. 2D depict CASTOR1 and CASTOR2 form homo- and heterodimeric complexes.
Figures 8C, 8D:
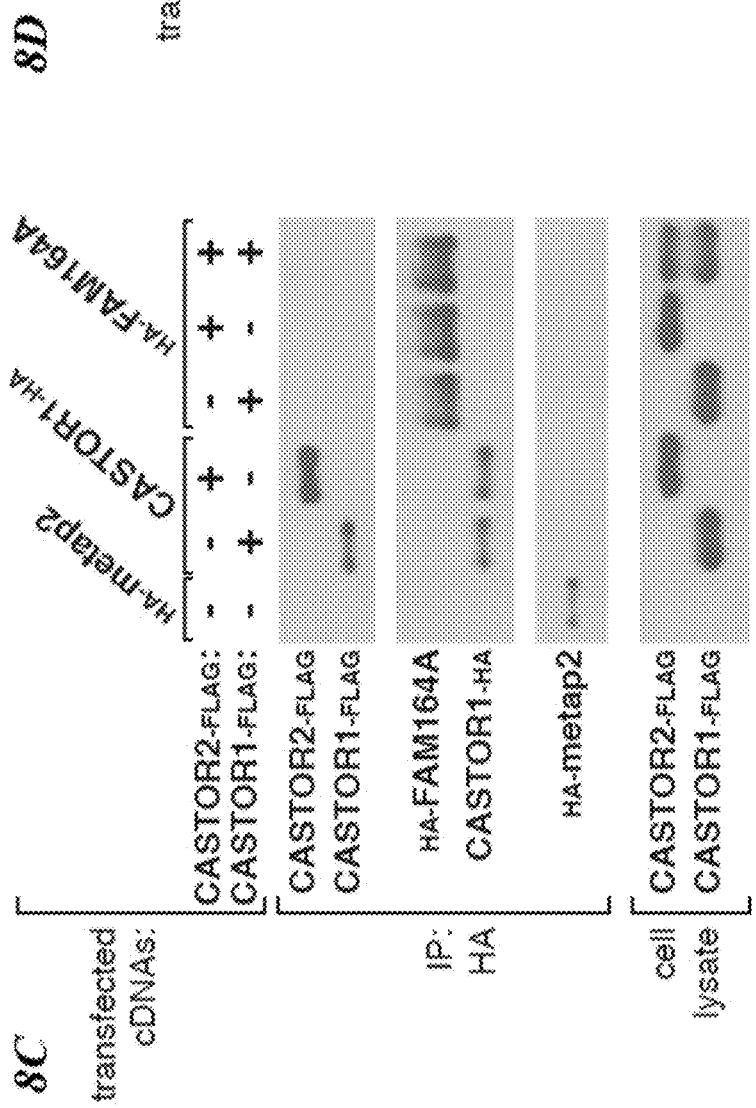

Previous structural studies show that the ACT domains of proteins can oligomerize to form multi-protein complexes (Lang et al., 2014). Consistent with this possibility, we noted a potential interaction between CASTOR1 and CASTOR2 in BioPlex (FIG. 1A). Indeed, when overexpressed in cells, CASTOR1 and CASTOR2 robustly interacted with themselves and each other to form homo- and heterooligomers (FIG. 2A). Gratifyingly, endogenous CASTOR2 and CASTOR1 can also participate in heterooligomeric complexes as they copurified with recombinant CASTOR1 and CASTOR2, respectively (FIGS. 2B and 2C, FIGS. 8A and 8B). In addition to CASTOR2, we also identified FAM164A, a zinc finger-containing protein, as a potential interacting partner of CASTOR1 (FIG. 1A). However, we do not consider FAM164A further as we could not detect an interaction with CASTOR1 or GATOR2 (FIGS. 8C and 8D).

Figures 2C, 2D:
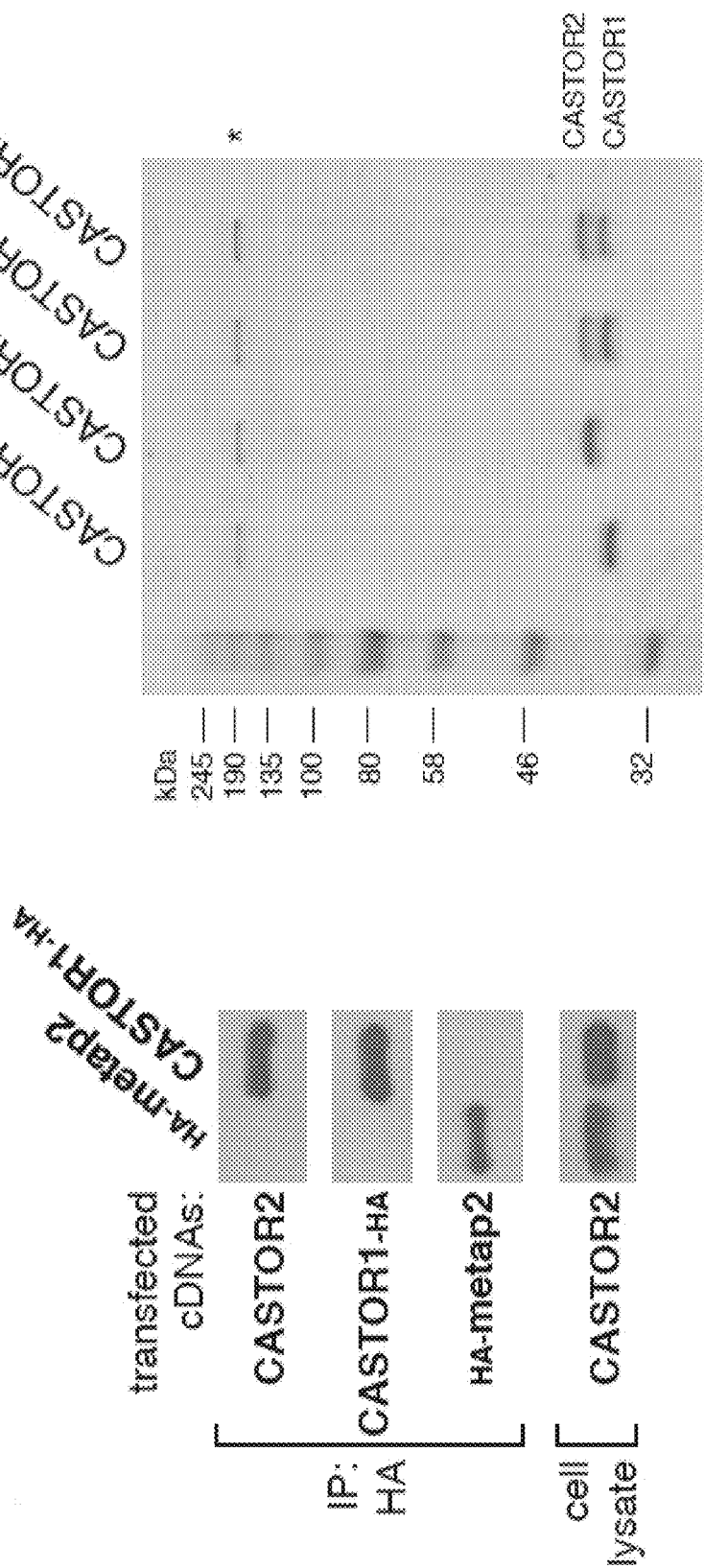

SDS-PAGE followed by Coomassie blue staining showed that CASTOR1 and CASTOR2 associate in a 1:1 ratio within the heterooligomers (FIG. 2D). More definitive methods are needed to determine the exact number of proteins in the complexes, but for simplicity we refer to them as dimers. Altogether, these data support the existence of three CASTOR complexes: the CASTOR1 and CASTOR2 homodimers and the CASTOR1-CASTOR2 heterodimer.

Arginine Regulates the Interaction of the CASTOR1-Homodimer and CASTOR1-CASTOR2 Heterodimer with GATOR2

Figure 3A:
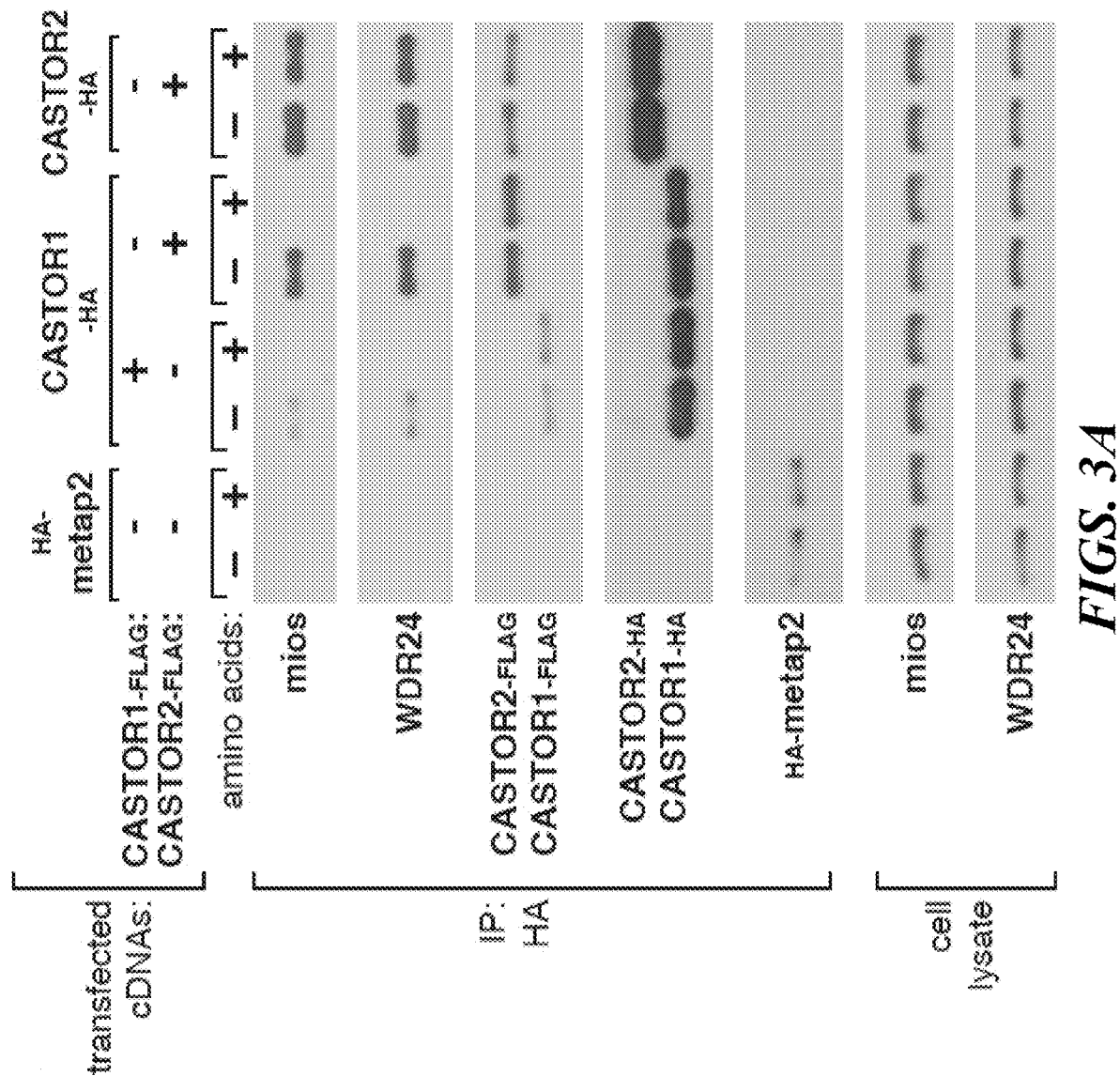
FIG. 3A, FIG. 3B, FIG. 3C, FIG. 3D, FIG. 3E and FIG. 3F depict arginine regulates the interaction of GATOR2 with CASTOR1-homodimers and CASTOR1-CASTOR2 heterodimers in cells and in vitro.

We wondered if the three CASTOR complexes we defined bind differentially to GATOR2. Indeed, when overexpressed in HEK-293T cells, the CASTOR2 homodimer interacted more strongly with endogenous GATOR2 than the CASTOR1 homodimer, while the CASTOR1-CASTOR2 heterodimer bound to GATOR2 at an intermediate level (FIG. 3A). Because endogenous CASTOR2 is present in these cells, it is possible that the GATOR2 interaction, we observe with the CASTOR1 homodimer is partly due to endogenous CASTOR2 that heterodimerizes with overexpressed CASTOR1. However, this is an unlikely possibility because the RNAi-mediated depletion of CASTOR2 did not alter the level of GATOR2 that copurified with CASTOR1 (FIG. 9A).

Because CASTOR1 and CASTOR2 contain ACT domains that have the potential to bind small molecules, we hypothesized that amino acids regulate the CASTOR-GATOR2 interaction in a manner analogous to how leucine controls the Sestrin2-GATOR2 association (Wolfson et al., 2015). Consistent with this prediction, in cells, amino acid withdrawal from the culture medium strengthened the interaction of recombinant CASTOR1-containing dimers with GATOR2 and re-addition of amino acids rapidly disrupted it (FIG. 3A). In contrast, amino acids did not affect the interaction between the CASTOR proteins themselves whether in homo- or heterodimeric complexes (FIG. 3A). Similar to recombinant CASTOR1, endogenous CASTOR1 associated in a highly amino acid-sensitive manner with endogenous GATOR2 isolated from HEK-293T cells with an antibody directed against WDR24, as well as from a HEK-293T cell line expressing endogenously FLAG-tagged WDR59 (FIG. 3B and FIG. 9B).

Figures 3B, 3C:
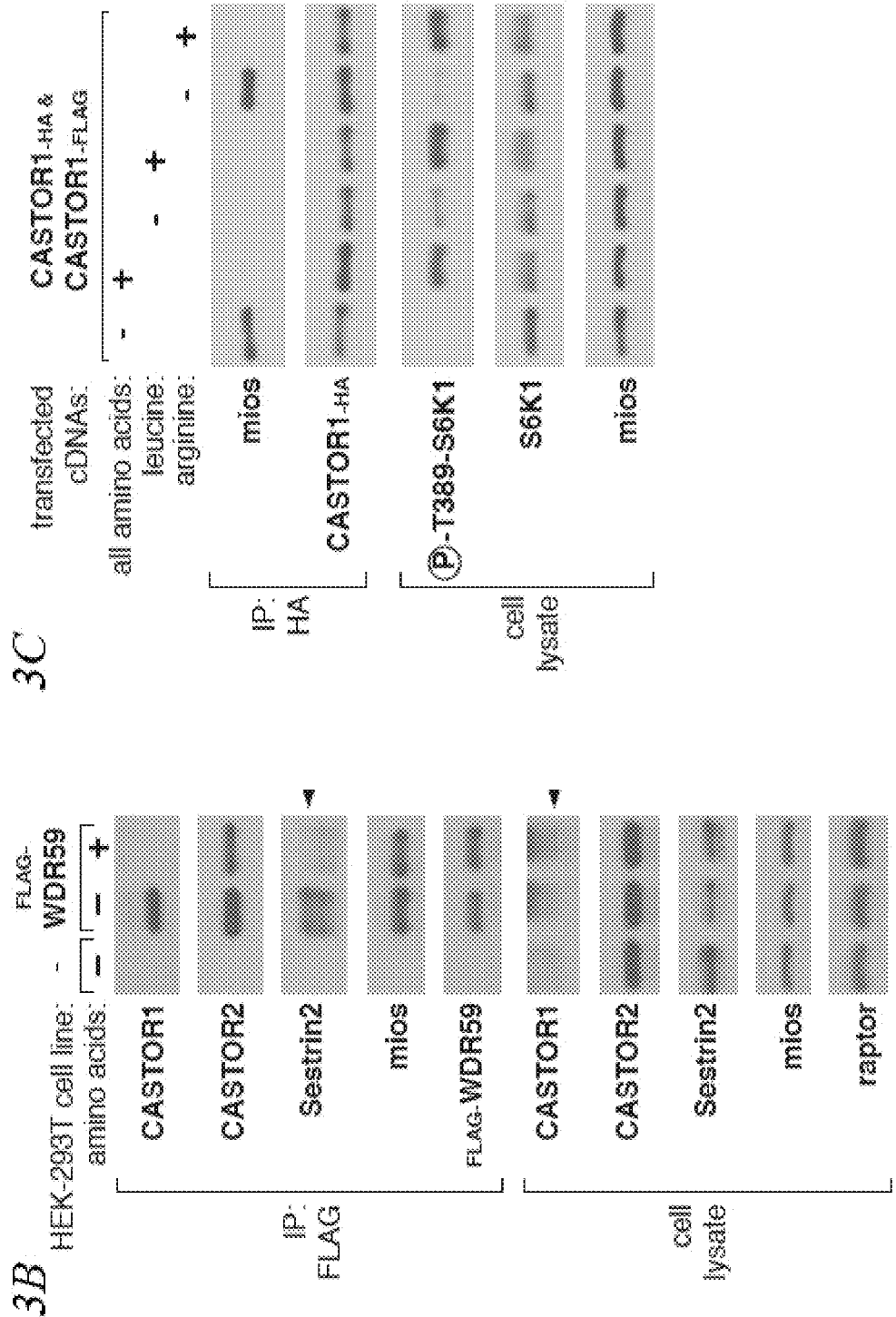
Figures 9A, 9B, 9C:
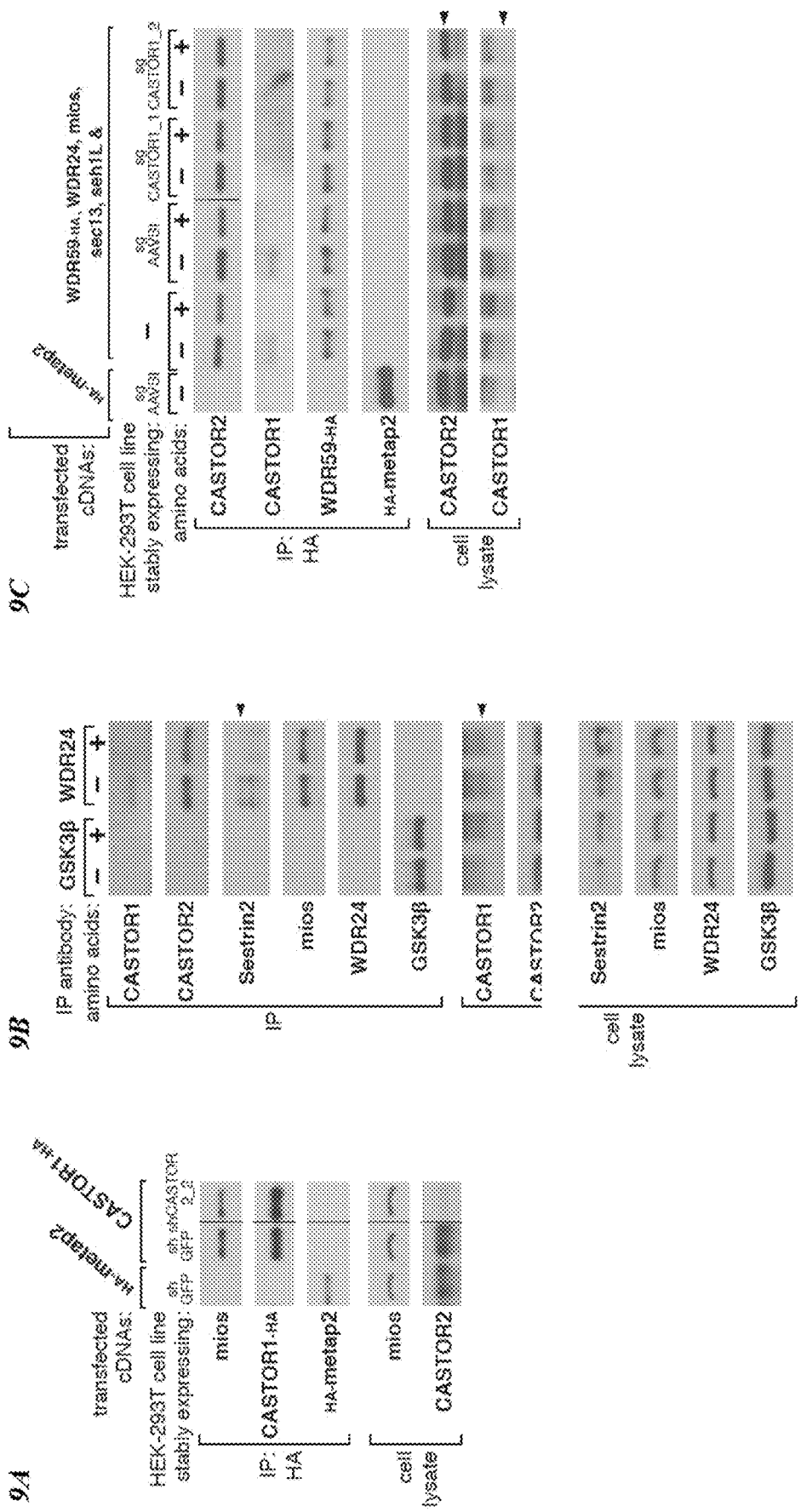
FIG. 9A, FIG. 9B, FIG. 9C, FIG. 9D and FIG. 9E depict arginine regulates the interaction of GATOR2 with CASTOR1-containing complexes in cells and in vitro.

Unlike CASTOR1, amino acids only very weakly regulated the interaction of the CASTOR2 homodimer with GATOR2 (FIGS. 3A and 3B, FIG. 9B). We suspected that the slight amino acid sensitivity of this complex might stem from the small fraction of CASTOR2 that binds to endogenous CASTOR1, thus forming an amino acid-responsive heterodimer. To test this possibility, we immunoprecipitated CASTOR2-GATOR2 complexes from cells depleted of CASTOR1 by stable coexpression of Cas9 and a guide RNA (sgRNA) targeting the CASTOR1 locus. Confirming our suspicions, the CASTOR1 depletion eliminated the weak amino acid sensitivity of the CASTOR2-GATOR2 interaction (FIG. 9C).

Notably, these findings also suggest that the weak interaction we initially detected between GATOR2 and CASTOR1 (FIG. 1D) resulted from isolating these complexes from cells growing in DMEM media, which contains high levels of amino acids that would have disrupted most of the CASTOR1-GATOR2 complexes. In contrast, the CASTOR2-GATOR2 complexes were readily detectable as they are amino acid insensitive.

Figures 9D, 9E:
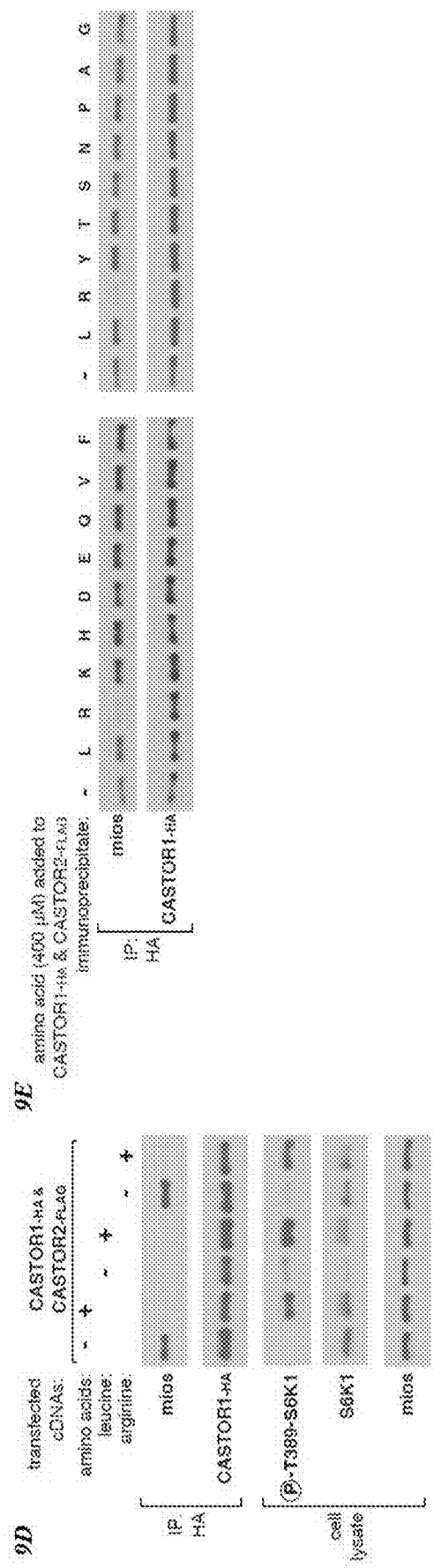

To determine whether a particular amino acid modulates the interaction of CASTOR1 with GATOR2, we focused on leucine and arginine, which have long been known to regulate mTORC1 signaling (Ban et al., 2004; Blommaart et al., 1995; Fox et al., 1998; Hara, 1998; Lynch et al., 2000). In HEK-293T cells, removal of leucine or arginine from the cell medium inhibited mTORC1 signaling to a comparable degree as that of all amino acids, as detected by phosphorylated S6K1, an established mTORC1 substrate (FIG. 3C). Despite similar effects on mTORC1 signaling, only arginine removal recapitulated the ability of total amino acid starvation to promote the binding of GATOR2 to CASTOR1-containing complexes. Re-stimulation with arginine completely reversed the interaction (FIG. 3C and FIG. 9D).

Figures 3D, 3E:
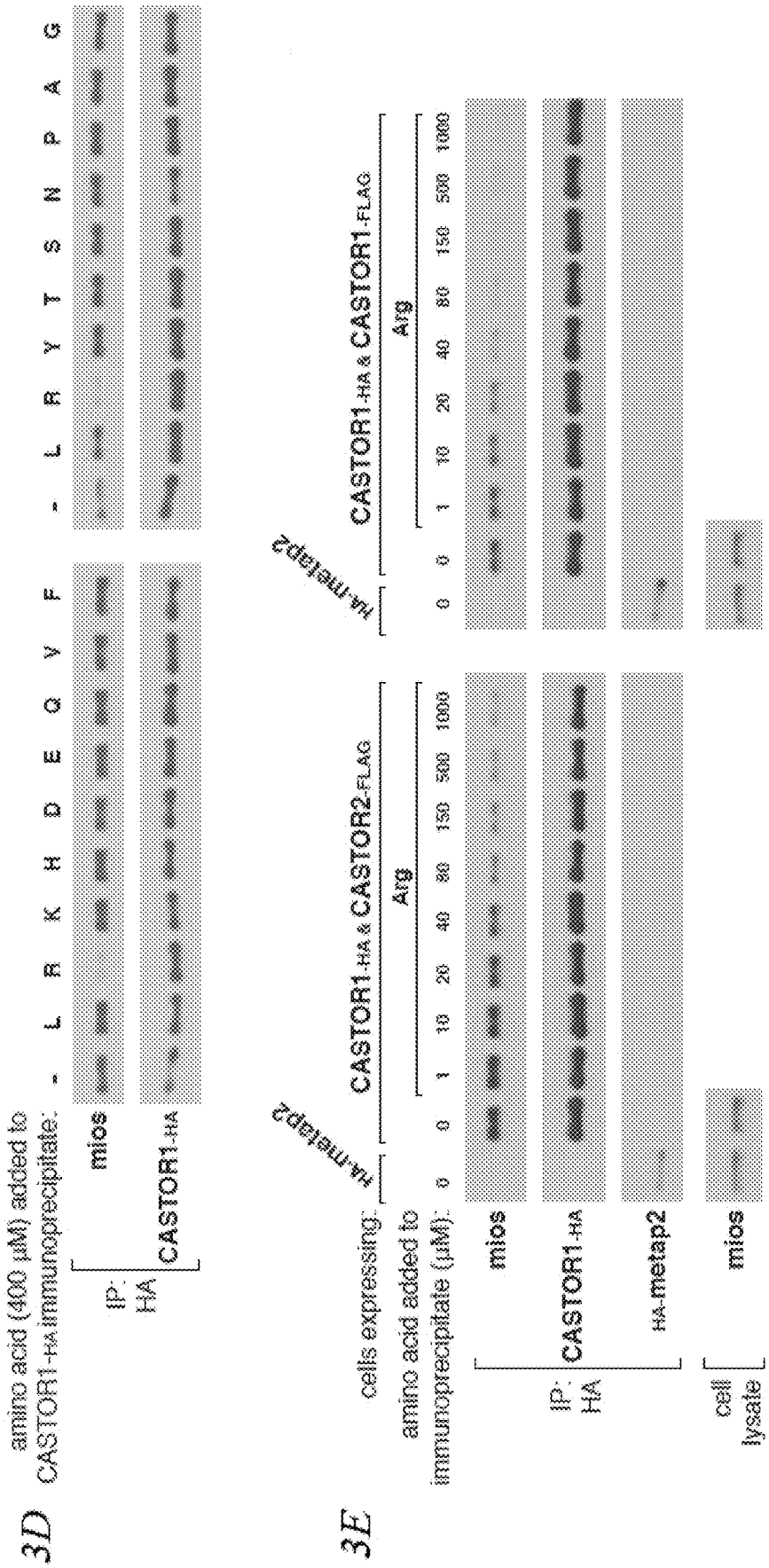

Because CASTOR1 contains ACT domains, we considered the possibility that arginine might act directly on CASTOR1 to perturb its interaction with GATOR2. First, we assessed whether arginine could disrupt the interaction between CASTOR1 and GATOR2 immunopurified from amino acid starved cells. Indeed, the addition of 400 µM arginine to these purified complexes was sufficient to dissociate GATOR2 from both the CASTOR1 homodimer and CASTOR1-CASTOR2 heterodimer, with half-maximal disruption occurring at an arginine concentration of 20-40 µM (FIGS. 3D and 3E and FIG. 9E). Arginine does so with remarkable specificity as none of the other 16 amino acids tested had the same effect.

Figure 3F:
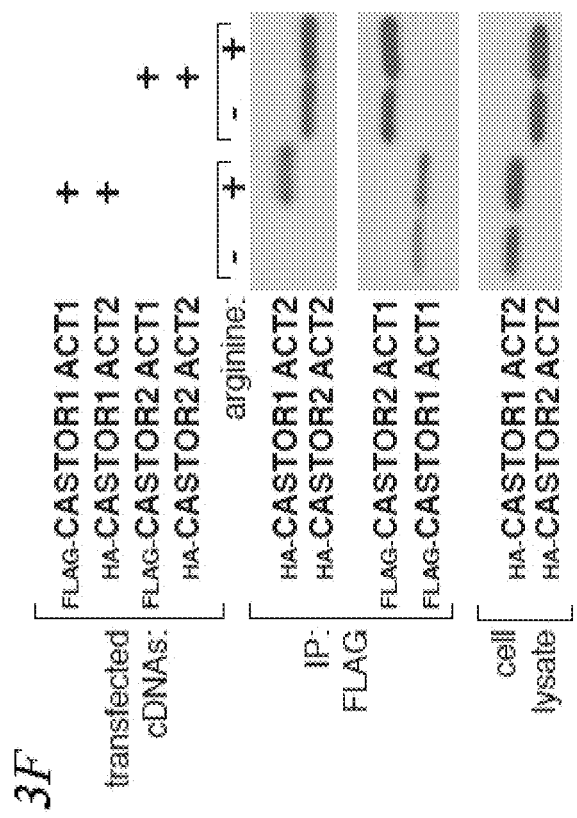

In light of previous structural studies that reveal ligand-induced association of ACT domains (Cross et al., 2013; Cross et al., 2011; Lang et al., 2014; Tan et al., 2008), we tested whether arginine might mediate its effects on CASTOR1 by regulating the interaction between its ACT domains. We divided the CASTOR proteins in half to generate two ACT domain-containing fragments denoted as ACT1 and ACT2, and performed co-immunoprecipitation analyses in arginine-starved and—replete cells. Intriguingly, the CASTOR1 ACT domains interact with each other only when arginine is present, with arginine withdrawal from the cell medium leading to rapid dissociation of the two CASTOR1 halves. In contrast, the CASTOR2 ACT domains bound constitutively to each other, irrespective of arginine (FIG. 3F). These data are consistent with the notion that differences between the CASTOR1 and CASTOR2 ACT domains underlie the ability of arginine to regulate the interaction of GATOR2 with CASTOR1, but not CASTOR2. Taken together these data reveal a role for arginine as a regulator of the CASTOR1-GATOR2 interaction.

Figure 4A:
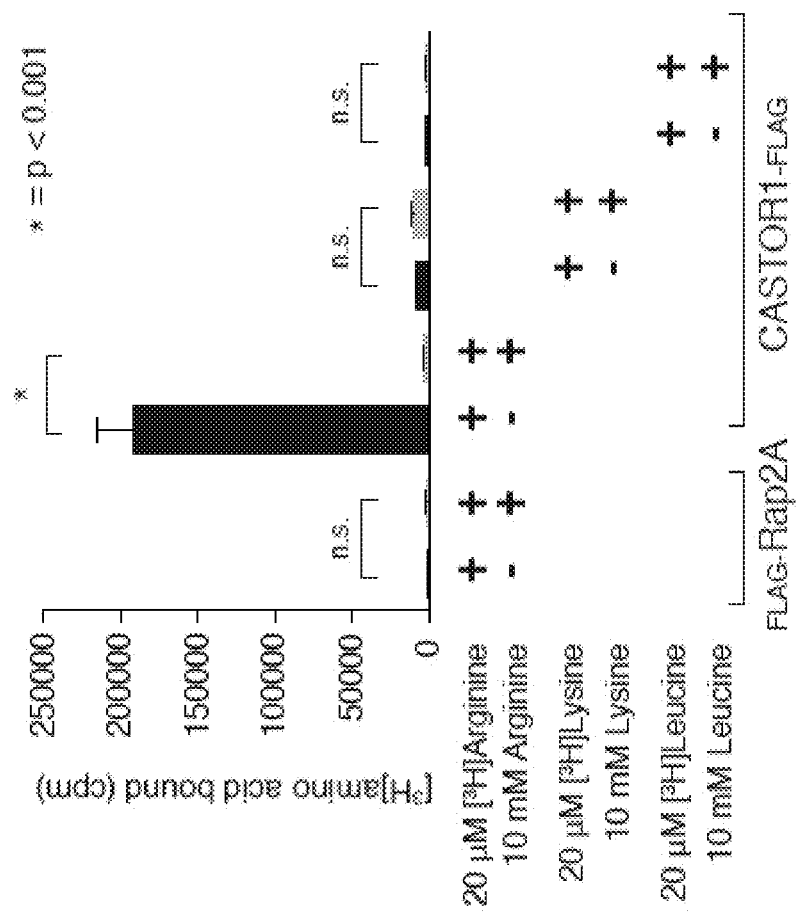
FIG. 4A, FIG. 4B, FIG. 4C, FIG. 4D, FIG. 4E and FIG. 4F depict CASTOR1 homodimer and CASTOR1-CASTOR2 heterodimer bind arginine with a $K_d$ of around 30 µM.
Figure 4B:
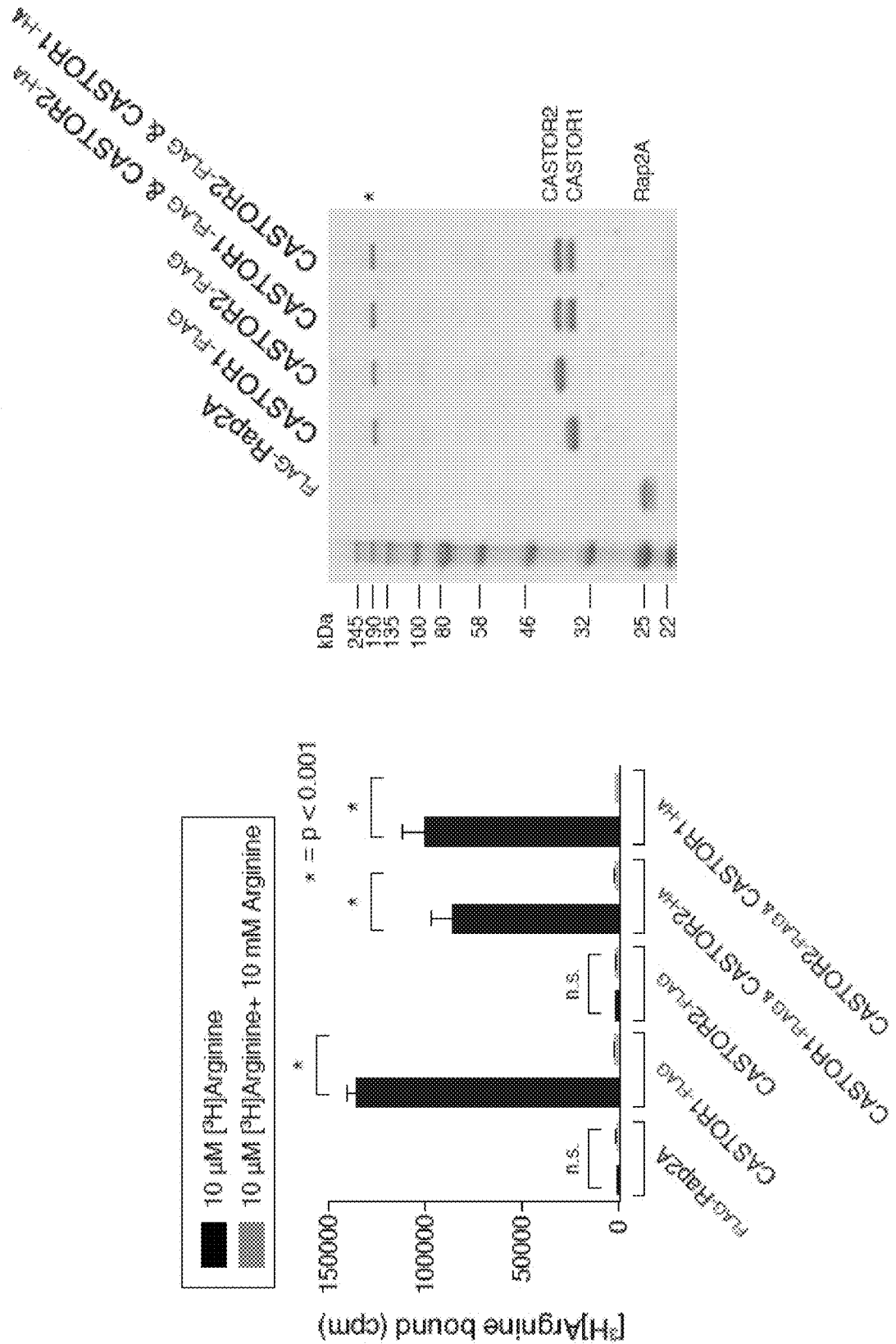

The CASTOR1 Homodimer and CASTOR1-CASTOR2 Heterodimer Bind Arginine with a Dissociation Constant of Around 30 µM Because arginine specifically disrupts the purified CASTOR1-GATOR2 complex and modulates the interaction between the CASTOR1 ACT domains, we tested the possibility that arginine directly binds to CASTOR1. We used an equilibrium binding assay to assess whether immunopurified CASTORs from HEK-293T cells bind radiolabeled arginine. Indeed, tritiated arginine bound the CASTOR1 homodimer, but not the CASTOR2 homodimer or a control protein Rap2A, in a manner that was competed by excess nonradiolabelled arginine (FIGS. 4A and 4B). The CASTOR1-CASTOR2 heterodimer bound roughly half as much arginine as the CASTOR1 homodimer, reflecting the fact that within this complex only CASTOR1 can bind arginine (FIG. 4B). Furthermore, neither radiolabeled leucine nor lysine bound to CASTOR1, consistent with the previously observed specificity for arginine for disrupting the CASTOR1-GATOR2 complex (FIG. 4A).

Figure 4C:
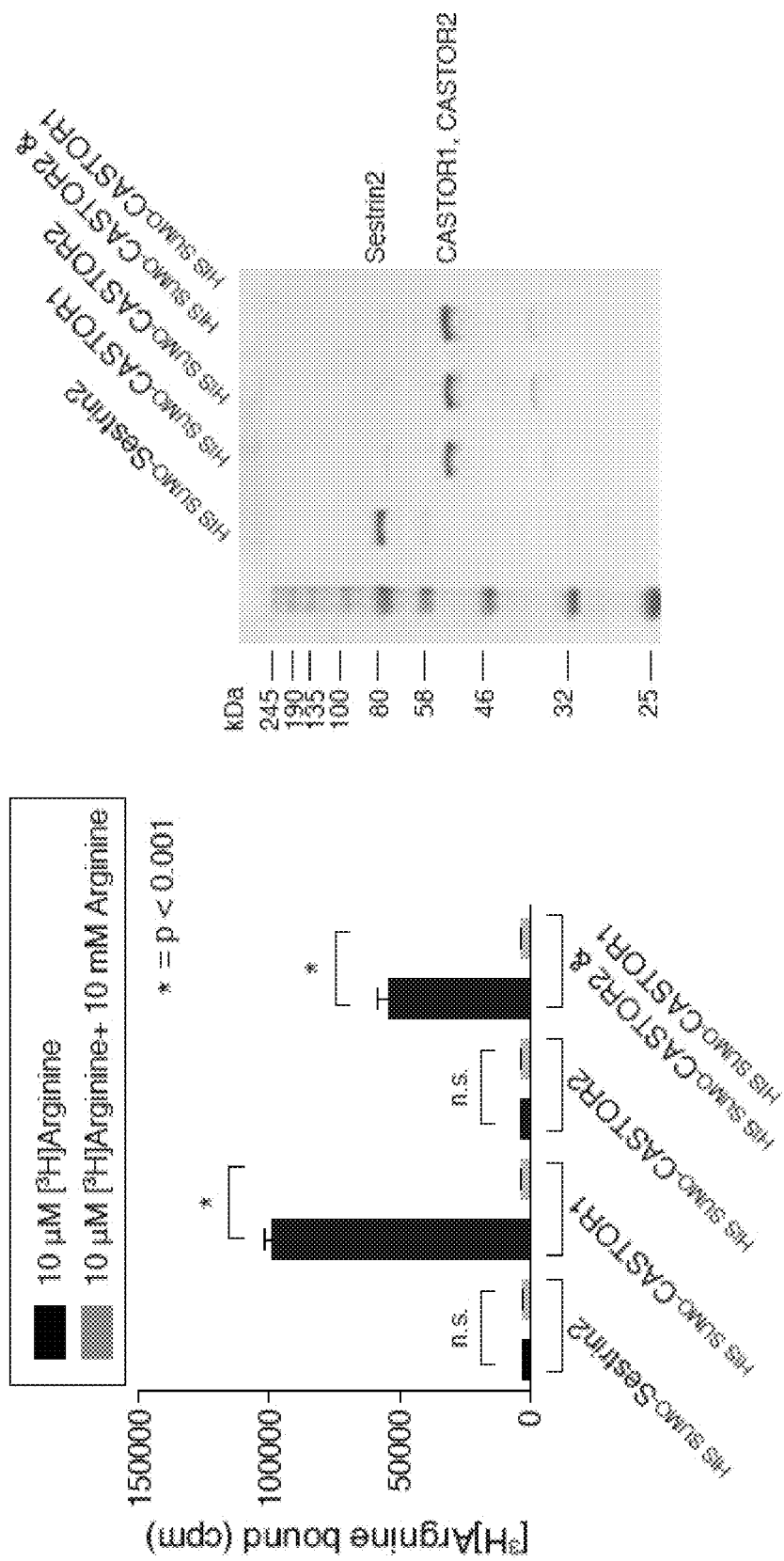

It remained a formal possibility that arginine binds to an unidentified protein in the mammalian preparations of the CASTOR1 homodimer and CASTOR1-CASTOR2 heterodimer. To provide orthogonal evidence that CASTOR1 binds arginine, we purified the CASTOR complexes from *E. coli*, which do not encode a CASTOR homolog. The CASTOR1 homodimer and heterodimer, but not Sestrin2, bound arginine to a comparable degree as the complexes prepared from human cells, demonstrating that arginine binds directly to CASTOR1 and not a co-purifying contaminating protein (FIG. 4C).

Figure 4D:
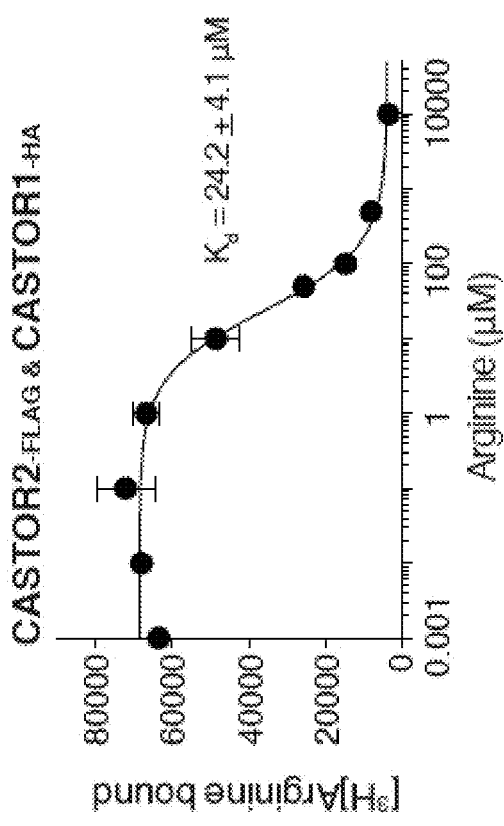
Figure 4E:
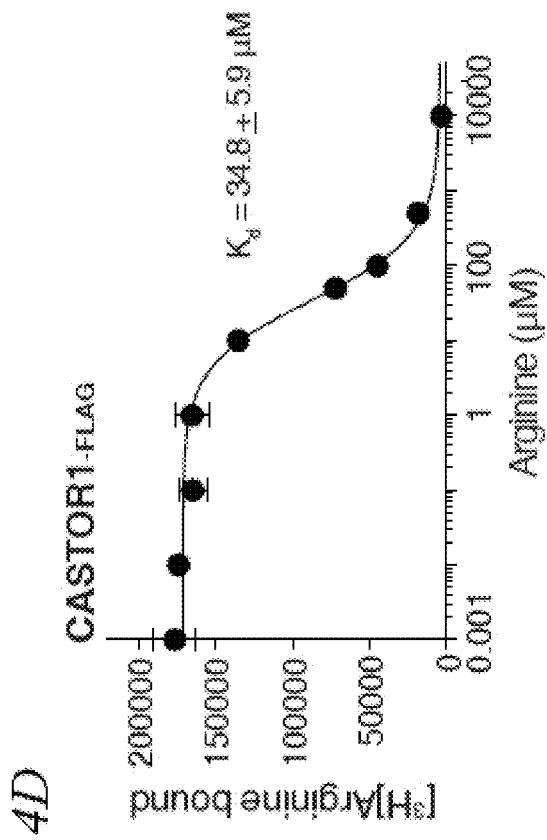
Figure 4F:
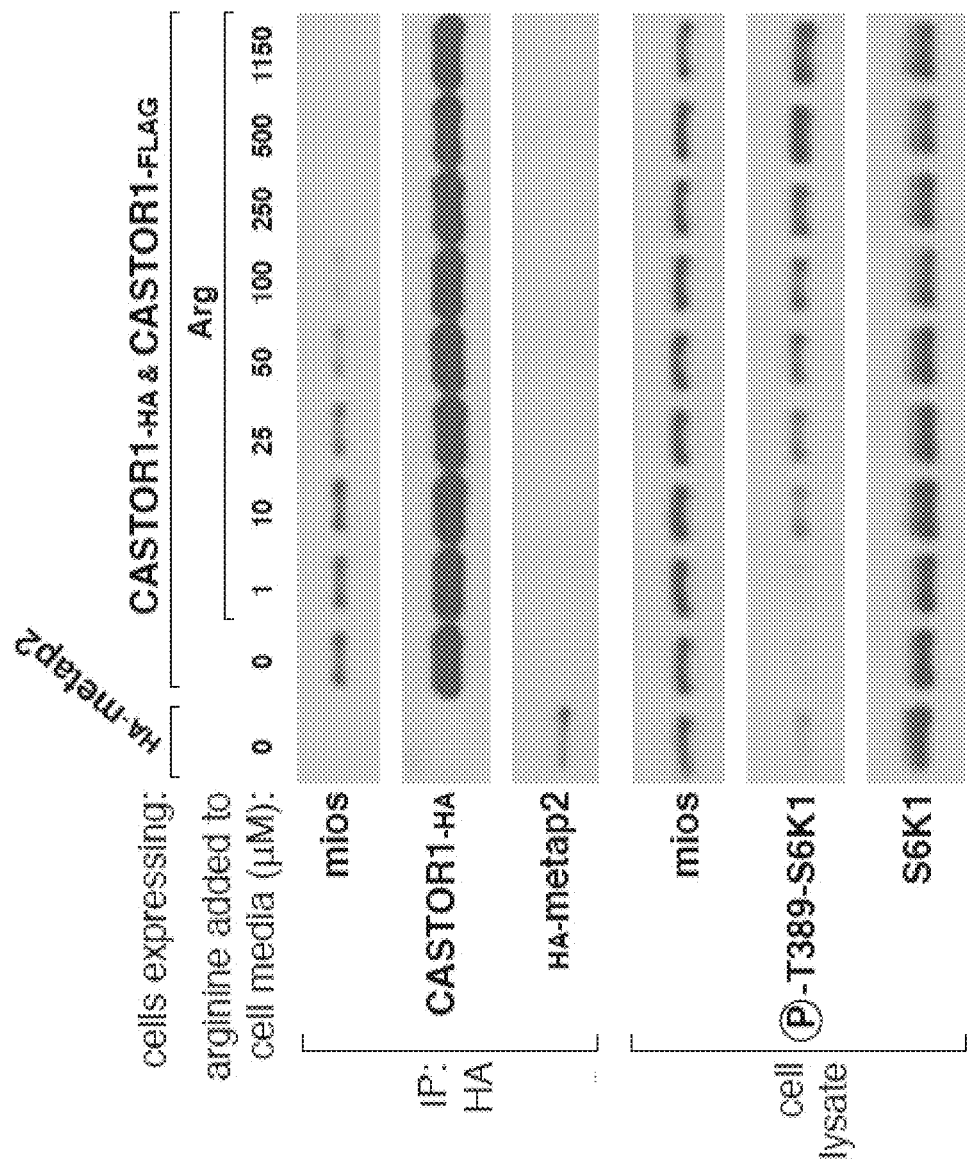
Figure 10:
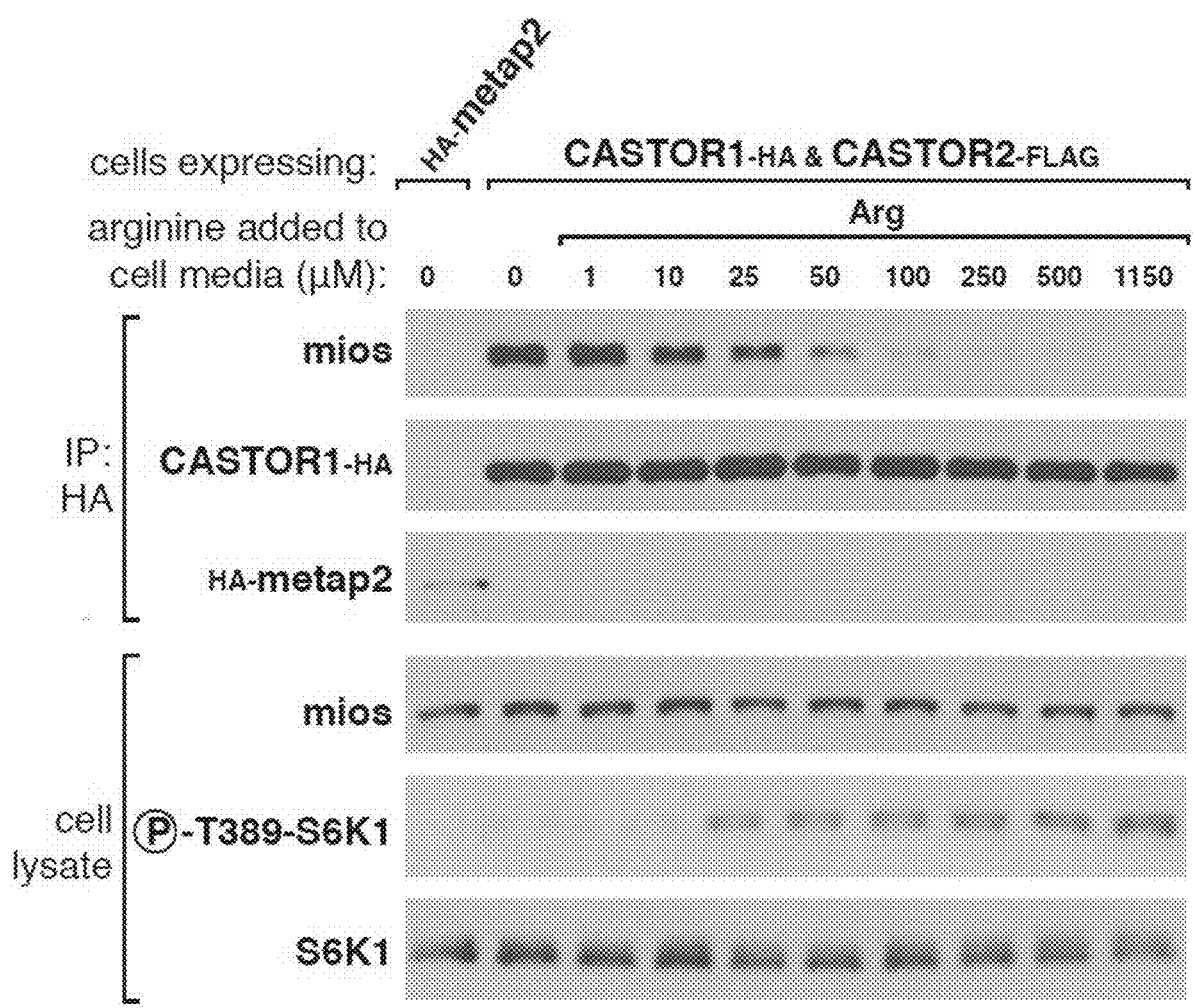
FIG. 10 depicts CASTOR1 homodimer and CASTOR1-CASTOR2 heterodimer bind arginine with a $K_d$ of around 30 µM. The concentration of arginine required to half-maximally activate the mTORC1 pathway correlates with the concentration required to disrupt half the complexes of GATOR2 and CASTOR1-CASTOR2 heterodimers. HEK-293T cells were transfected with the indicated cDNAs and immunoprecipitates and lysates analyzed as in FIG. 3C.

A competition binding assay with increasing amounts of cold arginine revealed that the $K_d$ of arginine for CASTOR1 in the homodimer is 34.8±5.9 µM, which is similar to its $K_d$ in the heterodimer of 24.2±4.1 µM (FIGS. 4D and 4E). These affinities correlate well with the half maximal concentration of arginine that disrupts the interaction of GATOR2 with CASTOR1-containing complexes in vitro (FIG. 3E) and activates mTORC1 in cells (FIG. 4F and FIG. 10). In combination, these data strongly support the notion that arginine binds directly to CASTOR1 to regulate its interaction with GATOR2.

CASTOR1 Functions in Parallel with SLC38A9 to Regulate Arginine Sensing by mTORC1

Figure 5A:
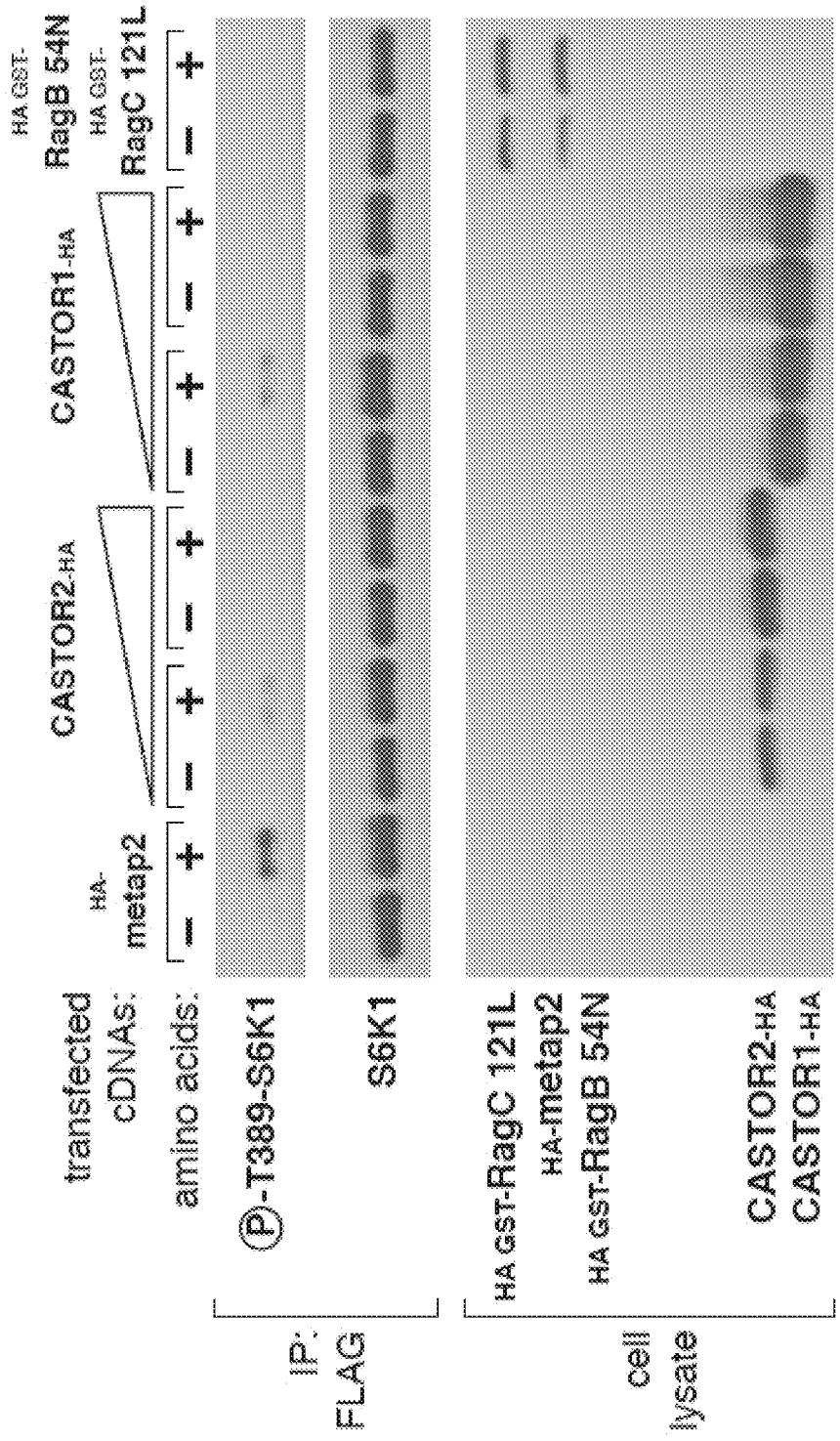
FIG. 5A, FIG. 5B, FIG. 5C, FIG. 5D and FIG. 5E depict CASTOR1 functions in parallel with SLC38A9 to regulate arginine signaling to mTORC1.

Given the ability of arginine to bind to CASTOR1 and to modulate its interaction with GATOR2, we reasoned that CASTOR1 can affect the capacity of the mTORC1 pathway to respond to arginine. Indeed, transient overexpression of CASTOR1 driven by the strong CMV promoter inhibited mTORC1 activation by amino acids to a similar extent as expression of the dominant negative Rag GTPases mutants (FIG. 5A).

Figures 5B, 5C:
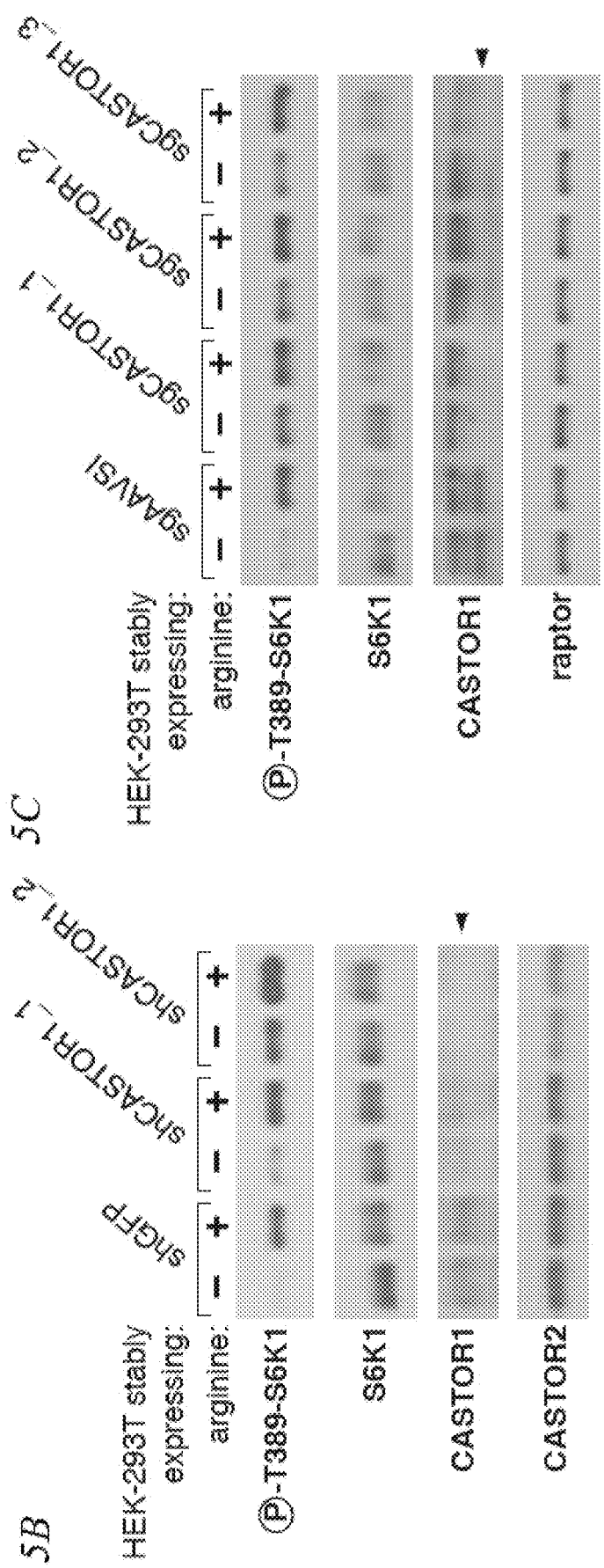
Figures 11A, 11B:
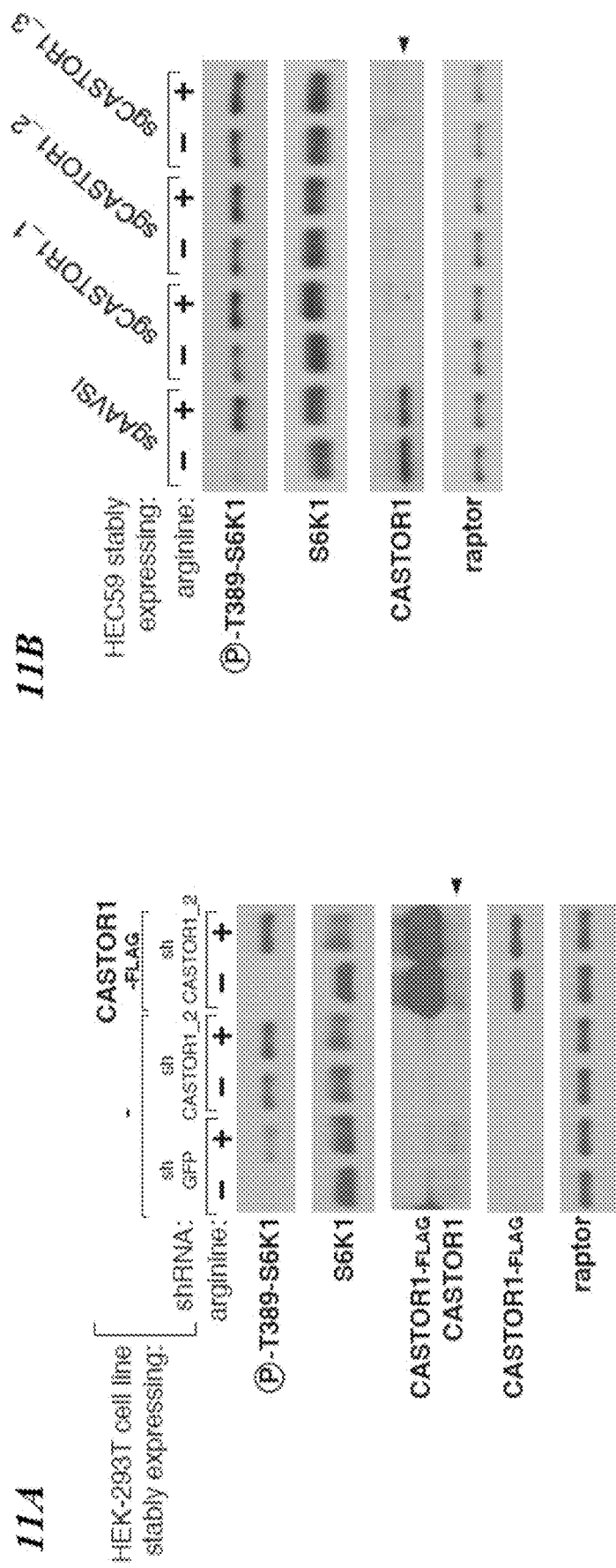
FIG. 11A, FIG. 11B and FIG. 11C depict CASTOR1 functions as a negative regulator of arginine signaling to mTORC1.

Conversely, in HEK-293T and HEC59 cells, CASTOR1-depletion mediated by expression of either shRNAs or Cas9 with sgRNAs made the mTORC1 substantially insensitive to arginine deprivation (FIGS. 5B and 5C and FIG. 11B). To determine if the RNAi-mediated effects are on target, we stably expressed an RNAi-resistant CASTOR1 cDNA in the CASTOR1 knockdown cells. To avoid inhibition of the mTORC1 pathway, we used the Sestrin2 promoter to express CASTOR1 at levels lower than those obtained with the CMV promoter. At this reduced level of expression, reintroduction of CASTOR1 into the CASTOR1 knockdown cells restored the arginine responsiveness of the mTORC1 pathway, demonstrating that the RNAi effects are on target (FIG. 11A). Despite the use of a weaker promoter, the level of recombinant CASTOR1 still greatly exceeded that of the endogenous protein (FIG. 11A). However, this fact does not alter our conclusions because the overexpressed CASTOR1 restored, not inhibited, the arginine responsiveness of the mTORC1 pathway. Overall, these findings indicate that CASTOR1 is a negative regulator of the mTORC1 pathway.

Figure 11C:
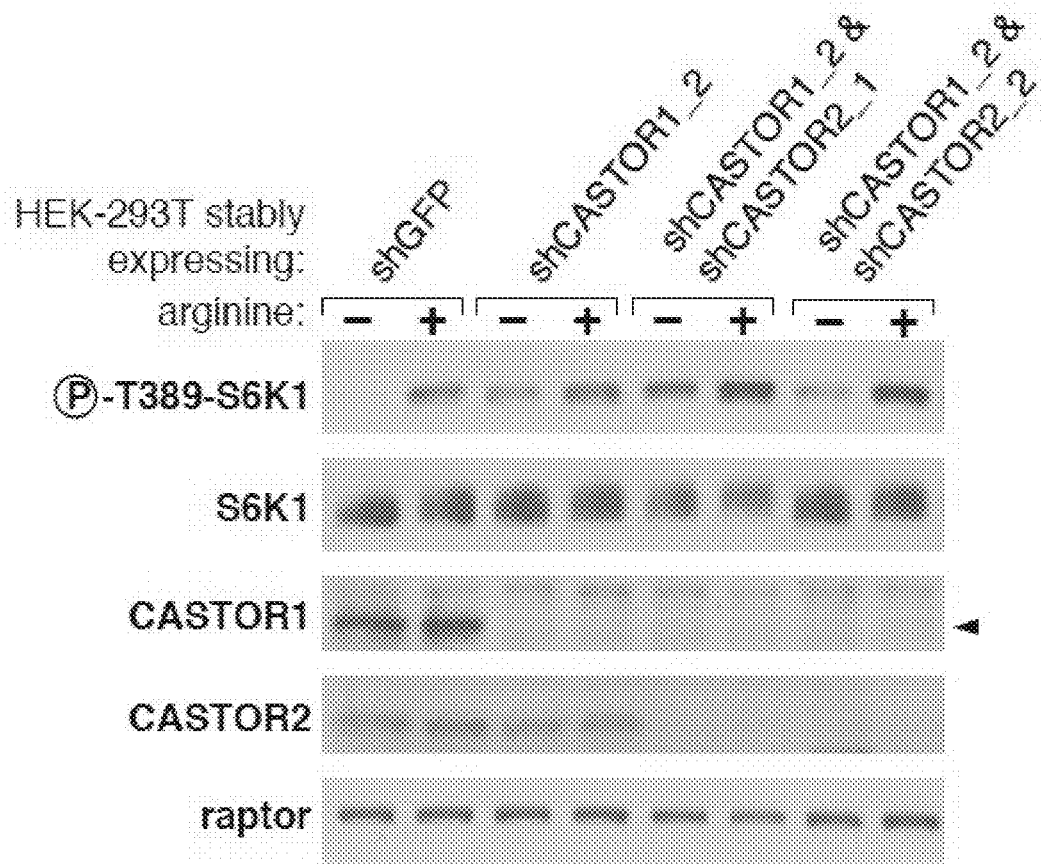

Unlike CASTOR1, CASTOR2 constitutively associates with GATOR2 and does not bind arginine, and thus appears to be an arginine-insensitive version of CASTOR1. RNAi-mediated depletion of CASTOR2 slightly increased mTORC1 activity in the arginine-replete conditions (FIG. 5D), and the knockdown of CASTOR2 together with that of CASTOR1 had a similar effect (FIG. 11C). These results support the notion that CASTOR2, due to its inability to bind to arginine, dampens mTORC1 activity when arginine is present. However, under arginine withdrawal, loss of CASTOR2 does not affect mTORC1 activity because CASTOR1 is still present to inhibit the mTORC1 pathway. Further corroborating an inhibitory role for CASTOR2, its transient overexpression abrogated mTORC1 activation by amino acids even more potently than overexpression of CASTOR1 (FIG. 5A). Thus, both CASTOR1 and CASTOR2 are negative regulators of arginine signaling to mTORC1.

Figures 5D, 5E:
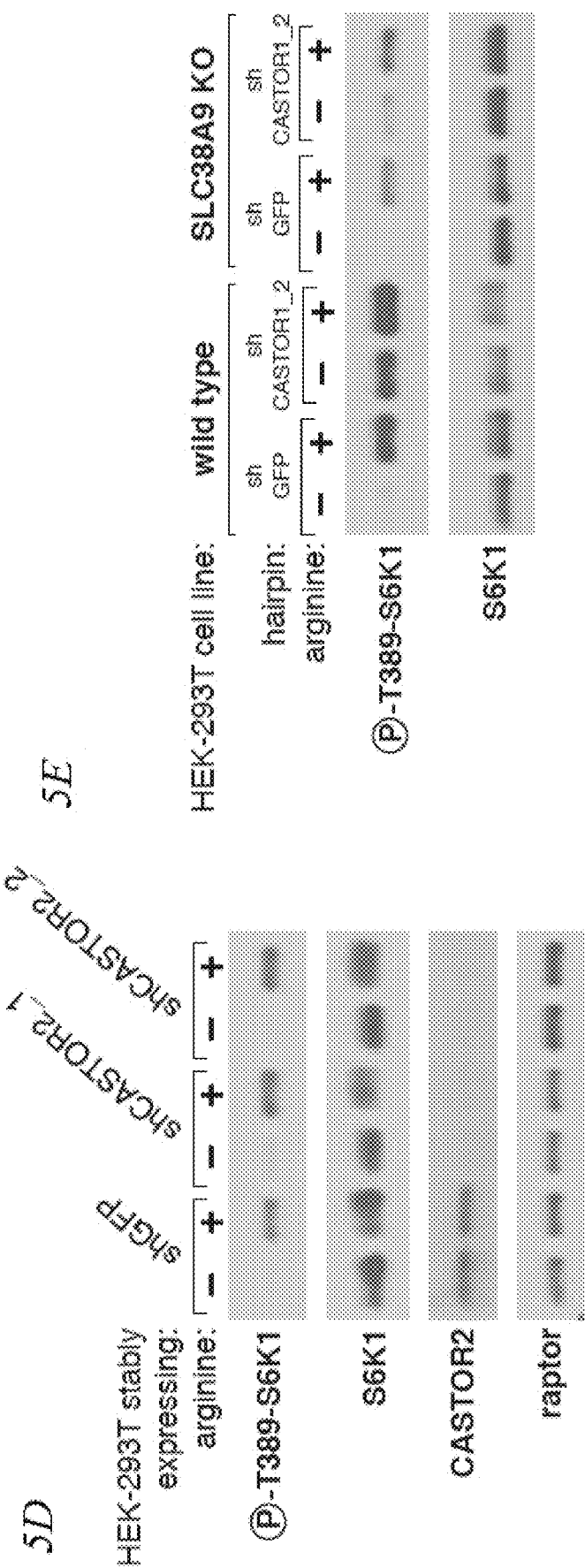

Finally, we probed the relationship between CASTOR1 and SLC38A9, a putative lysosomal arginine sensor that is required to signal the presence of arginine to mTORC1 (Wang et al., 2015). Consistent with the established role of SLC38A9, arginine-induced activation of mTORC1 signaling is severely blunted in HEK-293T cells lacking SLC38A9 (FIG. 5E). RNAi-mediated depletion of CASTOR1 in SLC38A9-null cells renders the mTORC1 pathway insensitive to arginine: cells can neither activate mTORC1 when arginine is present nor inactivate mTORC1 when arginine is withdrawn (FIG. 5E). While other models are possible, it is likely that CASTOR1 and SLC38A9 function in parallel to enable arginine to regulate mTORC1, and in their absence, arginine signaling is almost fully defective.

Arginine Binding to CASTOR1 is Necessary for Arginine to Activate mTORC1

Figure 6A:
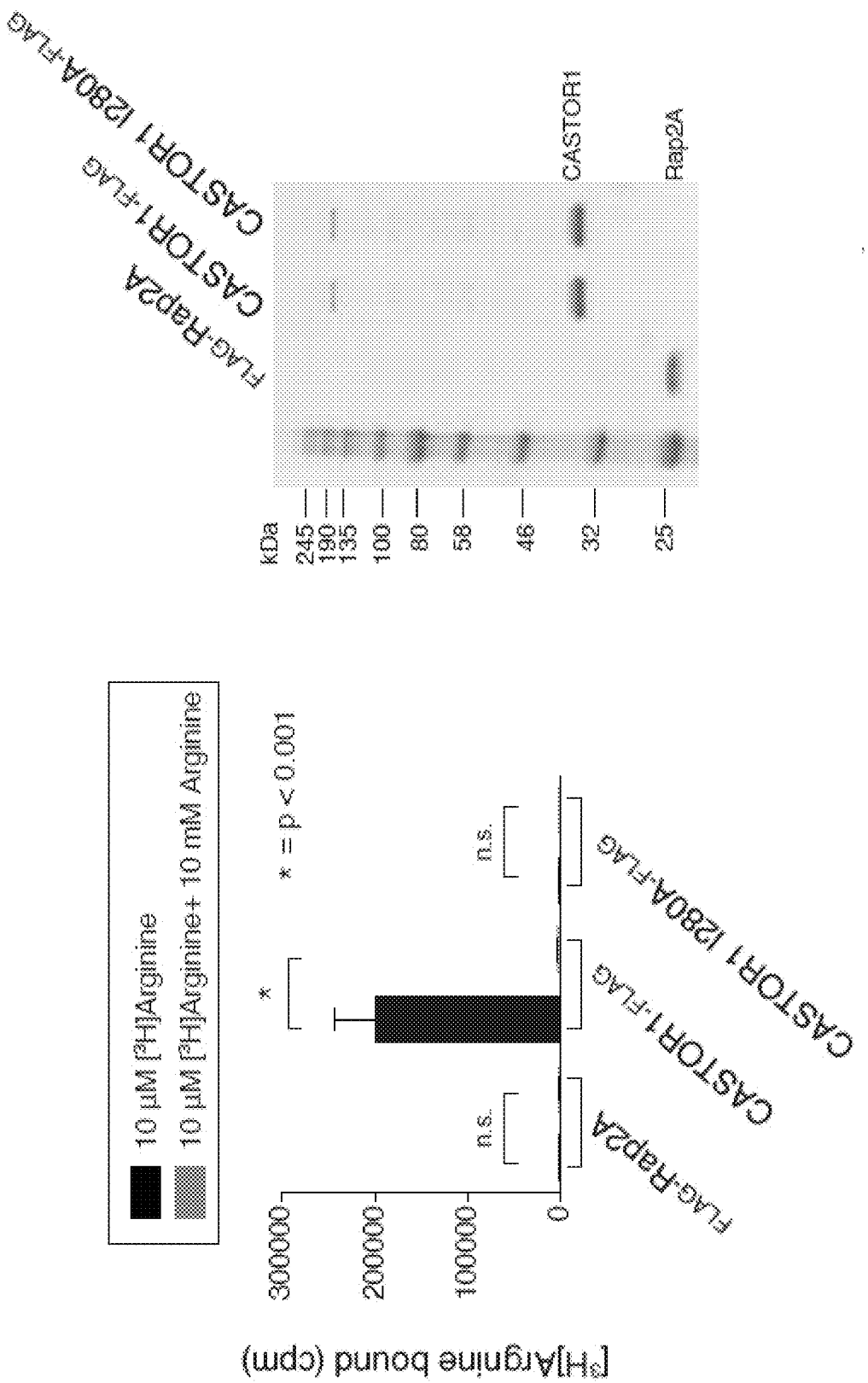
FIG. 6A, FIG. 6B, FIG. 6C and FIG. 6D depict arginine must be able to bind to CASTOR1 for it to activate mTORC1.

To test whether the activation of mTORC1 by arginine requires the arginine-binding capacity of CASTOR1, we used alanine scanning mutagenesis of the CASTOR1 ACT domains to identify CASTOR1 mutants that no longer bind arginine. These efforts led to the identification of 1280A, a mutation within the second ACT domain that fully abrogates the ability of CASTOR1 to bind arginine in vitro (FIG. 6A).

Figure 6B:
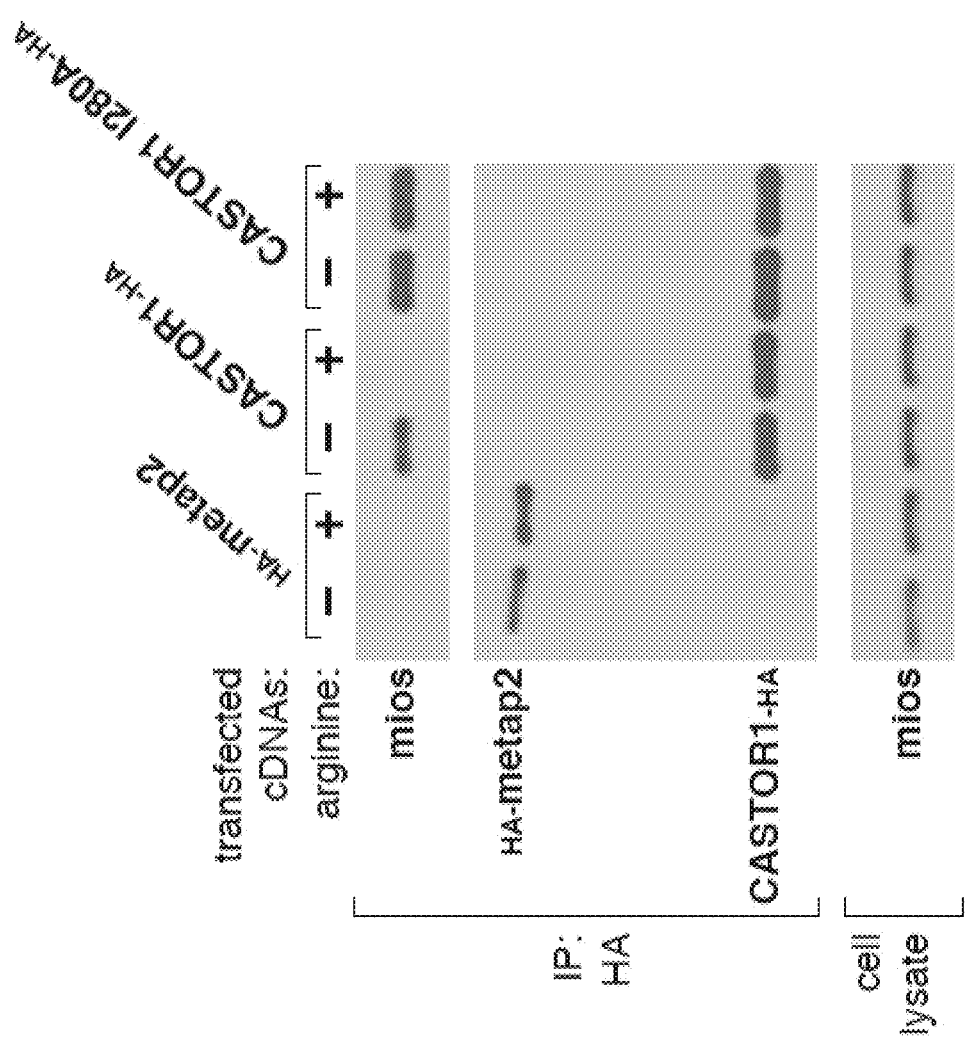

Consistent with the notion that the binding of arginine to CASTOR1 leads to the disruption of the CASTOR1-GATOR2 complex, the arginine-binding mutant of CASTOR1 constitutively associates with GATOR2 in cells, irrespective of arginine levels (FIG. 6B). Notably, this mutant bound more strongly to GATOR2 than its wild type counterpart, confirming that arginine modulates the CASTOR1-GATOR2 interaction. Reflection the importance of this residue in CASTOR1 function, 1280 is highly conserved in orthologs of CASTOR1 and is present in nearly all bacterial and fungal ACT domains that share sequence homology with the CASTOR1 ACT domain (FIG. 1C and FIGS. 7B, 7C and 7D).

Figures 6C, 6D:
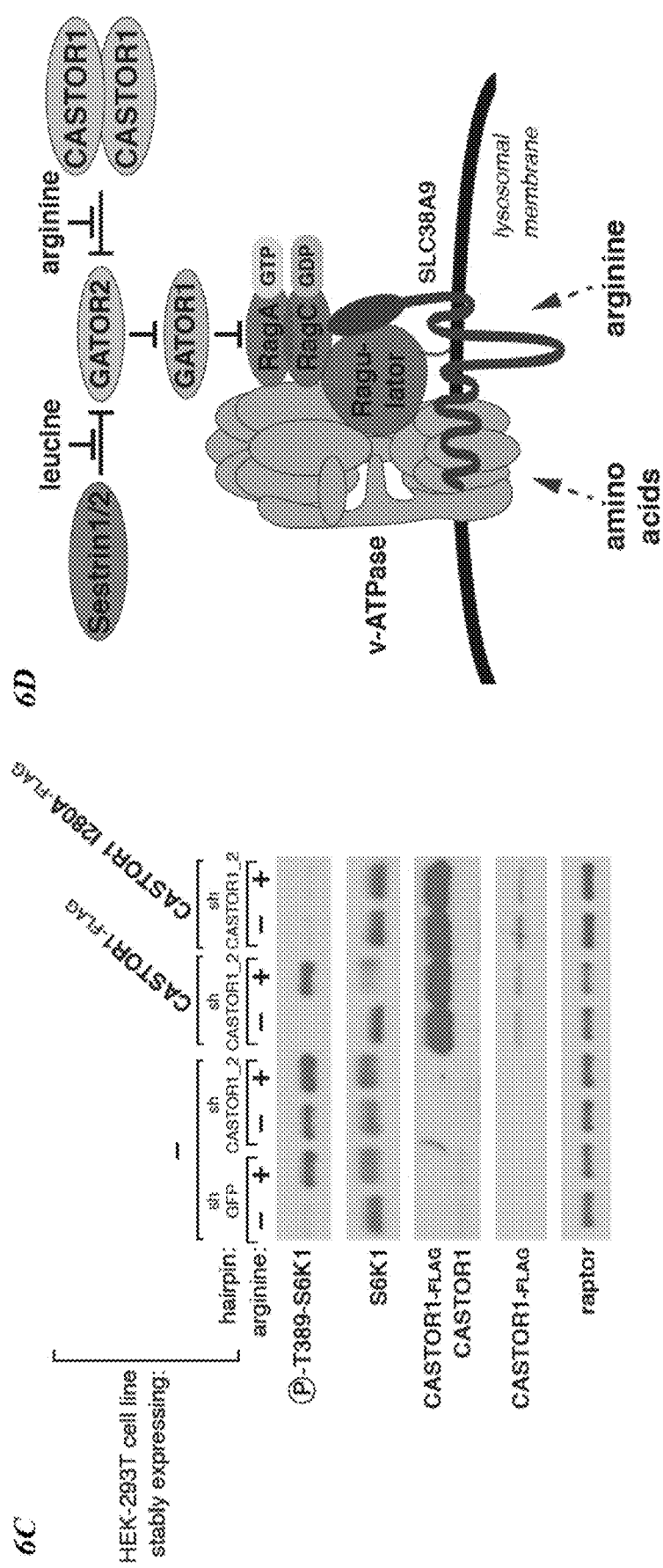

Finally, if CASTOR1 is a bona fide arginine sensor for the mTORC1 pathway, abolishing its ability to bind arginine should in turn abolish the ability of arginine to activate mTORC1 in cells. To test this hypothesis, we compared the arginine sensitivity of the mTORC1 pathway in CASTOR1 knockdown cells that stably expressed either wild type CASTOR1 or the arginine-binding mutant of CASTOR1. Unlike reintroduction of wild type CASTOR1, which restored the ability of arginine to signal to mTORC1, expression of the CASTOR1 arginine-binding mutant rendered the mTORC1 pathway inactive and insensitive to the presence of arginine (FIG. 6C). In combination, these findings establish that arginine must bind to CASTOR1 in order for the mTORC1 pathway to respond to arginine.

DISCUSSION

We establish the CASTOR1 homodimer and CASTOR1-CASTOR2 heterodimer as arginine sensors for the mTORC1 pathway. First, arginine binds to both complexes at affinities that are consistent with those that activate mTORC1 in cells. Second, CASTOR1 loss leads to insensitivity of the mTORC1 pathway to arginine deprivation. Third, expression in cells of an arginine-binding mutant of CASTOR1 prevents the mTORC1 pathway from sensing the presence of arginine.

The identification of CASTOR1 and Sestrin1 and 2 as sensors for the mTORC1 pathway reveal that GATOR2 is a critical hub of amino acid sensing, where leucine and arginine signals converge upstream of the Rag GTPases to regulate mTORC1 activity (FIG. 6D). Leucine and arginine have long been appreciated to be important for mTORC1 activation (Ban et al., 2004; Blommaart et al., 1995; Fox et al., 1998; Hara, 1998; Lynch et al. 2000), and our findings highlight differences in how these two amino acids are sensed. The cytosolic Sestrin proteins are likely the primary leucine sensors because their loss confers complete insensitivity of the mTORC1 pathway to leucine deprivation (Saxton et al, 2015; Wolfson et al., 2015). In contrast, arginine sensing appears to be more complex and may have inputs from two distinct cellular compartments. Loss of function experiments suggests that CASTOR1 signals the absence of arginine to inhibit mTORC1. Because CASTOR1 lacks transmembrane domains and signal sequences it is likely a soluble protein that senses free arginine in the cytosol. In contrast, SLC38A9 is needed to signal the presence of arginine, presumably lysosomal, to mTORC1. Together, both proteins appear to form parallel sensing branches that relay arginine availability to mTORC1. In the absence of both CASTOR1 and SLC38A9, arginine no longer has any impact on the activity of the mTORC1 pathway.

Despite these insights, several key questions remain. While CASTOR1 and Sestrin2 both bind to and likely inhibit GATOR2, whether they operate through distinct mechanisms can only be determined once the function of GATOR2 is elucidated. Furthermore, structural studies may illuminate why arginine can bind to CASTOR1, but not CASTOR2, as well as how the binding pocket of CASTOR1 achieves its remarkable specificity for arginine. In addition, in vivo characterization of mice lacking the CASTOR genes will be needed to reveal how arginine sensing varies across tissues and during development. Because arginine differentially regulated each CASTOR complex, altering the expression of CASTOR1 versus CASTOR2 could serve as a means to modulate mTORC1 activity. CASTOR2 appears analogous to Sestrin3, as both are defective in amino acid binding and can constitutively associate with GATOR2 to inhibit mTORC1 signaling. Thus, increased levels of CASTOR2 should dampen mTORC1 signaling in response to arginine, while increased levels of CASTOR1 should sensitize the pathway to arginine.

It is likely that additional amino acid sensors exist to signal the presence of other critical amino acids for mTORC1 activity, such as glutamine (Jewell et al., 2015), as well sensors that mediate the amino acid sensitive events upstream of additional mTORC1 regulators, such as Folliculin/FNIP (Petit et al., 2013; Tsun et al., 2013). Characterizing the evolutionary conservation of the amino acid sensors of the mTORC1/TORC1 pathway will provide insight into how varied are the amino acid inputs that drive mTORC1/TORC1 signaling in diverse organisms. For instance, budding yeast encodes a homology of GATOR2, but not of the Sestrins or CASTORs, hinting at a divergence in the regulation of the upstream components of the nutrient sensing pathway. This divergence may be expected given that yeast, unlike mammals, can synthesize all amino acids and thus must sense the quality and abundance of nitrogen sources rather than the identity and availability of particular amino acids. Further identification and characterization of the amino acid sensors upstream of the Rag GTPases will guide us towards a comprehensive understanding of how nutrients regulate the mTORC1 pathway.

EXPERIMENTAL PROCEDURES

Materials

Reagents were obtained from the following sources: HRP-labeled anti-mouse and anti-rabbit secondary antibodies from Santa Cruz Biotechnology; antibodies to phospho-T389 S6K1, S6K1, Sestrin2, and mios from Cell Signaling Technology; antibody to the HA epitope from Bethyl laboratories; antibody to raptor from Millipore; FLAG M2 antibody, FLAG M2 affinity gel, ATP, and amino acids from Sigma Aldrich; HA magnetic beads and RPMI without leucine, arginine, or lysine from Pierce; DMEM from SAFC Biosciences; XtremeGene9 and Complete Protease Cocktail from Roche; Inactivated Fetal Calf Serum (IFS) from Invitrogen; amino acid-free RPMI from US Biologicals; [$^3$H]-labeled amino acids from American Radiolabeled Chemicals. The WDR24, Mios, CASTOR1, and CASTOR2 antibodies were generously provided by Jianxin Xie (Cell Signaling Technology).

Cell Lines and Tissue Culture

All cell lines were cultured in Dulbecco's modified Eagle's medium (DMEM) with 10% inactivated fetal calf serum supplemented with 2 mM Glutamine. All cell lines were maintained at 37° and 5% $CO_2$.

Preparation of Cell Lysates and Immunoprecipitates

Cell lysate preparation, cell lysis, and immunoprecipitations were performed as described below.

Where indicated, for transient cotransfection experiments, 2 million HEK-293T cells were plated in 10 cm dishes and transfected 24 hrs later using the polyethylenimine method (Boussif et al., 1995) with the indicated pRK5-based expression vectors: 300 ng HA-metap2, 40 ng CASTOR1-HA, 80 ng CASTOR1-FLAG, 40 ng CASTOR2-HA, 80 ng CASTOR2-FLAG; 100 ng WDR24-FLAG, 100 ng WDR59, 100 ng mios, 150 ng sec13, 150 ng seh1L, 10 ng or 40 ng or 100 ng or 600 ng of myc-Sestrin2 or myc-CASTOR2; 2 ng FLAG-56K1, 15 ng or 60 ng HA-CASTOR2, 75 ng and 175 ng of CASTOR1-HA. The total amount of plasmid DNA in each transfection was normalized to 5 µg with empty pRK5. Thirty-six hours after transfection, cells were harvested as described above.

For experiments that required leucine, arginine or amino acid starvation or restimulation, cells were treated as previously described (Wolfson et al., 2015). Briefly, cells were incubated in leucine, arginine, or amino acid free RPMI for 50 minutes and then restimulated with the indicated amino acid(s) for 10 minutes.

Arginine Binding Assay

Four million HEK-293T cells were plated in a 15 cm plate four days prior to the experiment. Forty-eight hours after plating, the cells were transfected via the polyethylenimine method (Boussif et al., 1995) with the pRK5-based cDNA expression plasmids indicated in the figures in the following amounts: 15 µg FLAG-Rap2A, 400 ng CASTOR1-FLAG or CASTOR2-FLAG with 1200 ng CASTOR1-HA or 1200 ng CASTOR2-HA, 400 ng CASTOR1 1280A-FLAG with 1200 ng CASTOR1 1280A-HA. The total amount of plasmid DNA in each transfection was normalized to 15 µg with empty pRK5. Forty-eight hours after transfection cells were lysed as previously described (Wolfson et al., 2015). If multiple samples of the same type were represented in the experiment, the cell lysates were combined, mixed, and evenly distributed amongst the relevant tubes.

Anti-FLAG immunoprecipitates were prepared as previously described, with the exception that prior to incubation with lysates, the beads were blocked by rotating in 1 µg/µl bovine serum albumin (BSA) for 20 minutes at 4° C. and subsequently washed twice in lysis buffer. Thirty µl of the 50% slurry of beads in lysis buffer was added to each of the clarified cell lysates and incubated for 90 minutes.

For the binding assays, all immunoprecipitates were washed in pairs once with Triton wash buffer, three times with Triton lysis buffer supplemented with 500 mM NaCl, and three times with cytosolic buffer (0.1% Triton, 40 mM HEPES pH 7.4, 10 mM NaCl, 150 mM KCl, 2.5 mM $MgCl_2$). All the liquid was subsequently aspirated and a 15 µl aliquot of proteins bound to the beads was incubated for one hour on ice in cytosolic buffer with the appropriate amount of [$^3$H]-labeled amino acids and cold amino acids. At the end of one hour, the beads were spun at 2,500 rpm for 25 seconds, aspirated, and rapidly washed three times with binding wash buffer (0.1% Triton, 40 mM HEPES pH 7.4, 150 mM NaCl). The beads were aspirated dry and resuspended in 85 µl of binding wash buffer. Three 10 µl aliquots of this mix were separately quantified using a TriCarb scintillation counter (PerkinElmer).

For each sample, an immunoprecipitation was performed in parallel. After washing four times as previously described, the beads were aspirated dry and resuspended in 50 µl FLAG elution buffer (Triton wash buffer supplemented with 300 mM NaCl and 1 mg/ml FLAG peptide), and incubated with rotation for 1 hour at 4° C. The eluent was subsequently resuspended in sample buffer. Equal volumes of the eluent were resolved by 10% SDS-PAGE and analyzed with Coomassie Blue stain. $K_d$ values were calculated as previously described (Wolfson et al., 2015).

In Vitro CASTOR-GATOR2 Dissociation Assay

HEK-293T cells co-transfected with 40 ng CASTOR1-HA and either 80 ng CASTOR1-FLAG (CASTOR1 homodimer) or 80 ng CASTOR2-FLAG (CASTOR1-CASTOR2 heterodimer) were starved for all amino acids for 50 minutes, lysed and subjected to anti-HA immunoprecipitation as described previously. The CASTOR-GATOR2 complexes immobilized on agarose beads were washed once in Triton wash buffer, three times in Triton wash buffer supplemented with 500 mM NaCl, and then incubated for 20 minutes in 1 mL of ice-cold Triton wash buffer supplemented with 500 mM NaCl and the indicated concentrations of individual amino acids. The amount of GATOR2 that remained bound to CASTOR complexes was assayed by SDS-PAGE and immunoblotting as previously described.

Mammalian Lentiviral Production and Transduction

Lentiviral short hairpin RNAs (shRNAs) were obtained from the TRC. Guide RNAs (sgRNAs) targeting CASTOR1, CASTOR2, or a control AAVS1 locus were cloned into pLentiCRISPR v2. The target sequences are described below.

Lentiviruses were produced by transfection of viral HEK-293T cells with either pS2JC6-CASTOR1-FLAG (wild-type or mutant) constructs or shRNA constructs in combination with the VSV-G envelope and CMV AVPR packaging plasmids. Twenty-four hours after transfection, the media was changed to fresh DMEM with 20% IFS. Forty-eight hours after transfection, the virus-containing supernatant was collected from the cells and passed through a 0.45 µm filter. To generate the indicated stable cell lines overexpressing CASTOR1, 300,000 cells were plated in 6-well plates containing 1.5 mls DMEM 10% IFS with 8 µg/mL polybrene and infected with virus containing media. Twenty-four hours later, the media was changed to fresh media containing 5 µg/ml blasticidin for selection.

To generate the indicated knockdown lines, 3 million cells were plated in 6-well plates containing 2 mls DMEM 10% IFS with 8 µg/mL polybrene and infected with virus containing media. Cells were spun at 2,200 rpm for 45 minutes at 37° C. Twelve hours later, the media was changed to fresh DMEM 10% IFS, and 7-10 hours later, cells were trypsinized and selected with puromycin.

Statistical Analysis

Two-tailed t tests were used for comparison between two groups. All comparisons were two-sided, and P values of less than 0.001 were considered to indicate statistical significance.

Sequence Alignments

Indicated protein sequences were obtained from the NCBI protein database and aligned via the T-coffee multiple sequence alignment program on EMBL-EBI. Alignments were annotated using JalView.

Preparation of Cell Lysates and Immunoprecipitates

Cells were rinsed once with ice-cold PBS and immediately lysed with Triton lysis buffer (1% Triton, 10 mM ββ-glycerol phosphate, 10 mM pyrophosphate, 40 mM Hepes pH 7.4, 2.5 mM MgCl$_2$ and 1 tablet of EDTA-free protease inhibitor [Roche] (per 25 ml buffer). The cell lysates were cleared by centrifugation at 13,200 rpm at 4° C. in a microcentrifuge for 8 minutes. For anti-FLAG and anti-HA immunoprecipitations, the FLAG-M2 or HA affinity gel was washed 3 times with Triton wash buffer (1% Triton, 40 mM Hepes pH 7.4, 2.5 mM MgCl$_2$). 30 µl of a 50/50 slurry of the FLAG-M2 affinity gel or 25 µl of the HA affinity gel was then added to clarified cell lysates and incubated with rotation for 90 minutes at 4° C. Following immunoprecipitation, the beads were washed one time with Triton wash buffer and 3 times with Triton wash buffer containing 500 mM NaCl. Immunoprecipitated proteins were denatured by the addition of 50 µl of sample buffer, resolved by 8%-16% SDS-PAGE, and analyzed by immunoblotting.

Mammalian Lentiviral Production and Transduction

To generate HEK-293T cells with RNAi-mediated loss of CASTOR2 and/or CASTOR1, the following shRNAs were transfected into viral HEK-293 Ts:

Human shCASTOR1_1: TRCN0000284010
Human shCASTOR1_2: TRCN0000269399
Human shCASTOR2_1: TRCN0000352396
Human shCASTOR2_2: TRCN0000337256
Human shCASTOR2_3: TRCN0000352387

The following sense (S) and antisense (AS) oligonucleotides encoding the guide RNAs were cloned into a pLentiCRISPR vector:

```
sgCASTOR1_1S:
                                           (SEQ ID NO: 1)
caccgTGTAGAGCCAGAGACCGGGA sgCASTOR1_1AS:
                                           (SEQ ID NO: 2)
aaacTCCCGGTCTCTGGCTCTACAc sgCASTOR1_2S:
                                           (SEQ ID NO: 3)
caccgGAGCAGCTTGATGAGCGGGT sgCASTOR1_2AS:
                                           (SEQ ID NO: 4)
aaacACCCGCTCATCAAGCTGCTCc sgCASTOR1_3S:
                                           (SEQ ID NO: 5)
caccgGACACGTGGTGCTCGGCCAG sgCASTOR1_3AS:
                                           (SEQ ID NO: 6)
aaacCTGGCCGAGCACCACGTGTCc
```

REFERENCES

Aravind, L., and Koonin, E. V. (1999). Gleaning non-trivial structural, functional and evolutionary information about proteins by iterative database searches. Journal of Molecular Biology 287, 1023-1040.

Ban, H., Shigemitsu, K., Yamatsuji, T., Haisa, M., Nakajo, T., Takaoka, M., Nobuhisa, T., Gunduz, M., Tanaka, N., and Naomoto, Y. (2004). Arginine and Leucine regulate p70 S6 kinase and 4E-BP1 in intestinal epithelial cells. International journal of molecular medicine 13, 537-543.

Bar-Peled L., Chantranupong, L., Cherniack, A. D., Chen, W. W., Ottina, K. A., Grabiner, B. C., Spear, E. D., Carter, S. L., Meyerson, M., and Sabatini, D. M. (2013). A Tumor Suppressor Complex with GAP Activity for the Rag GTPases That Signal Amino Acid Sufficiency to mTORC1. Science 340, 1100-1106.

Bar-Peled L., Schweitzer L. D., Zoncu R., & Sabatini D. M. Ragulator is a GEF for the rag GTPases that signal amino acid levels to mTORC1. Cell 150, 1196-208 (2012).

Blommaart, E. F. C., Luiken, J. J. F. P., Blommaart, P. J. E., van Woerkom, G. M., and Meijer, A. J. (1995). Phosphorylation of Ribosomal Protein S6 Is Inhibitory for Autophagy in Isolated Rat Hepatocytes. Journal of Biological Chemistry 270, 2320-2326.

Boussif, O., Lezoualc'h, F., Zanta, M. A., Mergny, M. D., Scherman, D., Demeneix, B., and Behr, J. P. (1995). A versatile vector for gene and oligonucleotide transfer into cells in culture and in vivo: polyethylenimine. Proceedings of the National Academy of Sciences of the United States of America 92, 7297-7301.

Buerger, C., DeBries, B., and Stambolic, V. (2006). Localization of Rheb to the endomembrane is critical for its signaling function. Biochemical and Biophysical Research Communications 344, 869-880.

Carluccio, C., Fraternali, F., Salvatore, F., Fomili, A., and Zagari, A. (2013). Structural Features of the Regulatory ACT Domain of Phenylalanine Hydroxylase. PLOS ONE 8, e79482.

Chantranupong, L., Wolfson, R. L., Orozco, J. M., Saxton, R. A., Scaria, S. M., Bar-Peled, L., Spooner, E., Isasa, M., Gygi, S. P., and Sabatini, D. M. (2014). The Sestrins Interact with GATOR2 to Negatively Regulate the Amino-Acid-Sensing Pathway Upstream of mTORC1. Cell Reports 9, 1-8.

Chipman, D. (2001). The ACT domain family. Current opinion in structural biology 11, 694-700.

Cross, P. J., Allison, T. M., Dobson, R. C. J., Jameson, G. B., and Parker, E. J. (2013). Engineering allosteric control to an unregulated enzyme by transfer of a regulatory domain. Proceedings of the National Academy of Sciences of the United States of America 110, 2111-2116.

Cross, P. J., Dobson, R. C. J., Patchett, M. L., and Parker, E. J. (2011). Tyrosine latching of a regulatory gate affords allosteric control of aromatic amino acid biosynthesis. The Journal of biological chemistry 286, 10216-10224.

Dibble, C. C., Elis, W., Menon, S. Qin, W., Klekota, J., Asara, J. M., Finan, P. M., Kwiatkowski, D. J., Murphy, L. O., and Manning, B. D. (2012). TBC1D7 is a third subunit of the TSC1-TSC2 complex upstream of mTORC1. Molecular cell 47, 535-546.

Dibble, C. C., and Manning, B. D. (2013). Signal integration by mTORC1 coordinates nutrient input with biosynthetic output. Nature cell biology 15, 555-564.

Dumas, R., Cobessi, D., Robin, A. Y. Ferrer, J. L., and Curien, G. (2012). The many faces of aspartate kinases. Archives of biochemistry and biophysics 519, 186-193.

Efeyan, A., Zoncu, R., and SAbatini, D. M. (2012). Science Direct.com—Trends in Molecular Medicine—Amino acids and mTORC1: from lysosomes to disease. Trends in Molecular Medicine.

Floyd, J. C., Jr, Fajans, S. S., Conn, J. W., Knopf, R. F., and Rull, J. (1966). Stimulation of insulin secretion by amino acids. Journal of Clinical Investigation 45, 1487.

Fox, H. L., Pham, P. T., Kimball, S. R., Jefferson, L. S., and Lynch, C. J. (1998). Amino acid effects on translational repressor 4E-BP1 are mediated primarily by 1-leucine in isolated adipocytes. American Journal of Physiology Cell Physiology 275, C1232-C1238.

Grant, G. A. (2006). The ACT Domain: A Small Molecule Binding Domain and Its Role as a Common Regulatory Element. Journal of Biological Chemistry 281, 33825-33829.

Hara, K. (1998) Amino Acid Sufficiency and mTOR Regulate p70 S6 Kinase and eIF-4E BP1 through a Common Effector Mechanism," Journal of Biological Chemistry 273, 14484-14494.

Hirose, E., Nakashima, N., Sekiguchi, T. and Nishimoto, T. (1998) RagA is a functional homologue of *S. cerevisiae* Gtr1p involved in the Ran/Gsp1-GTPase pathway. Journal of cell science 111 (Pt 1), 11-21.

Huttlin, E. L., Ting, L., Bruckner, R. J., Gebreab, F., Gygi, M. P., Szpyt, J., Tam, S., Zarraga, G., Colby, G., Baltier, K., et al. (2015). The BioPlex Network: A Systematic Exploration of the Human Interactome. Cell 162, 425-440.

Jewell, J. L., Kim, Y. C., Russell, R. C., Yu, F.-X., Park, H. W., Plouffe, S. W., Tagliabracci, V. S., and Guan, K.-L. (2015). Metabolism. Differential regulation of mTORC1 by leucine and glutamin. Science 347, 194-198.

Jung, J., Genau, H. M., and Behrends, C. (2015). Amino Acid-Dependent mTORC1 Regulation by the Lysosomal Membrane Protein SLC38A9. Molecular and Cellular Biology 35, 2479-2494.

Kim, J. S., Ro, S.-H., Kim, M., Park, H.-W., Semple, I. A., Park, H., Cho, U.-S., Wang, W., Guan, K.-L., Karin, M., et al., (2015). Sestrin2 inhibits mTORC1 through modulation of Gator complexes. Scientific reports 5, 9502.

Kobe, B., Jennings, I. G., House, C. M., Michell, B. J., Goodwill, K. E., Santarsiero, B. D., Stevens, R. C., Cotton, R. G. H., and Kemp, B. E. (1999). Structural basis of autoregulation of phenylalanine hydroxylase. Nature Structural & Molecular Biology 6, 442, 448.

Lang, E. J., Cross, P. J., Mittelstadt, G., Jameson, G. B., and Parker, E. J. (2014). Allosteric ACTion: the varied ACT domains regulating enzymes of amino-acid metabolism. Current Opinion in Structural Biology 29, 102-111.

Lynch, C. J., Fox, H. L., Vary, T. C., Jefferson, L. S., and Kimball, S. R. (2000). Regulation of amino acid-sensitive TOR signaling by leucine analogues in adipocytes. Journal of Cellular Biochemistry 77, 234-251.

Menon, S., Dibble, C. C., Talbott, G., Hoxhaj, G., Valvezan, A. J., Takahashi, H., Cantley, L. C., and Manning, B. D. (2014). Spatial Control of the TSC COmplex Integrates Insulin and Nutrient Regulation of mTORC1 at the Lysosome. Cell 156, 771-785.

Parmigiani, A., Nourbakhsh, A., Ding, B., Wang, W., Kim, Y. C., Akopiants, K., Guan, K.-L, Karin, M., and Budanov, A. V. (2014). Sestrins Inhibit mTORC1 Kinase Activation through the GATOR Complex. Cell Reports 9, 1281-1291.

Petit, C. S., Roczniak-Ferguson, S. M. (2013). Recruitment of folliculin to lysosomes supports the amino acid-dependent activation of Rag GTPases. The Journal of Cell Biology 202, 1107-1122.

Rebsamen, M., Pochini, L., Stasyk, T., de Araujo, M. E. G., Galluccio, M., Kandasamy, R. K., Snijder, B., Fauster, A., Rudashevskaya, E. L., Bruckner, M., et al. (2015). SLC38A9 is a component of the lysosomal amino acid sensing machinery that controls mTORC1. Nature.

Rhoads, J. M., Niu, X., Odle, J., and Graves, L. M. (2006). Role of mTOR signaling in intestinal cell migration. American Journal of Physiology—Gastrointestinal and Liver Physiology 291, G510-G517.

Saito, K., Araki, Y., Kontani, K., Nishina, H., and Katada, T. (2005). Novel role of the small GTPase Rheb: its implication in endocytic pathway independent of the activation of mammalian target of rapamycin. Journal of Biochemistry 137, 423-430.

Sancak, Y., Bar-Peled, L., Zoncu, R., Markhard, A. L., Nada, S. and Sabatini, D. M. (2010) Ragulator-Rag complex targets mTORC1 to the lysosomal surface and is necessary for its activation by amino acids. Cell 141, 290-303.

Sancak, Y., Peterson, T. R., Shaul, Y. D., Lindquist, R. A., Thoreen, C. C., Bar-Peled, L. and Sabatini, D. M. (2008). The Rag GTPases bind raptor and mediate amino acid signaling to mTORC1. Science (New York, N.Y.) 320, 1496-1501.

Saxton, R. A., Knockenhauer, K. K., Wolfson, R. L., Chantranupong, L., Pacold, M. E., Wang, T., Schwartz, T. U., and Sabatini, D. M. (2015). Structural basis for leucine sensing by the Sestrin 2-mTORC1 pathway. Science, aad2087.

Schürmann, A., Brauers, A., Maßmann, S., Becker, W., and Joost, H.-G. (1995). Cloning of a Novel Family of Mammalian GTP-binding Proteins (RagA, RagBs, RagB1) with Remote Similarity to the Ras-related GTPases. The Journal of Biological Chemistry 270, 28982-28988.

Sekiguchi, T., Hirose, E., Nakashima, N., Ii, M., and Nishimoto, T. (2001). Novel G protein, Rag C and Rag D, interact with GTP-binding proteins, Rag A and Rag B. The Journal of Biological Chemistry 276, 7246-7257.

Siltberg-Liberles, J., and Martinez, A. (2009). Searching distant homologs of the regulatory ACT domain in phenylalanine hydroxylase. Amino Acids 36, 235-249.

Tan, K., Li, H., Zhang, R., Gu, M., Clancy, S. T., and Joachimiak, A. (2008). Structures of open (R) and close (T) states of prephenate dehydratase (PDT)—Implication of allosteric regulation by 1-phenylalanine. Journal of Structural Biology 162, 94-107.

Tsun, Z.-Y., Bar-Peled, L., Chantranupong, L., Zoncu, R., Wang, T., Kim, C., Spooner, E., and Sabatini, D. M. (2013). The Folliculin Tumor Suppressor Is a GAP for the FagC/D GTPases That Signal Amino Acid Levels to mTORC1. Molecular Cell 52, 495-505.

Wang, S., Tsun, Z.-Y., Wolfson, R. L., Shen, K., Wyant, G. A., Plovanich, M. E., Yuan, E. D., Jones, T. D., Chantranupong, L., Comb, W., et al. (2015). Metabolism. Lysosomal amino acid transport SLC38A9 signals arginine sufficiency to mTORC1. Science 347, 188-194.

Wolfson, R. L., Chantranupong, L, Saxton, R. A., Shen, K., Scaria, S. M., Cantor, J. R., and Sabatini, D. M. (2015). Sestrin2 is a leucine sensor for the mTORC1 pathway. Science, aab2674.

Wu, G., ang Morris, S. M. (1998). Arginine metabolism: nitric oxide and beyond. Biochemical Journal 336 (Pt 1), 1-17.

Yao, K., Yin, Y.-L, Chu, W., Liu, Z., Deng, D., Li, T., Huang, R., Zhang, J., Tan, B., Wang, W., et al. (2008). Dietary Arginine Supplementation Increases mTOR Signaling Activity in Skeletal Muscle of Neonatal Pigs. The Journal of Nutrition 138, 867-872.

Zoncu, R., Bar-Peled, L., Efeyan, A., Wang, S., Sancak, Y. and Sabatini, D. M. (2011). mTORC1 Senses Lysosomal Amino Acids Through an Inside-Out Mechanism That Requires the Vacuolar H+-ATPase. Science Signaling 334, 678-683.

What is claimed is:

1. A method of identifying a test compound as an activator of mTORC1 activity comprising the steps of:
   a) providing a mixture comprising:
      (i) a first polypeptide comprising SEQ ID NO: 7 and SEQ ID NO: 15; and
      (ii) a second polypeptide selected from: a polypeptide or protein complex comprising the amino acid sequence of one or more of WDR24, WDR59, or mios,
   under conditions that allow the first polypeptide to associate with the second polypeptide;
   b) incubating the mixture of a) with the test compound;
   c) determining whether the amount of the first polypeptide associated with the second polypeptide is altered in the presence of the test compound as compared to either the absence of the test compound or the presence of a negative control, wherein if the amount of association is decreased the test compound is identified as an activator of mTORC1 activity.

2. The method of claim 1, wherein the first polypeptide comprises CASTOR1.

3. The method of claim 1, wherein the second polypeptide is present as part of a protein complex, wherein the protein complex is GATOR2.

4. The method of claim 1, wherein:
   the first polypeptide is bound to a first tag; and/or
   the second polypeptide is bound to a second tag; and
   wherein the step of determining the amount of the first polypeptide associated with the second polypeptide: (a) comprises detecting at least one of the first or second tag or a product of the first and second tag; and (b) distinguishes between the first polypeptide associated with the second polypeptide and the first polypeptide not associated with the second polypeptide.

5. The method of claim 4, wherein:
   the first tag is present and comprises a first epitope not present in the first or second polypeptide;
   the second tag is present and comprises a second epitope not present in the first or second polypeptide;
   detecting the first tag comprises binding a first antibody specific for the first epitope; and
   detecting the second tag comprises binding a second antibody specific for the second epitope.

6. The method of claim 4, wherein:
   only one of the first tag or second tag is present and the tag is a fluorescent moiety bound to the N- or C-terminus of the first polypeptide or the second polypeptide; and
   detecting the association of the first polypeptide with the second polypeptide comprises fluorescence polarization.

7. The method of claim 1, wherein:
   one of the first polypeptide or second polypeptide is bound to a solid support; and
   detecting the association of the first polypeptide with the second polypeptide comprises surface plasmon resonance.

* * * * *